United States Patent
Banville et al.

(10) Patent No.: US 7,192,948 B2
(45) Date of Patent: Mar. 20, 2007

(54) BICYCLIC HETEROCYCLES AS HIV INTEGRASE INHIBITORS

(75) Inventors: Jacques Banville, St-Hubert (CA); Gilles Bouthillier, Mercier (CA); B. Narasimhulu Naidu, Durham, CT (US); Roger Remillard, Napierville (CA); Michael A. Walker, Durham, CT (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 11/138,726

(22) Filed: May 26, 2005

(65) Prior Publication Data

US 2005/0267132 A1    Dec. 1, 2005

Related U.S. Application Data

(60) Provisional application No. 60/603,371, filed on Aug. 20, 2004, provisional application No. 60/575,513, filed on May 28, 2004.

(51) Int. Cl.
| | |
|---|---|
| *A61K 31/554* | (2006.01) |
| *A61K 31/519* | (2006.01) |
| *A61K 31/541* | (2006.01) |
| *C07D 279/02* | (2006.01) |
| *C07D 487/04* | (2006.01) |
| *C07D 281/02* | (2006.01) |
| *A61P 31/20* | (2006.01) |
| *C07D 239/66* | (2006.01) |

(52) U.S. Cl. .............. 514/211.1; 514/259.2; 514/222.2; 544/3; 544/278; 540/552

(58) Field of Classification Search ......... 544/278, 544/48, 3; 514/259.2, 224.2, 211.1, 222.2; 540/552
See application file for complete search history.

(56) References Cited

U.S. PATENT DOCUMENTS

2004/0006065 A1    1/2004    Glunz

FOREIGN PATENT DOCUMENTS

| WO | WO 2003/035076 A1 | 5/2003 |
|---|---|---|
| WO | WO 2003/035077 A1 | 5/2003 |
| WO | WO 2004/058756 A1 | 7/2004 |
| WO | WO 2004/058757 A1 | 7/2004 |
| WO | WO 2005/061490 A1 | 7/2005 |
| WO | WO 2005/061501 A2 | 7/2005 |
| WO | WO 2006/060731    | 6/2006 |
| WO | WO 2006/103399    | 10/2006 |

OTHER PUBLICATIONS

U.S. Appl. No. 10/755,642, filed Jan. 12, 2004, Michael A. Walker, et al.

*Primary Examiner*—Mark L. Berch
*Assistant Examiner*—Susanna Moore
(74) *Attorney, Agent, or Firm*—James Epperson

(57) ABSTRACT

The invention encompasses a series cyclic bicyclic heterocyclic compounds of Formula I which are inhibitors of HIV integrase and prevent viral integration into human DNA. This action makes the compounds useful for treating HIV infection and AIDS. The invention also encompasses pharmaceutical compositions and methods for treating those infected with HIV

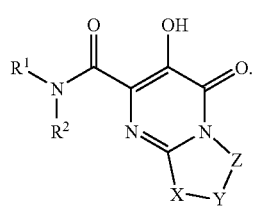

14 Claims, No Drawings

BICYCLIC HETEROCYCLES AS HIV INTEGRASE INHIBITORS

CROSS REFERENCE TO RELATED APPLICATIONS

This application claims the benefit of U.S. Provisional Application Ser. Nos. 60/603,371 filed Aug. 20, 2004 and 60/575,513 filed May 28, 2004.

BACKGROUND OF THE INVENTION

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics (UNAIDS: Report on the Global HIV/AIDS Epidemic, December 1998), indicate that as many as 33 million people worldwide are infected with the virus. In addition to the large number of individuals already infected, the virus continues to spread. Estimates from 1998 point to close to 6 million new infections in that year alone. In the same year there were approximately 2.5 million deaths associated with HIV and AIDS.

There are currently a number of antiviral drugs available to combat the infection. These drugs can be divided into three classes based on the viral protein they target and their mode of action. In particular, saquinavir, indinavir, ritonavir, nelfinavir and amprenavir are competitive inhibitors of the aspartyl protease expressed by HIV. Zidovudine, didanosine, stavudine, lamivudine, zalcitabine and abacavir are nucleoside reverse transcriptase inhibitors that behave as substrate mimics to halt viral cDNA synthesis. The non-nucleoside reverse transcriptase inhibitors, nevaripine, delavirdine and efavirenz inhibit the synthesis of viral cDNA via a non-competitive (or uncompetitive) mechanism. Used alone these drugs are effective in reducing viral replication. The effect is only temporary as the virus readily develops resistance to all known agents. However, combination therapy has proven very effective at both reducing virus and suppressing the emergence of resistance in a number of patients. In the US, where combination therapy is widely available, the number of HIV-related deaths has declined (Palella, F. J.; Delany, K. M.; Moorman, A. C.; Loveless, M. O.; Furher, J.; Satten, G. A.; Aschman, D. J.; Holmberg, S. D. N. Engl. J. Med. 1998, 338, 853–860).

Unfortunately, not all patients are responsive and a large number fail this therapy. In fact, approximately 30–50% of patients ultimately fail combination therapy. Treatment failure in most cases is caused by the emergence of viral resistance. Viral resistance in turn is caused by the rapid turnover of HIV-1 during the course of infection combined with a high viral mutation rate. Under these circumstances incomplete viral suppression caused by insufficient drug potency, poor compliance to the complicated drug regiment as well as intrinsic pharmacological barriers to exposure provides fertile ground for resistance to emerge. More disturbing are recent findings which suggest that low-level replication continues even when viral plasma levels have dropped below detectable levels (<50 copies/mL) (Carpenter, C. C.; Cooper, D. A.; Fischl, M. A.; Gatell, J. M.; Gazzard, B. G.; Hammer, S. M.; Hirsch, M. S.; Jacobsen, D. M.; Katzenstein, D. A.; Montaner, J. S.; Richman, D. D.; Saag, M. S.; Schechter, M.; Schooley, R. T.; Thompson, M. A.; Vella, S.; Yeni, P. G.; Volberding, P. A. JAMA 2000, 283, 381–390). Clearly there is a need for new antiviral agents, preferably targeting other viral enzymes to reduce the rate of resistance and suppress viral replication even further.

HIV expresses three enzymes, reverse transcriptase, an aspartyl protease, and integrase. All three are targets for treating AIDS and HIV infection. HIV integrase catalyzes insertion of the viral cDNA into the host cell genome, which is a critical step in the viral life cycle. HIV integrase inhibitors belonging to a class of diketo acid compounds prevented viral integration and inhibited HIV-1 replication in cells (Hazuda et al. Science 2000, 287, 646). And recently, HIV integrase inhibitors have been accepted into clinical trials for treating AIDS and HIV infection (Neamati Expert. Opin. Ther. Patents 2002, 12, 709, Pais and Burke Drugs Fut. 2002, 27, 1101).

DESCRIPTION OF THE INVENTION

The invention encompasses compounds of Formula I, including pharmaceutically acceptable salts and solvates, their pharmaceutical compositions, and methods for inhibiting HIV integrase and treating those infected with HIV.

One aspect of the invention is a compound of Formula I

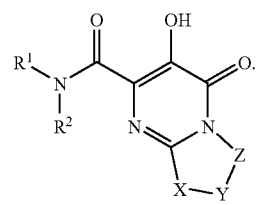

wherein:
$R^1$ is $C_{1-6}(Ar^1)$alkyl;
$R^2$ is hydrogen, hydroxy, $C_{1-6}$alkyl, or $C_{1-6}$alkoxy;
$R^3$ is hydrogen, halo, hydroxy, cyano, $C_{1-6}$alkyl, $C_{1-6}$haloalkyl, $C_{1-6}$alkoxy, $C_{1-6}$haloalkoxy, $N(R^6)SO_2R^7$, $N(R^6)COR^7$, $N(R^6)CO_2R^7$, $OCOR^7$, $OCO_2R^7$, $OCON(R^6)(R^6)$, $COR^7$, $CO_2R^6$, $CON(R^6)(R^6)$, $SOR^7$, $SO_2R^7$, $SO_2N(R^6)(R^6)$, or $Ar^2$;
$R^4$ is hydrogen, halo, hydroxy, cyano, $C_{1-6}$alkyl, $C_{1-6}$alkoxy, $C_{1-6}$haloalkyl, or $C_{1-6}$haloalkoxy;
$R^5$ is hydrogen, halo, hydroxy, cyano, $C_{1-6}$alkyl, $C_{1-6}$alkoxy, $C_{1-6}$haloalkyl, or $C_{1-6}$haloalkoxy;
$R^6$ is hydrogen, $C_{1-6}$alkyl, or $C_{3-7}$cycloalkyl;
$R^7$ is $C_{1-6}$allyl or $C_{3-7}$cycloalkyl;
$R^8$ is hydrogen, $C_{1-6}$alkyl, or benzyl;
$R^9$ and $R^{10}$ taken together are $C_{3-5}$alkylene;
$Ar^1$ is

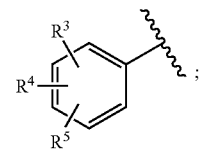

$Ar^2$ is tetrazolyl, triazolyl, pyrazolyl, imidazolyl, pyrrolyl, or dixothiazinyl, and is substituted with 0–2 substituents selected from the group consisting of amino, oxo, halo, and $C_{1-6}$alkyl; and
X—Y-Z is $N(R^8)COC(R^8)_2$, $N(R^8)COC(R^8)_2C(R^8)_2$, $N(R^8)COC(R^8)_2C(R^8)_2C(R^8)_2$, $N(R^8)SO_2C(R^8)_2$, $N(R^8)SO_2C(R^8)_2C(R^8)_2$, $N(R^8)N(R^8)COC(R^8)_2$, $N(R^8)N(R^8)COC(R^8)_2C(R^8)_2$, $N(R^9)N(R^{10})COC(R^8)_2$, $N(R^9)N(R^{10})COC(R^8)_2C(R^8)_2$, $C(R^8)_2N(R^8)CO$, $C(R^8)_2N(R^8)COC(R^8)_2$, $C(R^8)_2N(R^8)COC(R^8)_2C(R^8)_2$, $C(R^9)_2N(R^{10})CO$, $C(R^9)_2N(R^{10})COC(R^8)_2$, $C(R^9)_2N(R^{10})COC(R^8)_2C(R^8)_2$, $SC(R^8)_2C(R^8)_2$, $SC(R^8)_2C(R^8)_2$, $SC(R^8)_2C(R^8)_2C(R^8)_2C(R^8)_2$;

or a pharmaceutically acceptable salt or solvate thereof.

Another aspect of the invention is a compound of Formula I where $R^1$ is

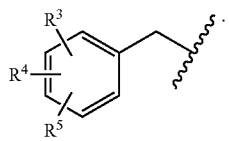

Another aspect of the invention is a compound of Formula I where $R^1$ is

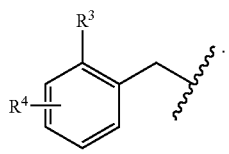

Another aspect of the invention is a compound of Formula I where $R^2$ is hydrogen.

Another aspect of the invention is a compound of Formula I where $R^3$ is hydrogen, chloro, flouro, methyl, $SO_2N(R^6)(R^6)$, or $NHCOR^7$; $R^4$ is hydrogen, chloro, flouro, or methyl; and $R^5$ is hydrogen.

Another aspect of the invention is a compound of Formula I where $R^3$ is triazinyl substituted with 0–1 methyl groups; $R^4$ is hydrogen, chloro, flouro, or methyl; and $R^5$ is hydrogen.

Another aspect of the invention is a compound of Formula I where $R^6$ is hydrogen or $C_{1-6}$alkyl.

Another aspect of the invention is a compound of Formula I where $R^7$ is $C_{1-6}$alkyl.

Another aspect of the invention is a compound of Formula I where $R^8$ is hydrogen or methyl.

Another aspect of the invention is a compound of Formula I where X—Y-Z is $N(R^8)COCH_2$, $N(R^8)COCH_2CH_2$, $N(R^8)COCH_2CH_2CH_2$, $N(R^8)SO_2CH_2$, $N(R^8)SO_2CH_2CH_2$, $N(R^8)SO_2CH_2CH_2CH_2$, $N(R^8)N(R^8)COCH_2$, $N(R^8)N(R^8)COCH_2CH_2$, $N(R^9)N(R^{10})COCH_2$, $N(R^9)N(R^{10})COCH_2CH_2$, $C(R^8)_2N(R^8)CO$, $C(R^8)_2N(R^8)COCH_2$, $C(R^8)_2N(R^8)COCH_2CH_2$, $C(R^9)_2N(R^{10})CO$, $C(R^9)_2N(R^{10})COCH_2$, $C(R^9)_2N(R^{10})COCH_2CH_2$, $SCH_2CH_2$, $SCH_2CH_2CH_2$, or $SCH_2CH_2CH_2CH_2$.

Another aspect of the invention is a compound of Formula I where $R^9$ and $R^{10}$ taken together are propylene, butylene, or pentylene.

For a compound of Formula I, any scope of $R^1$, $R^2$, $R^3$, $R^4$, $R^5$, $R^6$, $R^7$, $R^8$, $R^9$, $R^{10}$, $Ar^1$, $Ar^2$, and X—Y-Z can be used independently with any scope of any other substituent.

"Alkyl," "alkoxy," "haloalkyl," "alkylene" and related terms with an alkyl moiety include straight and branched configurations. A term such as "$C_{1-6}(R)$alkyl" means a straight or branched alkyl group of one to six carbons substituted with the substituent R. "Haloalkyl" and "halophenyl" include all permutations of halogenated alkyl or phenyl groups, from monohalo to perhalo. "Aryl" means an aromatic ring system and includes carbocyclic and heterocyclic systems. Some substituents are divalent, such as X—Y-Z. Asymmetric divalent substituents may be attached in either of the two configurations.

"Dioxothiazinyl" means

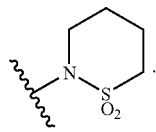

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

The invention also includes all solvated forms of the compounds, particularly hydrates. Solvates do not contribute significantly to the physiological activity or toxicity of the compounds and as such function as pharmacological equivalents.

Solvates may form in stoichiometric amounts or may form from adventitious solvent or a combination of both. One type of solvate is hydrate, and some hydrated forms include monohydrate, hemihydrate, and dihydrate.

Some of the compounds of the invention exist in stereoisomeric forms. The invention includes all stereoisomeric forms of the compounds including enantiomers and diastereomers. An example of enantiomers is shown below. Methods of making and separating stereoisomers are known in the art.

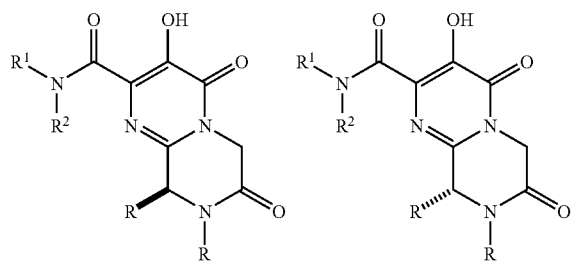

The invention includes all tautomeric forms of the compounds. An example of a tautomeric pair is shown below.

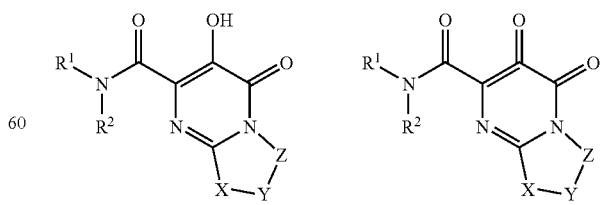

Synthetic Methods

The compounds of this invention can be made by various methods known in the art including those of the following schemes and in the specific embodiments section. The variables shown in the synthetic schemes are distinct from and should not be confused with the variables in the claims or the rest of the specification. The variables in the schemes are meant only to illustrate how to make some of the compounds of this invention.

Some compounds can be synthesized from an appropriately substituted heterocycle I-1 according to Scheme I, where $R_a$ and P can serve as protecting groups (see Greene, T. W. and Wutz, P. G. M. Protective Groups in Organic Synthesis, Second Edition, 1991, John Wiley and Sons, New York). When P is benzyl or substituted benzyl it can be removed by hydrogenolysis ($H_2$—Pd/C) or acid hydrolysis (trifluoroacetic acid) to yield intermediate I-2. I-2 can be transaminated to I-4 by reaction with amine I-3. When $R_a$ is a lower alkyl group, $R_a$ can be removed under ester hydrolysis conditions, such as treatment with NaOH, LiOH, or KOH to deliver the corresponding carboxylic acid I-5. Alternatively, $R_a$ can be removed by nucleophilic displacement using NaI. When $R_a$ is benzyl and substituted benzyl, $R_a$ can be removed by hydrogenolysis. Intermediate I-5 can be coupled using amide bond forming reagents such as BOP or other reagents (see March, J. Advanced Organic Chemistry, Fourth Edition 1992 John Wiley & Sons, New York). The resulting intermediate I-6 can be deprotected as described for intermediate I-1.

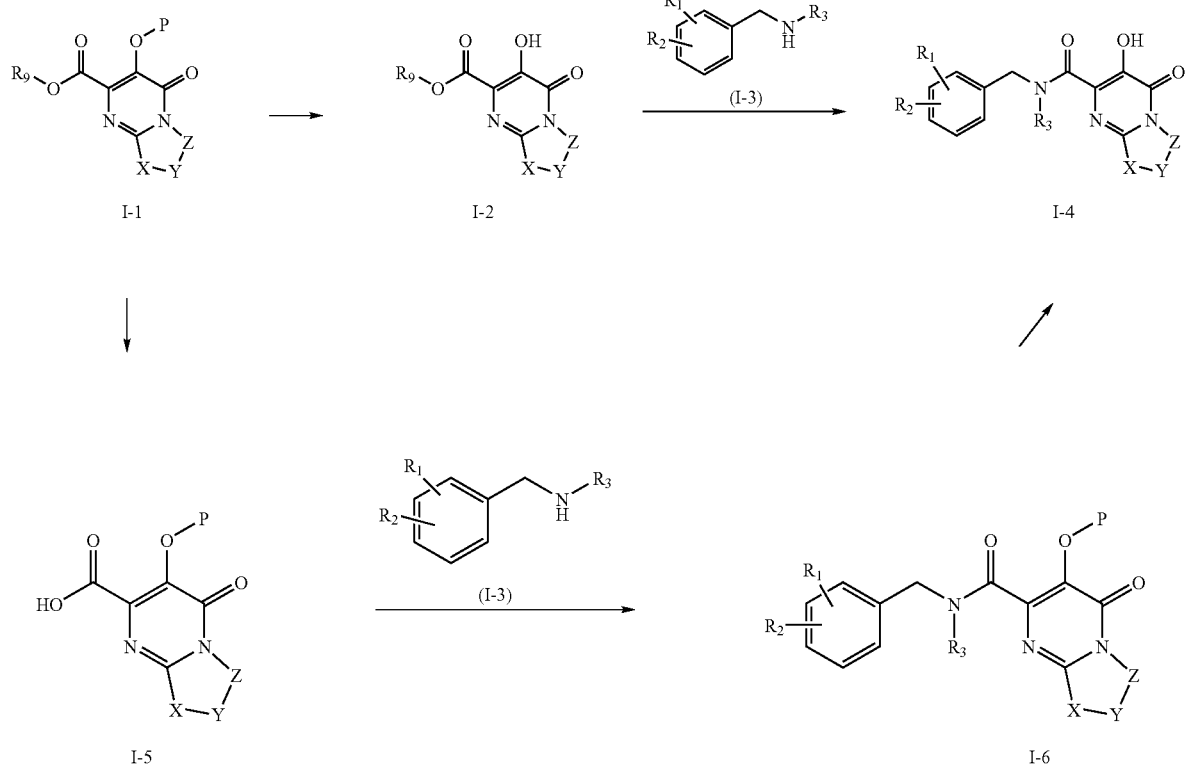

Scheme I.

(P = protecting group)
$R_a$ = alkyl, aryl, benzyl

Some bicyclic heterocycles can be synthesized according to a variety of methods, some examples of which are illustrated in Scheme II. Using methods similar to that described in Sunderland, J. S.; Botta, M.; Aime, S.; Raymond, K. N. Inorg. Chem. (2001), 40, 6756–6756, II-1 and II-2 can be condensed to provide intermediate II-3. Intermediate II-3 can be reacted with 2-methylisothiourea to yield pyrimidinone II-4. Pyrimidinone II-4 can be transformed to II-5 by addition of an appropriately substituted functional group to the N-3 of the pyrimidinone. One suitable functional group is where B is an electrophile such as Cl, Br or I or Z combined with Z is an alkylcarboxylate such as $CO_2CH_3$. The sulfide of II-4 can be activated for nucleophilic displacement by treating with an appropriate oxidizing agent such as mCPBA to form the sulfone II-6. The sulfone can be displaced by an appropriately functionalized group to yield II-7. With appropriate choices of substituents, cyclization of II-7 can be effected to yield I-1.

Scheme II.

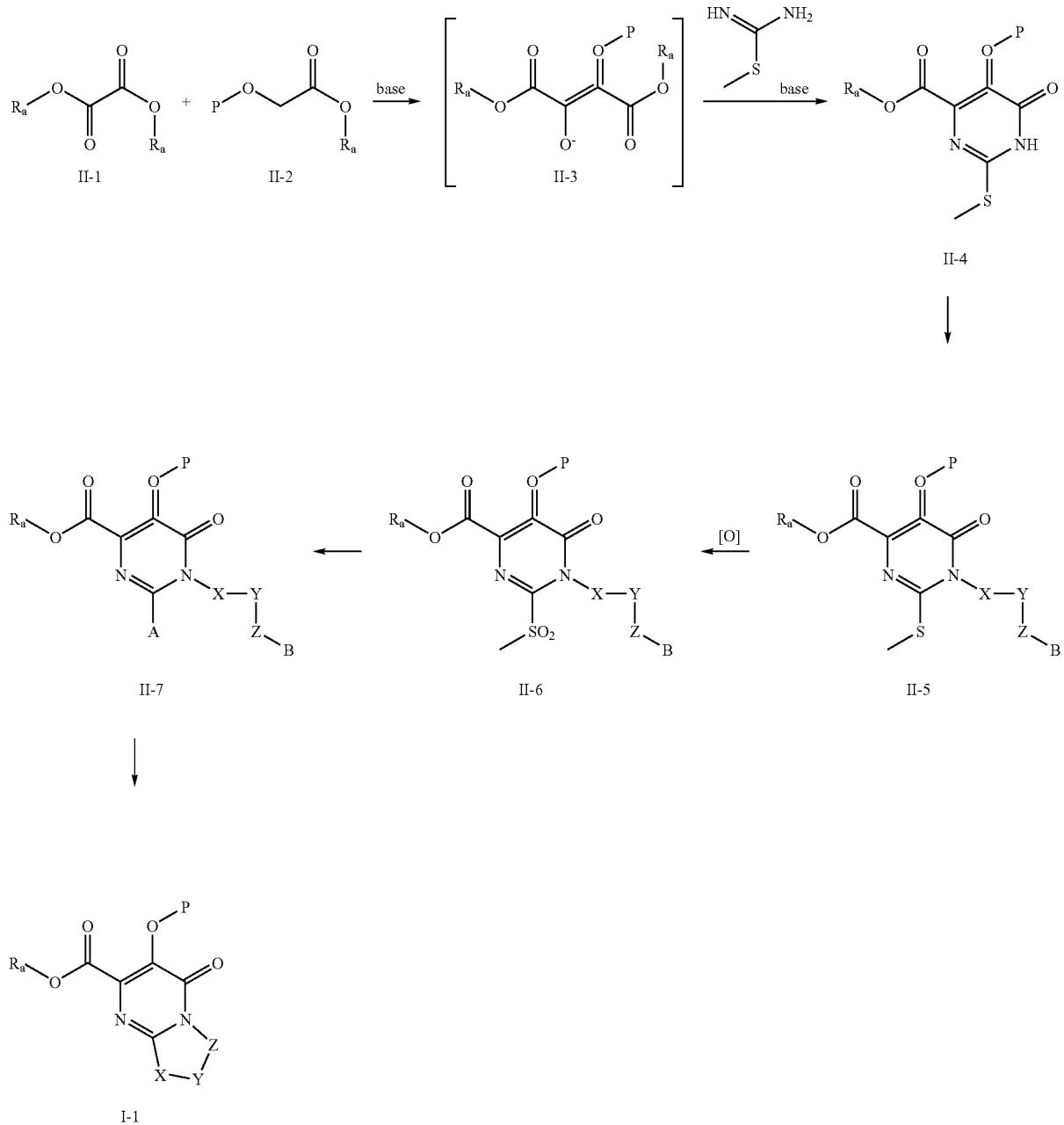

As illustrated in Scheme III, diethyloxalate can be reacted with ethyl 2-(benzyloxy)acetate to provide intermediate III-1. This intermediate need not be isolated but can be used directly in the next step of the sequence. According to Scheme III, this intermediate can be condensed with 2-methylisothiourea, in much the same way as described in Scheme II. Intermediate III-2 and methyl-bromoacetate can be treated calcium hydride to effect alkylation of the pyrimidinone, to provide III-3. The sulfide of III-3 can be oxidized using any of a number of methods known to those skilled in the art to produce the corresponding sulfone, intermediate III-4. Upon treatment of this intermediate with an appropriate amine ($R_aNH_2$) the sulfone group can be displaced and ring closure ensues to yield the bicyclic heterocycle, intermediate III-5. This intermediate can be converted to the final compound, III-7, by different paths. In one method the benzyl group is removed to provide intermediate III-6, which can be treated with an appropriate amine at elevated temperature to effect amide bond formation. Alternatively, the ethyl ester of III-5 can be saponified to provide a carboxylic acid, III-8, suitable for condensing with amines using methods well known to those skilled in the art to form intermediate III-9. After amide formation, the benzyl protecting group can be removed using methods similar to those described above.

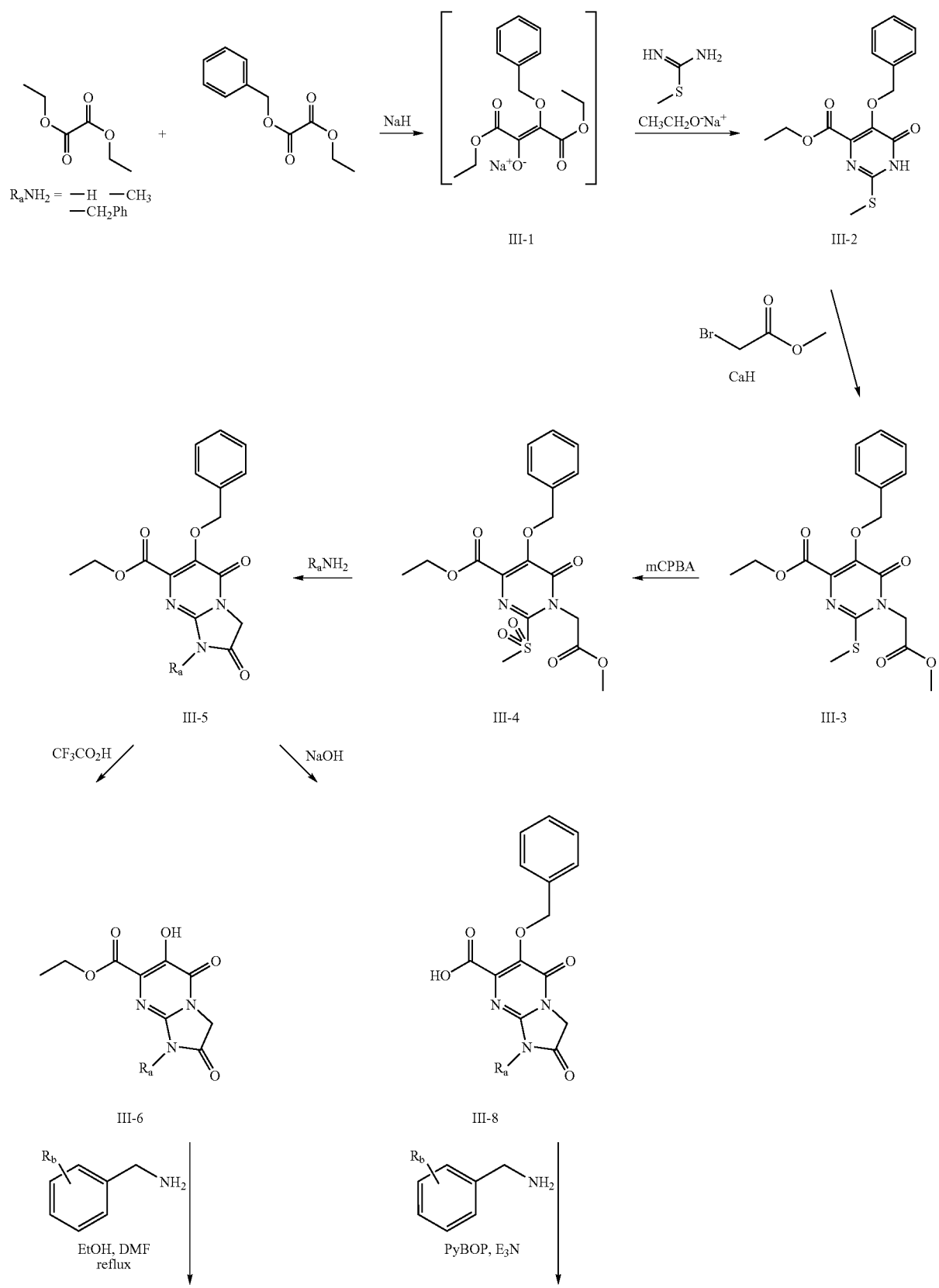

-continued
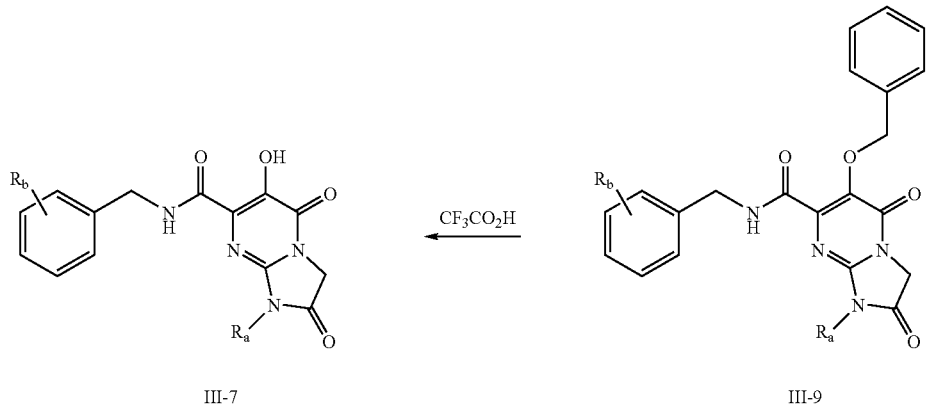
Two sequences, related to that shown in Scheme III, are illustrated by Scheme IV and Scheme V.
Scheme IV
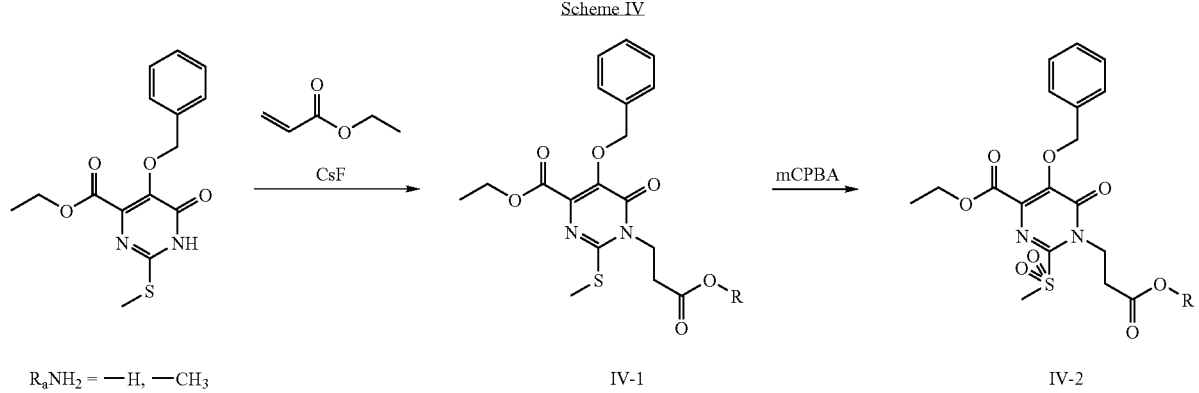
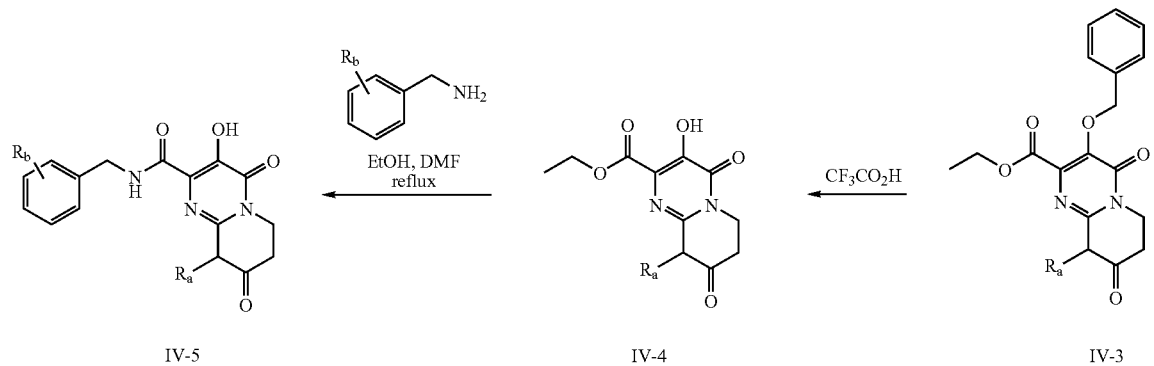

Scheme V

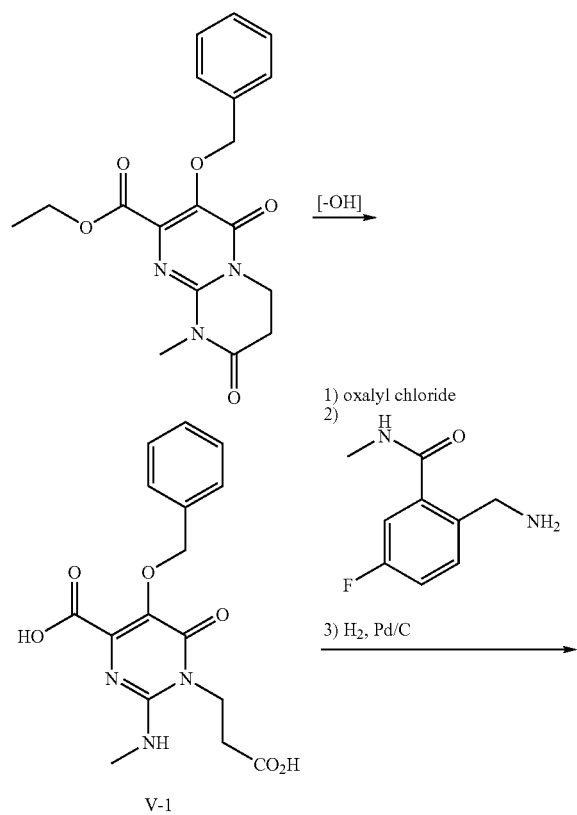

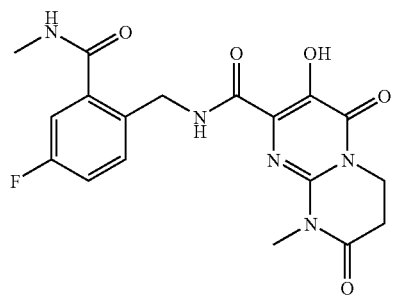

V-2

In Scheme VI, intermediate VI-1 can be synthesized using a method analogous to that provided above. Namely, the intermediate provided by the Claisen condensation between diethyloxalate and ethyl 2-(benzyloxy)acetate can be reacted with guanidine to produce VI-1. Treatment of this intermediate with 2-chloroethanesulfonyl chloride can yield the carboxylic acid VI-2. Transformation of this intermediate via amidation and debenzylation can be accomplished according to the methods previously described.

Scheme VII

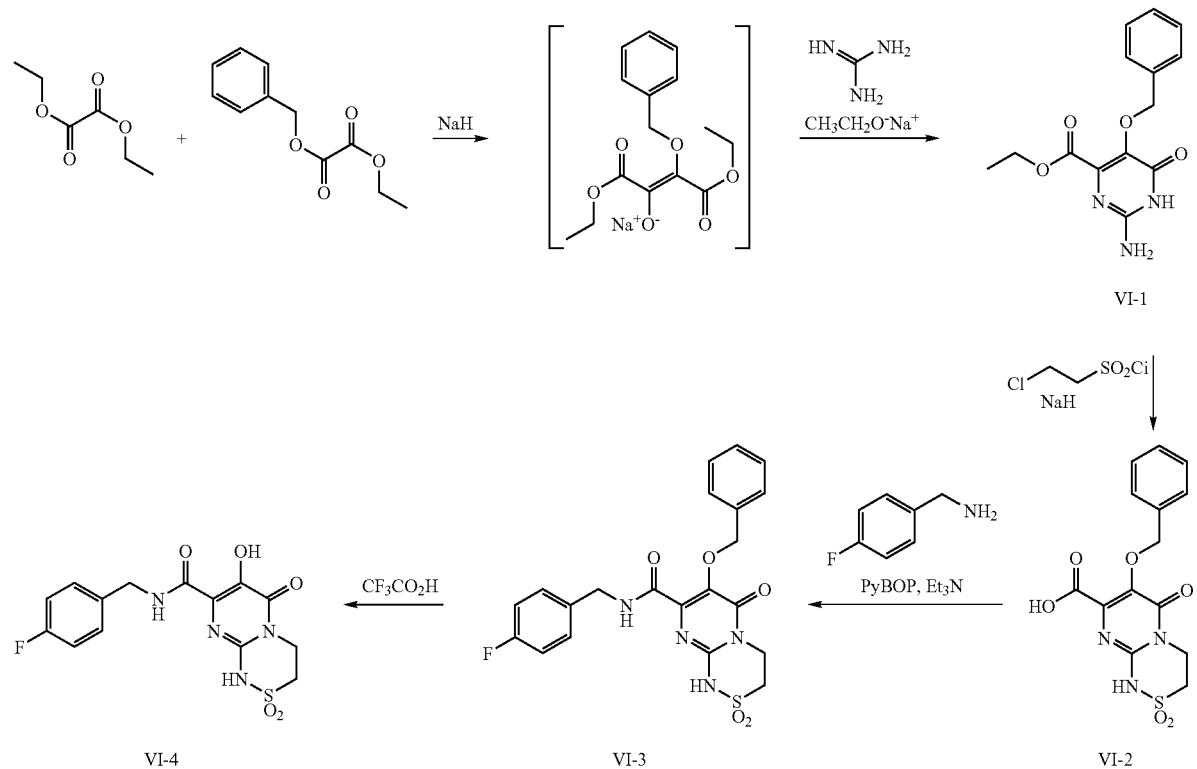

A further illustration of the methods that can be used to synthesize compounds of the current invention is provide by Scheme VII.

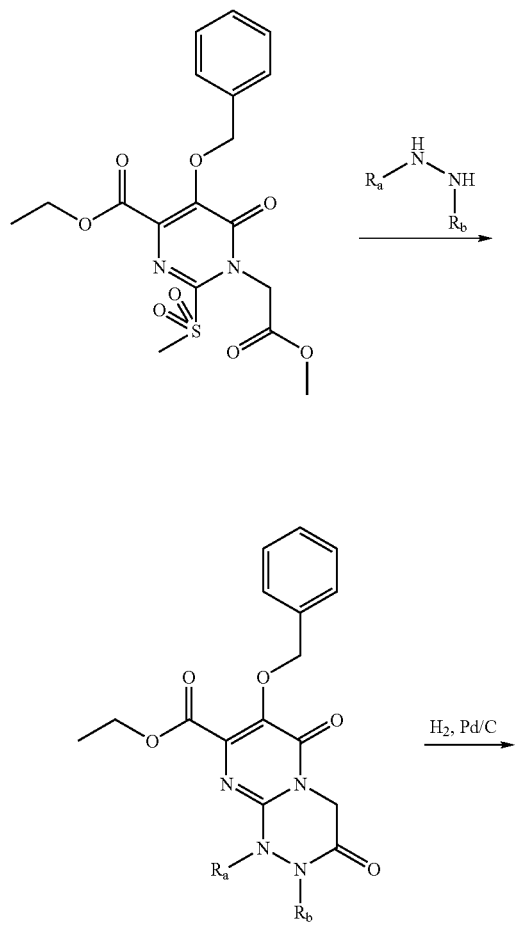

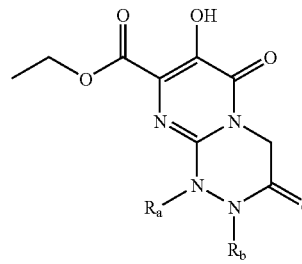

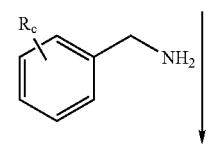

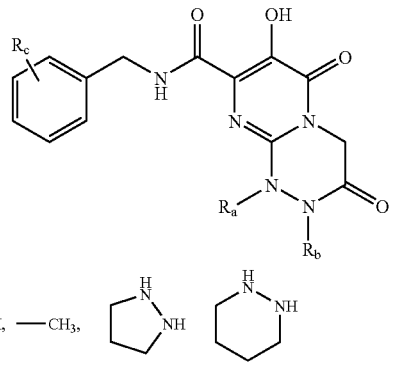

Certain compounds of the invention can be synthesized according to Schemes VIII and IX. In these schemes the intermediate provided by the Claisen condensation between diethyloxalate and ethyl 2-(benzyloxy)acetate can be reacted with the corresponding 4,5-dihydrothiazole to form the bicyclic heterocycles VIII-1 and IX-1. Both intermediates are suitable for further transformation using the methods described above.

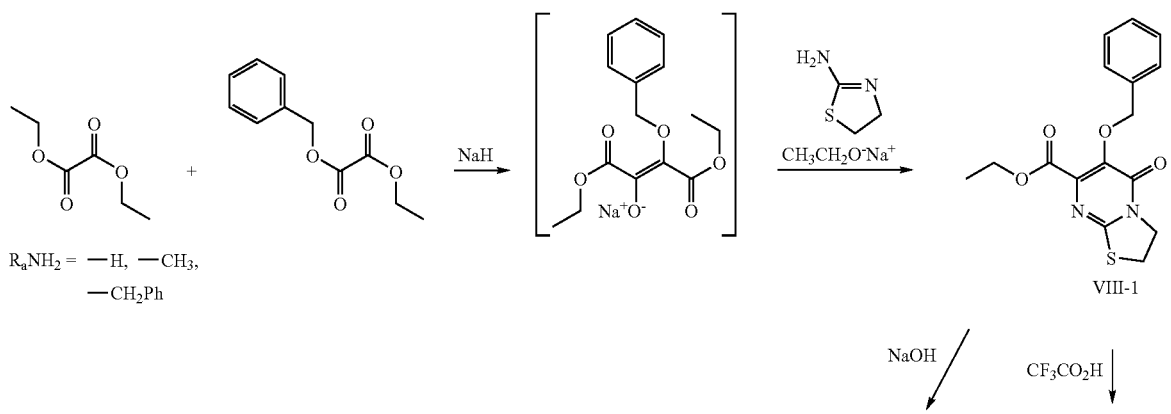

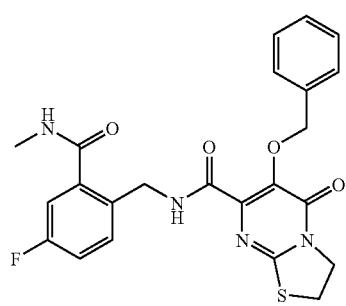
VIII-5
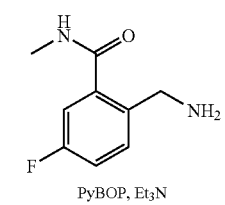
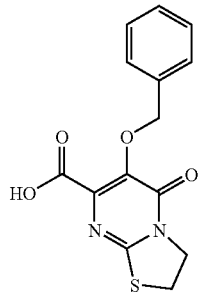
VIII-4
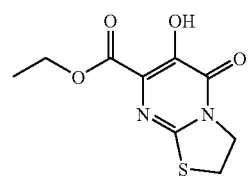
VIII-2
CF₃CO₂H ↓
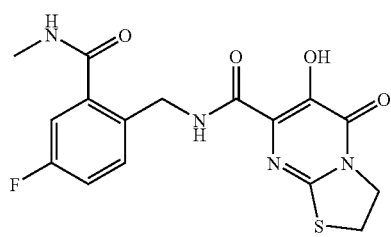
VIII-6
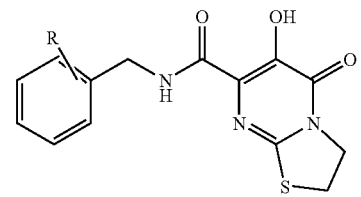
VIII-3
Scheme IX
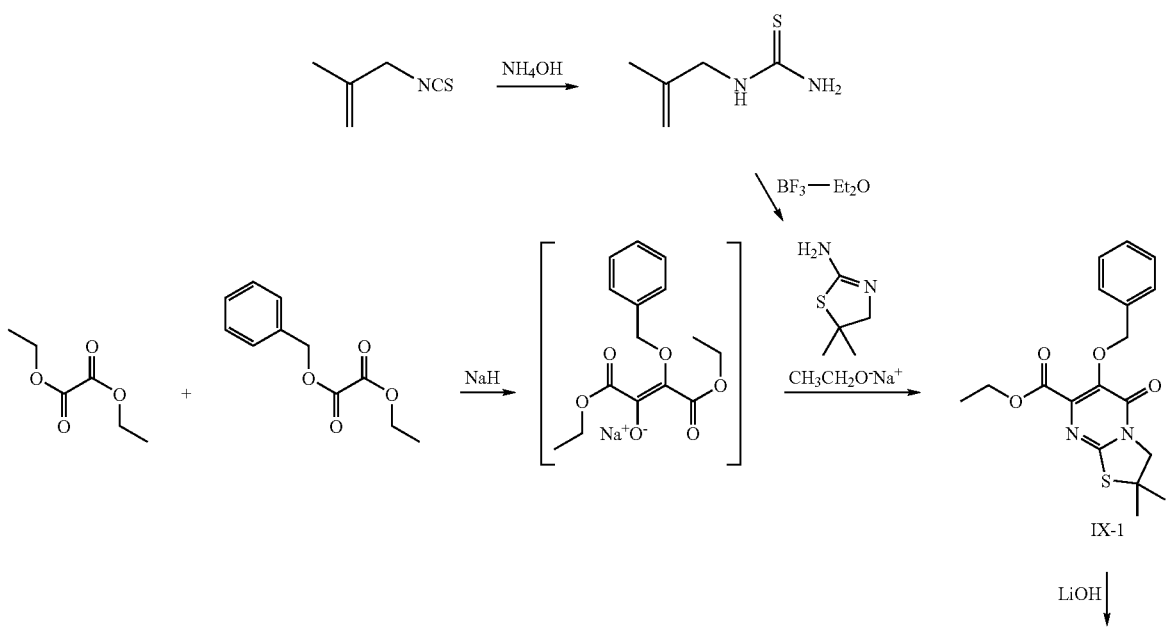

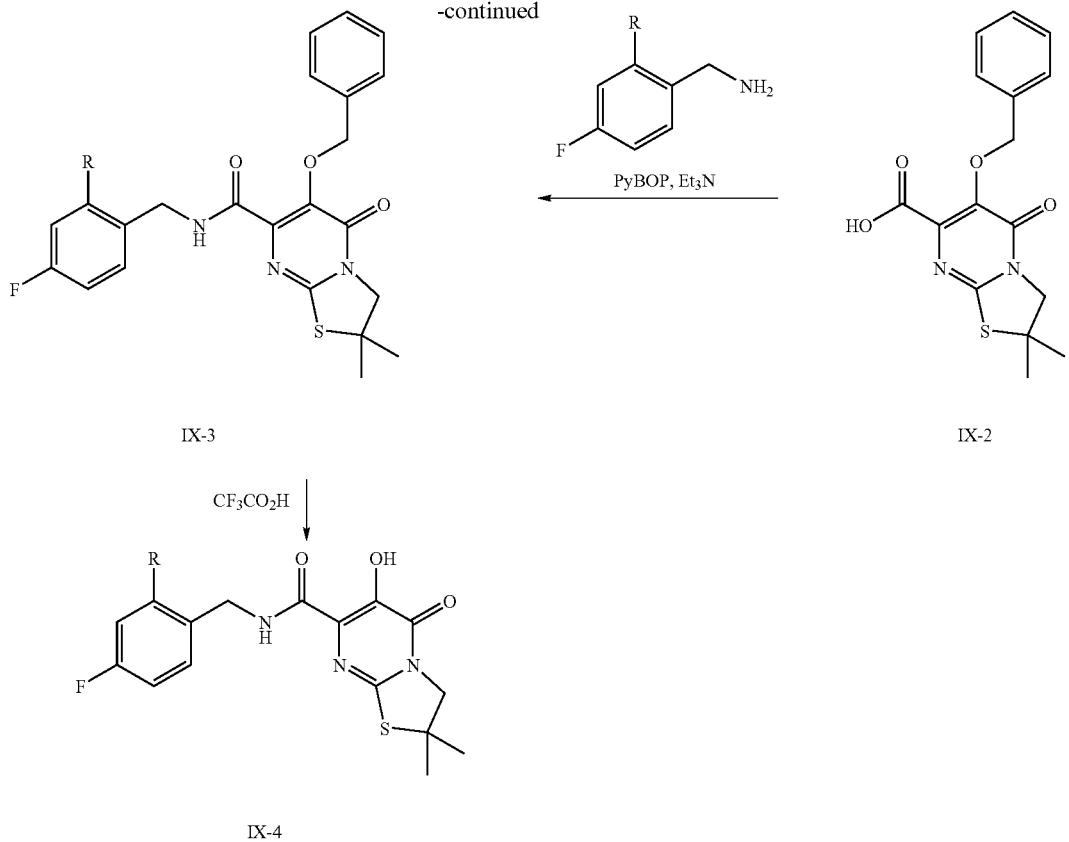

IX-3

IX-2

IX-4

Alternative methods for the synthesis of compounds of the current invention are illustrated in Schemes X–XII. In these Schemes use is made of a method described in the literature (Culbertson, T. P. *Journal of Heterocyclic Chemistry*, 1979, 16, 1423–1424), wherein an appropriate nitrile is sequentially converted to a pyrimidinone heterocycle in manner similar to that shown. Synthesis of the corresponding bicyclic heterocycle can then be accomplished via a two step or one step procedure as illustrated in the schemes.

Scheme X

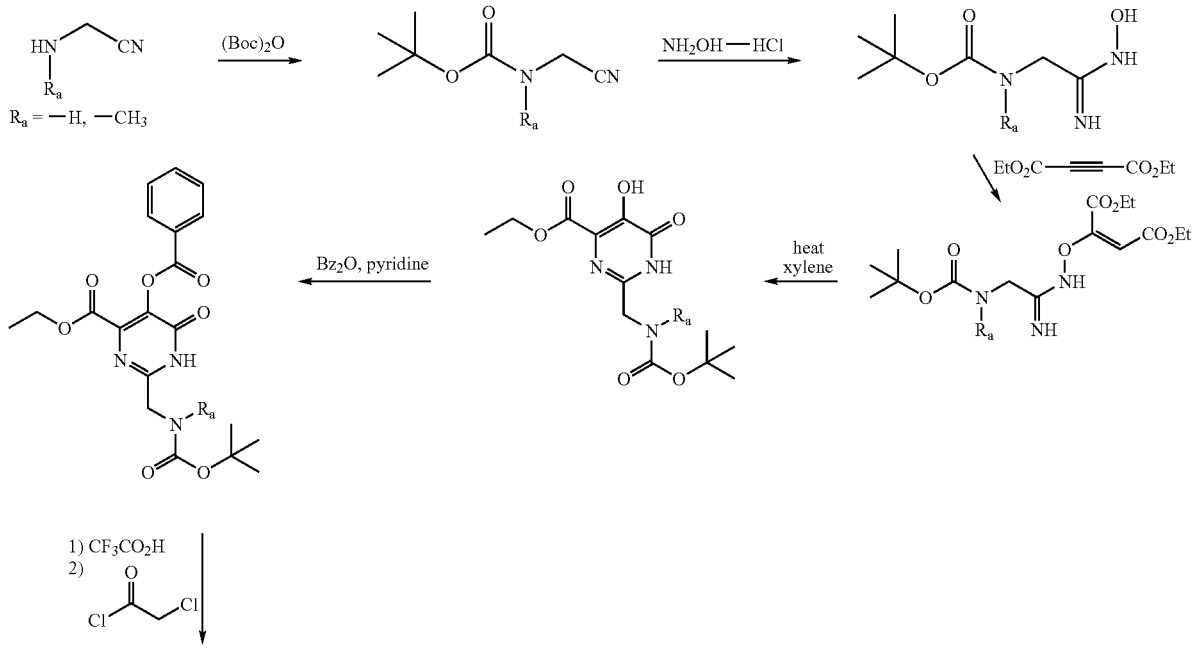

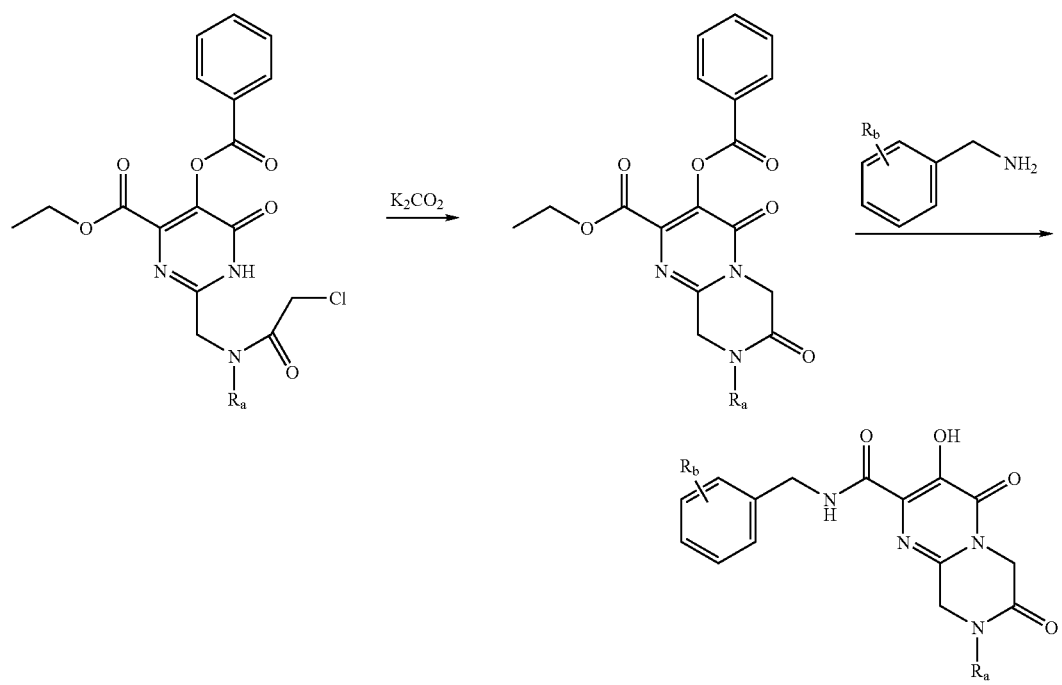
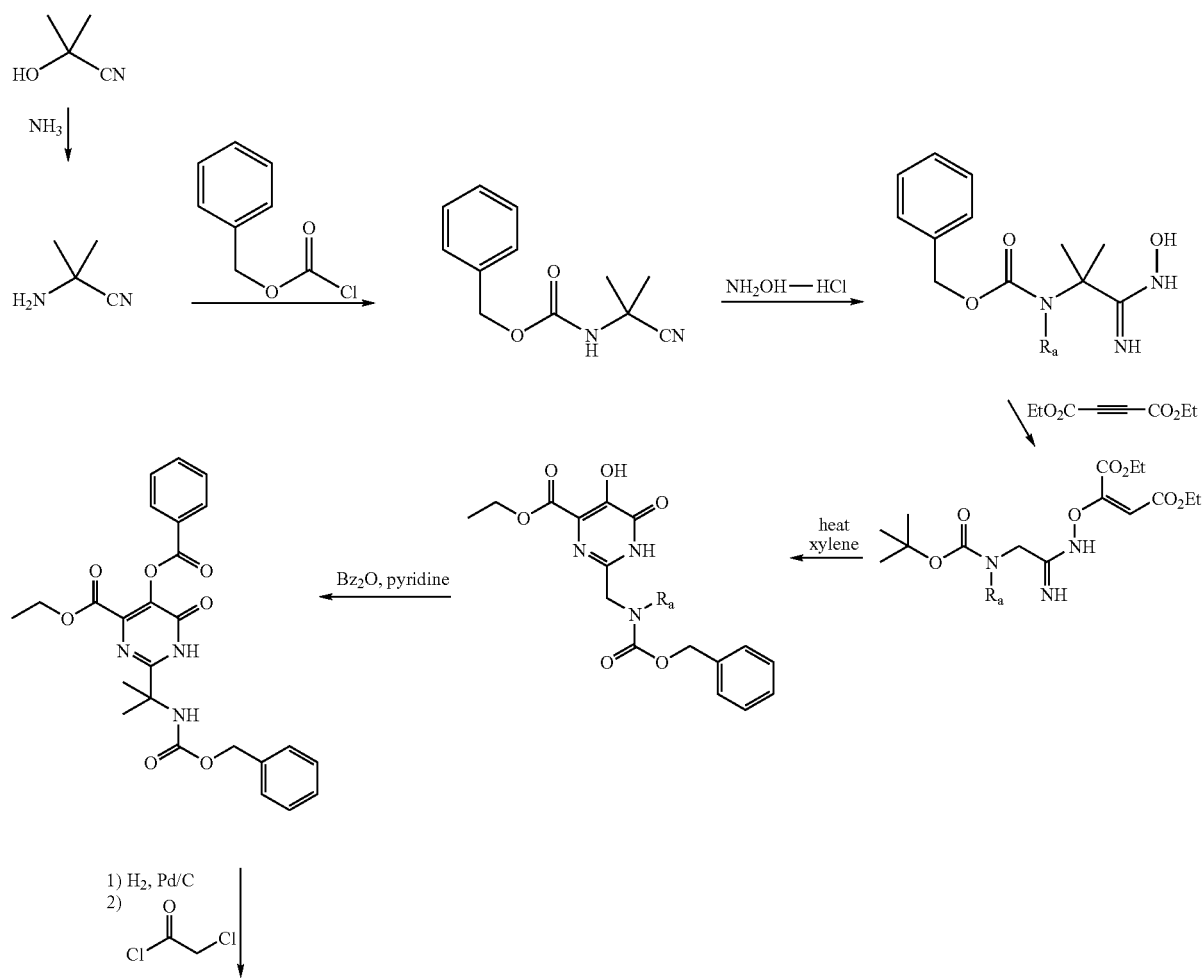
Scheme XI

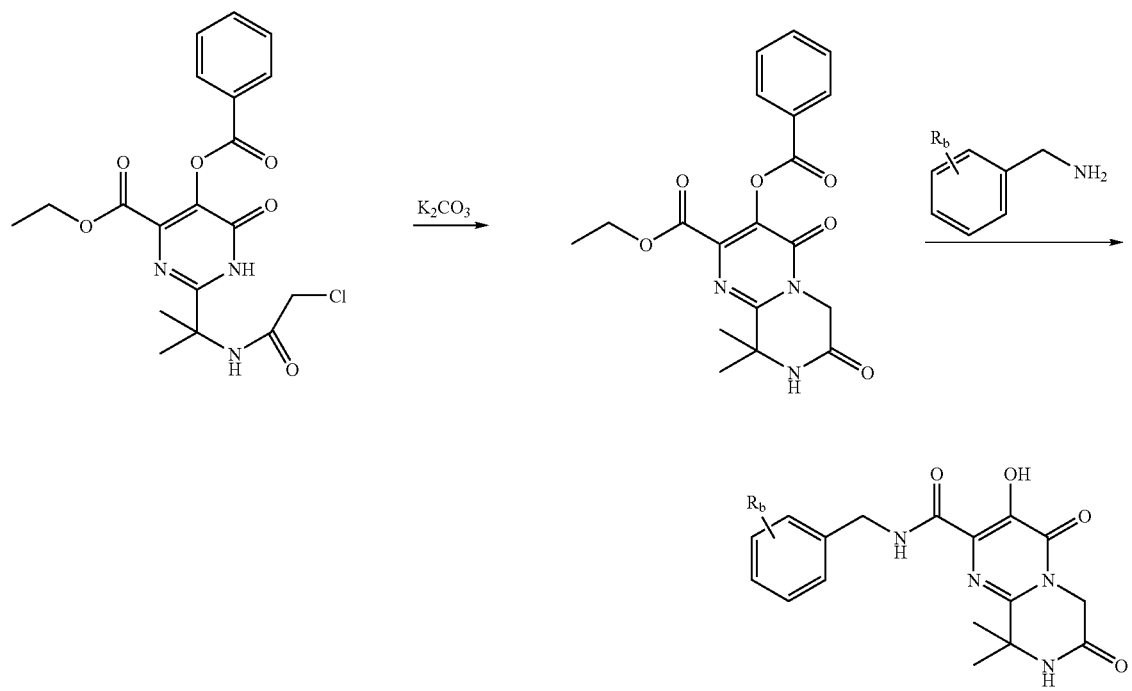
Scheme XII
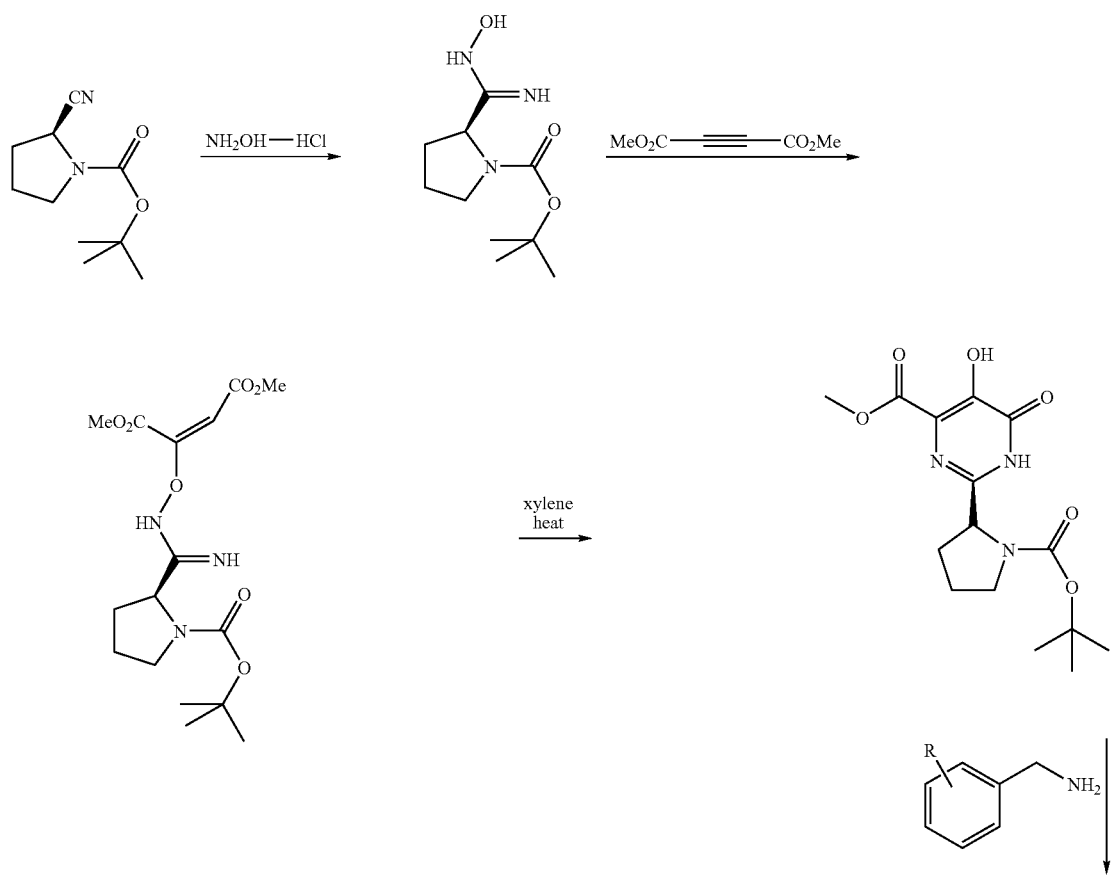

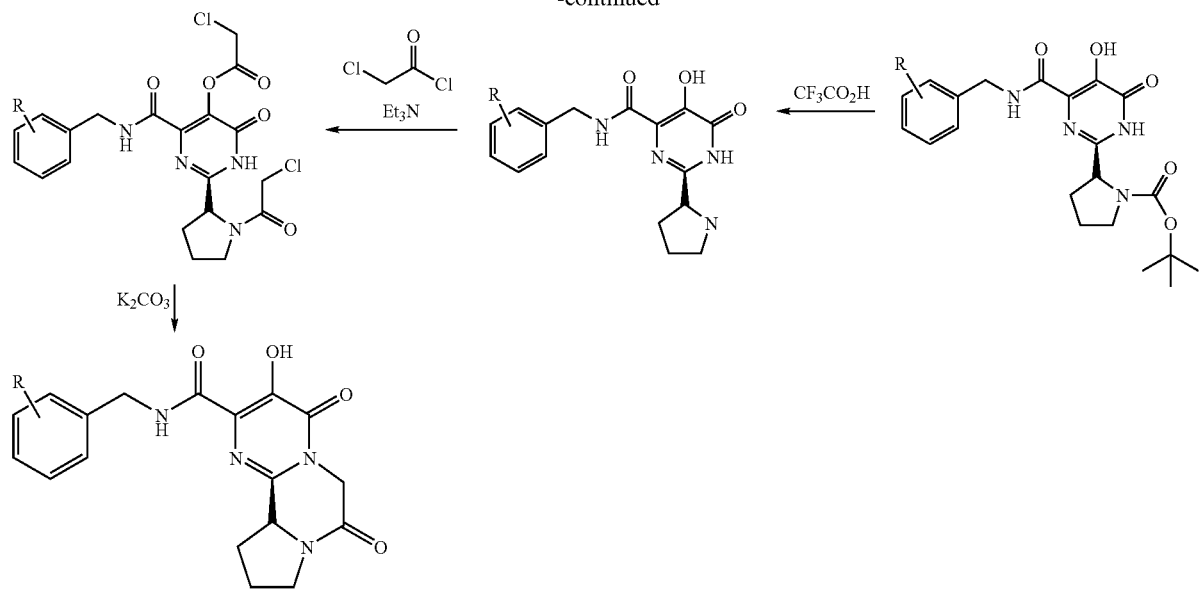

Biological Methods

Another aspect of the invention is a method for inhibiting HIV integrase comprising contacting a compound of Formula I with HIV integrase.

Another aspect of the invention is a method for inhibiting HIV viral DNA integration into human DNA comprising administering an effective amount of a compound of Formula I to a human cell infected with HIV.

HIV-Integrase Inhibition Activity. To evaluate in-vitro activity against HIV-integrase, 5 pmole of biotin labeled substrate DNA was bound to 100 μg of Streptavidin coated PVT SPA beads (Amersham Pharmacia Biotech). Recombinant integrase (0.26 ng) was incubated with the beads for 90 min at 37° C. Unbound enzyme was removed by washing the complex followed by addition of inhibitors and 0.1 fmol of P33 labeled target DNA. The reaction was stopped by adding EDTA to a final concentration of 10 nM. Samples were counted in TopCountNXT (Packard) and the CPM was used as a measure of integration. The reaction condition was as described in A. Engelman and R. Craigie, *J. Virol.* 69, 5908–5911 (1995). The sequences of substrate and target DNA were described in *Nucleic Acid Research* 22, 1121–1122 (1994). Results are shown in the Table 1. Activity equal to A refers to a compound having $IC_{50}$=0.004 to 0.015 μM while B and C denote compounds having $IC_{50}$=0.016 to 049 μM and $IC_{50} \geq 0.05$ μM respectively.

TABLE 1

| Example | Activity |
|---------|----------|
| 1 | C |
| 2 | A |
| 3 | B |
| 4 | B |
| 5 | B |
| 6 | B |
| 7 | A |
| 8 | A |
| 9 | C |
| 10 | A |

TABLE 1-continued

| Example | Activity |
|---------|----------|
| 11 | A |
| 12 | B |
| 13 | B |
| 14 | B |
| 15 | B |
| 16 | B |
| 17 | C |
| 18 | B |
| 19 | A |
| 20 | A |
| 21 | A |
| 22 | B |
| 23 | A |
| 24 | C |
| 25 | B |
| 26 | B |
| 27 | B |
| 28 | B |
| 29 | C |
| 30 | C |
| 31 | A |
| 32 | A |
| 33 | B |
| 34 | B |
| 35 | A |
| 36 | A |
| 37 | A |
| 38 | A |
| 39 | B |
| 40 | B |
| 41 | C |
| 42 | C |
| 43 | C |
| 44 | C |
| 45 | B |
| 46 | C |

Inhibition of HIV replication. A recombinant NL-Rluc virus was constructed in which a section of the nef gene from NL4-3 was replaced with the *Renilla* Luciferase gene. The NL-RLuc virus was prepared by co-transfection of two plasmids, pNLRLuc and pVSVenv. The pNLRLuc contains the NL-Rluc DNA cloned into pUC18 at the PvuII site, while the pVSVenv contains the gene for VSV G protein linked to an LTR promoter. Transfections were performed at a 1:3 ratio of pNLRLuc to pVSVenv on 293T cells using the LipofectAMINE PLUS kit from Invitrogen (Carlsbad, Calif.) according to manufactures instruction, and the pseudotype virus generated was titered in MT-2-cells.

Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/\text{drug conc.})^m]$ (Johnson V A, Byington R T. Infectivity Assay. In *Techniques in HIV Research*. ed. Aldovini A, Walker B D. 71–76. New York: Stockton Press. 1990). The anti-viral activity of compounds was evaluated under three serum conditions, 10% FBS, 15 mg/ml human serum albumin/10% FBS or 40% human serum/5% FBS, and the results from at least 2 experiments were used to calcualte the $EC_{50}$ values. Results are shown in the Table 2. Activity equal to A refers to a compound having $EC_{50}$=0.016 to 0.24 µM while B and C denote compounds with $EC_{50}$=0.25 to 0.9 µM and $EC_{50} \geq 1.0$ µM respectively.

TABLE 2

| Example | Activity |
|---------|----------|
| 1 | B |
| 2 | C |
| 3 | B |
| 4 | C |
| 5 | B |
| 6 | C |
| 7 | A |
| 8 | B |
| 9 | B |
| 10 | A |
| 11 | A |
| 12 | A |
| 13 | A |
| 14 | C |
| 15 | B |
| 16 | B |
| 17 | C |
| 18 | A |
| 19 | A |
| 20 | A |
| 21 | A |
| 22 | A |
| 23 | C |
| 24 | C |
| 25 | C |
| 26 | C |
| 27 | B |
| 28 | B |
| 29 | C |
| 30 | C |
| 31 | C |
| 32 | A |
| 33 | B |
| 34 | B |
| 35 | A |
| 36 | B |
| 37 | A |
| 38 | A |
| 39 | A |
| 40 | C |
| 41 | B |
| 42 | B |
| 43 | C |
| 44 | C |
| 45 | C |
| 46 | C |

Pharmaceutical Composition and Methods of Use

The compounds of this invention inhibit HIV integrase. HIV integrase inhibitors belonging to a class of diketo acid compounds prevented viral integration and inhibited HIV-1 replication in cells (Hazuda et al. *Science* 2000, 287, 646). Recently, HIV integrase inhibitors have been accepted into clinical trials for treating AIDS and HIV infection (Neamati *Expert. Opin. Ther. Patents* 2002, 12, 709, Pais and Burke *Drugs Fut.* 2002, 27, 1101).

Accordingly, another aspect of the invention is a method for treating HIV infection in a human patient comprising administering a therapeutically effective amount of a compound of Formula I, or a pharmaceutically acceptable salt or solvate thereof, with a pharmaceutically acceptable carrier.

Another aspect of the invention is a method for treating HIV infection in a human patient comprising administering a therapeutically effective amount of a compound of Formula I, or a pharmaceutically acceptable salt or solvate thereof, with a therapeutically effective amount of at least one other agent used for treatment of AIDS or HIV infection. Some suitable agents are nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a composition for treating HIV infection in a human patient comprising administering a therapeutically effective amount of a compound of Formula I, or a pharmaceutically acceptable salt or solvate thereof, with a pharmaceutically acceptable carrier.

"Combination," "coadministration," "concurrent," and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25–1000 mg/unit.

Liquid compositions are usually in dosage unit ranges. Generally, the liquid composition will be in a unit dosage range of 1–100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1–100 mg/mL.

The invention encompasses all conventional modes of administration; oral and parenteral methods are preferred. Generally, the dosing regimen will be similar to other antiretroviral agents used clinically. Typically, the daily dose will be 1–100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1–100 mg/kg body weight daily in conjunction with other agents. The other agents generally will be given in the amounts used therapeutically. The specific dosing regime, however, will be determined by a physician using sound medical judgement.

Table 3 lists some agents useful in treating AIDS and HIV infection which are suitable for this invention.

TABLE 3

| ANTIVIRALS | | |
|---|---|---|
| DRUG NAME | MANUFACTURER | INDICATION |
| 097 (non-nucleoside reverse transcriptase inhibitor) | Hoechst/Bayer | HIV infection, AIDS, ARC |
| Amprenavir 141 W94 GW 141 (protease inhibitor) | Glaxo Wellcome | HIV infection, AIDS, ARC |
| Abacavir (1592U89) GW 1592 (RT inhibitor) | Glaxo Wellcome | HIV infection, AIDS, ARC |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection, ARC, PGL HIV positive, AIDS |
| Alpha Interferon | Glaxo Wellcome | Kaposi's sarcoma |
| HIV in combination w/Retrovir | | |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-232623 (CGP-73547) (protease inhibitor) | Bristol-Myers Squibb/ Novartis | HIV infection, AIDS, ARC |
| BMS-234475 (CGP-61755) (protease inhibitor) | Bristol-Myers Squibb/ Novartis | HIV infection, AIDS, ARC |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral, CMV retinitis |
| Delaviridine (RT inhibitor) | Pharmacia-Upjohn | HIV infection, AIDS, ARC |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 (protease inhibitor) | AVID (Camden, NJ) | HIV infection, AIDS, ARC |
| Efavirenz (DMP 266) (−)6-Chloro-4-(S)-cyclopropylethynyl-4(S)-trifluoro-methyl-1,4-dihydro-2H-3,1-benzoxazin-2-one, STOCRINE (non-nucleoside RT inhibitor) | DuPont Merck | HIV infection, AIDS, ARC |
| EL10 | Elan Corp, PLC (Gainesville, GA) | HIV infection |
| Famciclovir | Smith Kline | herpes zoster, herpes simplex |
| FTC (reverse transcriptase inhibitor) | Emory University | HIV infection, AIDS, ARC |
| GS 840 (reverse transcriptase inhibitor) | Gilead | HIV infection, AIDS, ARC |
| HBY097 (non-nucleoside reverse transcritase inhibitor) | Hoechst Marion Roussel | HIV infection, AIDS, ARC |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |

TABLE 3-continued

| ANTIVIRALS | | | IMMUNOMODULATORS | | |
|---|---|---|---|---|---|
| DRUG NAME | MANUFACTURER | INDICATION | DRUG NAME | MANUFACTURER | INDICATION |
| Interferon alfa-n3 | Interferon Sciences | ARC, AIDS | AS-101 | Wyeth-Ayerst | AIDS |
| Indinavir | Merck | HIV infection, AIDS, ARC, asymptomatic HIV positive, also in combination with AZT/ddI/ddC | Bropirimine | Pharmacia Upjohn | Advanced AIDS |
| | | | Acemannan | Carrington Labs, Inc. (Irving, TX) | AIDS, ARC |
| ISIS 2922 | ISIS Pharmaceuticals | CMV retinitis | CL246,738 | American Cyanamid Lederle Labs | AIDS, Kaposi's sarcoma |
| KNI-272 | Nat'l Cancer Institute | HIV-associated diseases | EL10 | Elan Corp, PLC (Gainesville, GA) | HIV infection |
| Lamivudine, 3TC (reverse transcriptase inhibitor) | Glaxo Wellcome | HIV infection, AIDS, ARC, also with AZT | FP-21399 | Fuki ImmunoPharm | Blocks HIV fusion with CD4+ cells |
| | | | Gamma Interferon | Genentech | ARC, in combination w/TNF (tumor necrosis factor) |
| Lobucavir | Bristol-Myers Squibb | CMV infection | | | |
| Nelfinavir (protease inhibitor) | Agouron Pharmaceuticals | HIV infection, AIDS, ARC | Granulocyte Macrophage Colony Stimulating Factor | Genetics Institute Sandoz | AIDS |
| Nevirapine (RT inhibitor) | Boeheringer Ingleheim | HIV infection, AIDS, ARC | Granulocyte Macrophage Colony Stimulating Factor | Hoechst-Roussel Immunex | AIDS |
| Novapren | Novaferon Labs, Inc. (Akron, OH) | HIV inhibitor | | | |
| Peptide T Octapeptide Sequence | Peninsula Labs (Belmont, CA) | AIDS | Granulocyte Macrophage Colony Stimulating Factor | Schering-Plough | AIDS, combination w/AZT |
| Trisodium Phosphonoformate | Astra Pharm. Products, Inc. | CMV retinitis, HIV infection, other CMV infections | HIV Core Particle Immunostimulant | Rorer | Seropositive HIV |
| PNU-140690 (protease inhibitor) | Pharmacia Upjohn | HIV infection, AIDS, ARC | IL-2 Interleukin-2 | Cetus | AIDS, in combination w/AZT |
| Probucol | Vyrex | HIV infection, AIDS | IL-2 Interleukin-2 | Hoffman-LaRoche Immunex | AIDS, ARC, HIV, in combination w/AZT |
| RBC-CD4 | Sheffield Med. Tech (Houston, TX) | HIV infection, AIDS, ARC | IL-2 Interleukin-2 (aldeslukin) | Chiron | AIDS, increase in CD4 cell counts |
| Ritonavir (protease inhibitor) | Abbott | HIV infection, AIDS, ARC | | | |
| Saquinavir (protease inhibitor) | Hoffmann-LaRoche | HIV infection, AIDS, ARC | Immune Globulin Intravenous (human) | Cutter Biological (Berkeley, CA) | Pediatric AIDS, in combination w/AZT |
| Stavudine; d4T Didehydrodeoxy-thymidine | Bristol-Myers Squibb | HIV infection, AIDS, ARC | IMREG-1 | Imreg (New Orleans, LA) | AIDS, Kaposi's sarcoma, ARC, PGL |
| Valaciclovir | Glaxo Wellcome | Genital HSV & CMVinfections | IMERG-2 | Imreg (New Orleans, LA) | AIDS, Kaposi's sarcoma, ARC, PGL |
| Virazole Ribavirin | Viratek/ICN (Costa Mesa, CA) | asymptomatic HIV-positive, LAS, ARC | Imuthiol Diethyl Dithio Carbamate | Merieux Institute | AIDS, ARC |
| VX-478 | Vertex | HIV infection, AIDS, ARC | Alpha-2 Interferon | Schering Plough | Kaposi's sarcoma w/AZT, AIDS |
| Zalcitabine | Hoffman-LaRoche | HIV infection, AIDS, ARC, with AZT | Methionine-Enkephalin | TNI Pharmaceutical (Chicago, IL) | AIDS, ARC |
| Zidovudine; AZT | Glaxo Wellcome | HIV infection, AIDS, ARC, Kaposi's sarcoma, in combination with other therapies | MTP-PE Muramyl-Tripeptide Granulocyte Colony Stimulating Factor | Ciba-Geigy Corp. Amgen | Kaposi's sarcoma AIDS, in combination w/AZT |
| Tenofovir disoproxil, fumarate salt (Viread ®) (reverse transcriptase inhibitor) | Gilead | HIV infection, AIDS | Remune | Immune Response Corp. | Immunotherapeutic |
| | | | rCD4 Recombinant Soluble Human CD4 | Genentech | AIDS, ARC |
| Combivir ® (reverse transcriptase inhibitor) | GSK | HIV infection, AIDS | rCD4-IgG hybrids | | AIDS, ARC |
| abacavir succinate (or Ziagen ®) (reverse transcriptase inhibitor) | GSK | HIV infection, AIDS | Recombinant Soluble Human CD4 | Biogen | AIDS, ARC |
| | | | Interferon Alfa 2a | Hoffman-La Roche | Kaposi's sarcoma, AIDS, in combination w/AZT ARC |
| Reyataz ® (atazanavir) | Bristol-Myers Squibb | HIV infection, AIDS | SK&F106528 Soluble T4 | Smith Kline | HIV infection |
| Fuzeon (Enfuvirtide, T-20) | Rocheh/Trimeris | HIV infection, AIDS, viral fusion inhibitor | Thymopentin | Immunobiology Research Institute (Annandale, NJ) | HIV infection |
| Trizivir ® | | HIV infection, AIDS | | | |
| Kaletra ® | Abbott | HIV infection, AIDS, ARC | Tumor Necrosis Factor; TNF | Genentech | ARC, in combination w/gamma Interferon |

| ANTI-INFECTIVES | | |
|---|---|---|
| DRUG NAME | MANUFACTURER | INDICATION |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

DESCRIPTION OF SPECIFIC EMBODIMENTS

Intermediate 1

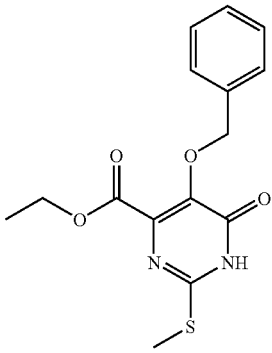

5-Benzyloxy-2-methylsulfanyl-6-oxo-1,6-dihydro-pyrimidine-4-carboxylic acid ethyl ester. A solution of diethyl oxalate (21.06 g, 0.144 mol) and ethyl benzyloxyacetate (28.0 g, 0.144 mol) in dry tetrahydrofuran (200 ml) was treated at 22° C. with sodium hydride (6.34 g of a 60% dispersion in mineral oil, 0.158 mol). Ethanol (0.05 ml) was added and the resulting mixture was stirred at 22° C. for 18 h. The tetrahydrofuran was then evaporated under reduced pressure and the residual orange syrup was dissolved in a solution of sodium ethoxide (0.072 mol prepared from 1.65 g of sodium) in ethanol (200 ml). Powdered 2-methyl-2-thiopseudourea sulfate (20.1 g, 0.072 mol) was added and the resulting mixture was heated at 60° C. for 6 h. Acetic acid (5 ml) was then added to the gel-like reaction mixture and the ethanol was evaporated under reduced pressure. The residual paste was partitioned between water and dichloromethane and the aqueous phase was extracted twice with dichloromethane. The combined organic phases were washed with saturated sodium bicarbonate, brine, dried over anhydrous magnesium sulfate and concentrated under reduced pressure. Chromatography on silica gel (elution with a gradient of ethyl acetate 0–20% in toluene) followed by crystallization from ethyl acetate-hexane gave 8.34 g (18% yield) of the title ester as white needles; mp 109–110° C. $^1$HNMR 400 MHz (CDCl$_3$) δ (ppm): 1.35 (3H, t, J=7.1 Hz, CH$_3$), 2.62 (3H, s, SCH$_3$), 4.37 (2H), q, J=7.1 Hz, CH$_2$), 5.28 (2H, s, OCH$_2$), 7.35–7.52 (5H, m, aromatics), 12.2 (1H, broad s, NH). Anal. Calcd for C$_{15}$H$_{16}$N$_2$O$_4$S: C, 56.23; H, 5.03; N, 8.74. Found: C, 56.23; H, 4.86; N, 8.76.

Intermediate 2

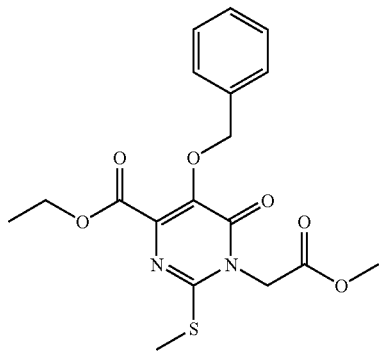

5-Benzyloxy-1-methoxycarbonylmethyl-2-methylsulfanyl-6-oxo-1,6-dihydro-pyrimidine-4-carboxylic acid ethyl ester. A solution of intermediate 1, 5-benzyloxy-2-methylsulfanyl-6-oxo-1,6-dihydro-pyrimidine-4-carboxylic acid ethyl ester, (2.00 g, 6.24 mmol) in dry tetrahydrofuran (100 ml) was treated with methyl bromoacetate (1.05 g, 6.86 mmol) followed by powdered calcium hydride (0.59 g, 14.0 mmol) and the resulting mixture was heated under reflux for 18 h. The reaction mixture was then cooled, quenched by the addition of a few drops of acetic acid and concentrated in vacuo. The residue was then diluted with ethyl acetate, washed successively with saturated sodium bicarbonate and brine then dried over anhydrous magnesium sulfate. Evaporation of the solvent followed by chromatography on silica gel (elution toluene/ethyl acetate 95:5) gave 1.10 g (45% yield) of the title ester as a clear oil. $^1$HNMR 400 MHz (CDCl$_3$) δ (ppm): 1.31 (3H, t, J=7.2 Hz, CH$_3$), 2.60 (3H, s, SCH$_3$), 3.80 (3H, s, OCH$_3$), 4.33 (2H, q, J=7.2 Hz, OCH$_2$), 4.84 (2H, s, NCH$_2$), 5.21 (2H, s, OCH$_2$), 7.3–7.5 (5H, m, aromatics). HRMS (FAB POS) calculated for C$_{18}$H$_{21}$N$_2$O$_6$S [M+H$^+$]: 393.112033. found: 393.112070.

Intermediate 3

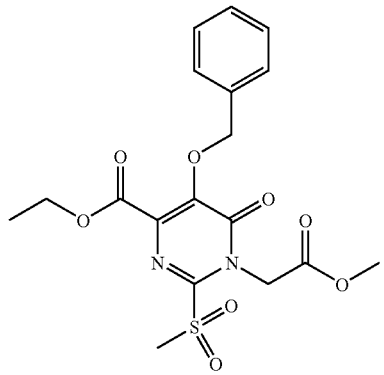

5-Benzyloxy-2-methanesulfonyl-1-methoxycarbonylmethyl-6-oxo-1,6-dihydro-pyrimidine-4-carboxylic acid ethyl ester. A solution of intermediate 2, 5-benzyloxy-1-methoxycarbonylmethyl-2-methylsulfanyl-6-oxo-1,6-dihydro-pyrimidine-4-carboxylic acid ethyl ester, (1.14 g, 2.91 mmol) in dry dichloromethane (40 ml) was treated with 80% 3-chloroperoxybenzoic acid (2.20 g, 10.2 mmol) and the resulting mixture maintained at 35° C. for 1.5 h. The reaction mixture was then diluted with ethyl acetate, washed successively with aqueous sodium bisulphite, saturated sodium bicarbonate and brine then dried over anhydrous magnesium sulfate. Evaporation of the solvent followed by chromatography on silica gel (elution toluene/ethyl acetate 9:1) gave 1.11 g (90% yield) of the title ester as a clear oil. $^1$HNMR 400 MHz (CDCl$_3$) δ (ppm): 1.32 (3H, t, J=7.2 Hz, CH$_3$), 3.46 (3H, s, SO$_2$CH$_3$), 3.84 (3H, s, OCH$_3$), 4.35 (2H, q, J=7.2 Hz, CH$_2$), 5.18 (2H, s, CH$_2$), 5.45 (2H, s, CH$_2$), 7.3–7.5 (5H, m, aromatics). HRMS (FAB POS) calculated for C$_{18}$H$_{21}$N$_2$O$_8$S [M+H$^+$]: 425.101863. found: 425.102626.

Intermediate 4

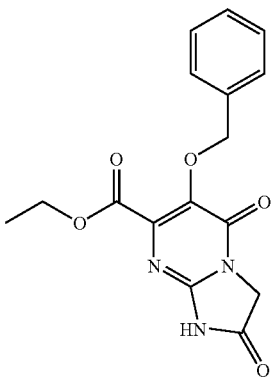

6-Benzyloxy-2,5-dioxo-1,2,3,5-tetrahydro-imidazo[1,2-a]pyrimidine-7-carboxylic acid ethyl ester. A solution of intermediate 3, 5-benzyloxy-2-methanesulfonyl-1-methoxycarbonylmethyl-6-oxo-1,6-dihydro-pyrimidine-4-carboxylic acid ethyl ester, (1.10 g, 2.59 mmol) in acetonitrile (20 ml) was treated with a freshly prepared solution of ammonia in acetonitrile (20 ml) and the resulting mixture stirred at 22° C. for 2 h. The reaction was monitored by LC/MS and rapid formation of the amino intermediate followed by cyclization was observed. The solvent was then evaporated in vacuo and the residue was diluted with ethyl acetate, washed successively with saturated sodium bicarbonate and brine then dried over anhydrous magnesium sulfate. Evaporation of the solvent followed by recrystallization of the solid residue from ethyl acetate/hexane gave 0.770 g (82% yield) of the title ester as white crystals; mp 196° C. $^1$HNMR 400 MHz (CDCl$_3$) δ (ppm): 1.33 (3H, t, J=7.2 Hz, CH$_3$), 4.39 (2H, q, J=7.2 Hz, OCH$_2$), 4.57 (2H, s, CH$_2$), 5.24 (2H, s, OCH$_2$), 7.3–7.55 (5H, m, aromatics), 9.6 (1H, broad, NH). Anal. Calcd for C$_{16}$H$_{15}$N$_3$O$_5$: C, 58.35; H, 4.59; N, 12.76. Found: C, 57.99; H, 4.27, N, 12.62.

Intermediate 5

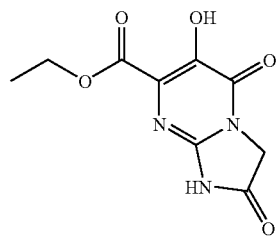

6-Hydroxy-2,5-dioxo-1,2,3,5-tetrahydro-imidazo[1,2-a]pyrimidine-7-carboxylic acid ethyl ester. A solution of intermediate 4, 6-benzyloxy-2,5-dioxo-1,2,3,5-tetrahydro-imidazo[1,2-a]pyrimidine-7-carboxylic acid ethyl ester, (0.770 g, 2.34 mmol) in trifluoroacetic acid (20 ml) was stirred at 25° C. for 1 h. The solvent was then evaporated under reduced pressure and residual trifluoroacetic acid removed by azeotropic distillation with toluene in vacuo. Acetic acid (5 ml) was added and the mixture subjected to azeotropic distillation with toluene in vacuo to remove solvent and residual acid. Recrystallization of the solid residue from ethyl acetate gave 0.497 g (88% yield) of the title ester as white crystals; mp 265° C. (dec).

$^1$HNMR 400 MHz (DMSO-d$_6$) δ (ppm): 1.28 (3H, t, J=7.2 Hz, CH$_3$), 4.29 (2H, q, J=7.2 Hz, OCH$_2$), 4.45 (2H, s, CH$_2$), 10.12 (1H, broad, NH), 11.97 (1H, broad, OH); MS (ESI+) m/z 240 (M=H+).

Intermediate 6

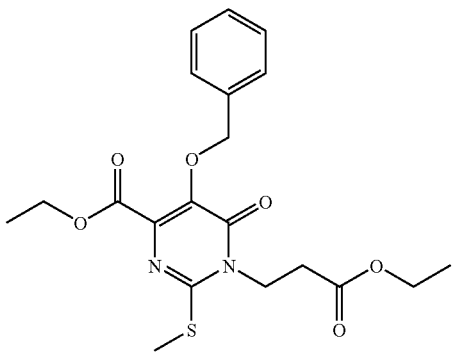

5-Benzyloxy-1-(2-ethoxycarbonyl-ethyl)-2-methylsulanyl-6-oxo-1,6-dihydro-pyrimidine-4-carboxylic acid ethyl ester. A solution of intermediate 1, 5-benzyloxy-2-methylsulfanyl-6-oxo-1,6-dihydro-pyrimidine-4-carboxylic acid ethyl ester (1.00 g, 3.12 mmol) in ethyl acrylate (25 ml) was treated with cesium fluoride (0.12 g) and the resulting mixture was heated under reflux for 8 h. The excess acrylate was then evaporated under reduced pressure and the residue was diluted with ethyl acetate, washed successively with saturated sodium bicarbonate and brine then dried over anhydrous magnesium sulfate. Evaporation of the solvent followed by chromatography on silica gel (elution toluene/ethyl acetate 9:1) gave 1.08 g (82% yield) of the title ester as a clear oil. $^1$HNMR 400 MHz (CDCl$_3$) δ (ppm): 1.30 (3H, t, J=7.1 Hz, CH$_3$), 1.33 (3H, t, J=7.1 Hz, CH$_3$), 2.61 (3H, s, SCH$_3$), 2.79 (2H, m, CH$_2$), 4.20 (2H, q, J=7.1 Hz, OCH$_2$), 4.35 (2H, q, J=7.1 Hz, OCH$_2$), 438 (2H, m, CH$_2$), 5.22 (2H, s, OCH$_2$), 7.3–7.5 (5H, m, aromatics). HRMS (FAB POS) calculated for C$_{20}$H$_{25}$N$_2$O$_6$S [M+H$^+$]: 421.143334. found: 421.143087.

Intermediate 7

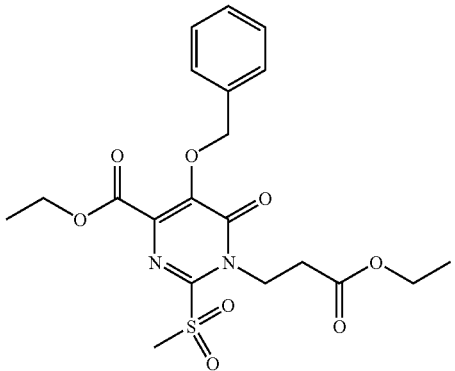

5-Benzyloxy-1-(2-ethoxycarbonyl-ethyl)-2-methanesulfonyl-6-oxo-1,6-dihydro-pyrimidine-4-carboxylic acid ethyl ester. A solution of intermediate 6, 5-benzyloxy-1-(2-ethoxycarbonyl-ethyl)-2-methylsulfanyl-6-oxo-1,6-dihydro-pyrimidine-4-carboxylic acid ethyl ester, (1.247 g, 2.97 mmol) in dry dichloromethane (40 ml) was treated with 80% 3-chloroperoxybenzoic acid (2.20 g 10.2 mmol) as described in the preparation of intermediate 3 to provide 1.260 g (94% yield) of the title ester as a clear oil after chromatography. $^1$HNMR 400 MHz (CDCl$_3$) δ (ppm): 1.30 (3H, t, J=7.1 Hz, CH$_3$), 1.33 (3H, t, J=7.1 Hz, CH$_3$), 2.88 (2H, m, CH$_2$), 3.46 (3H, s, SCH$_3$), 4.20 (2H, q, J=7.1 Hz, OCH$_2$), 4.35 (2H, q, J=7.1 Hz, OCH$_2$), 4.69 (2H, m, CH$_2$), 5.44 (2H, s, OCH$_2$), 7.3–7.5 (5H, m, aromatics). HRMS (FAB POS) calculated for C$_{20}$H$_{25}$N$_2$O$_8$S [M+H$^+$]: 453.133163. found: 453.132474.

Intermediate 8

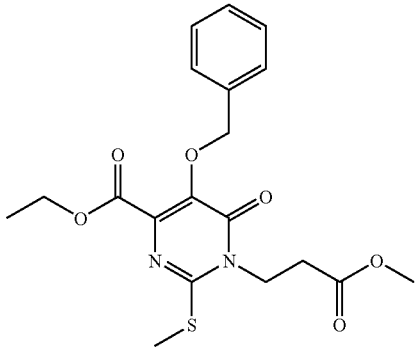

Ethyl 5-benzyloxy-1-(2-methoxycarbonylethyl)-2-methylthio-6-oxo-1,6-dihydro-pyrimidine-4-carboxylate. Reaction of intermediate 1, ethyl 5-benzyloxy-2-methylthio-6-oxo-1,6-dihydro-pyrimidine-4-carboxylate, (1.500 g, 4.68 mmol) with methyl acrylate (25 ml) and cesium fluoride (0.19 g) for 18 h as described for the preparation of intermediate 6 gave 1.560 g (82% yield) of the title ester as a white solid; mp 62–63° C. $^1$HNMR 400 MHz (CDCl$_3$) δ (ppm): 1.31 (3H, t, J=7.1 Hz, CH$_3$), 2.59 (3H, s, SCH$_3$), 2.78 (2H, m, CH$_2$), 3.72 (3H, s, OCH$_3$), 4.34 (4H, m, OCH$_2$ and NCH$_2$), 5.19 (2H, s, OCH$_2$), 7.34 (3H, m, aromatics), 7.46 (2H, m, aromatics). MS (ESI$^+$) m/z 407 [M+H$^+$].

Intermediate 9

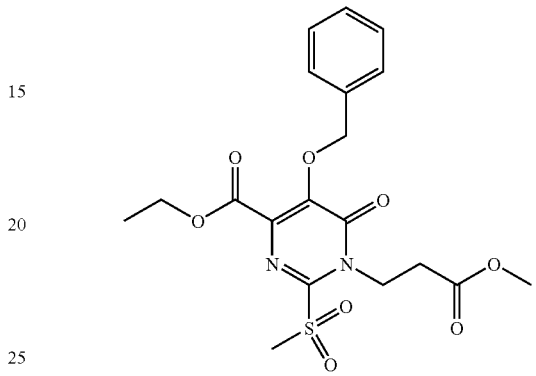

Ethyl 5-benzyloxy-1-(2-methoxycarbonylethyl)-2-methylsulfonyl-6-oxo-1,6-dihydro-pyrimidine-4-carboxylate. Reaction of intermediate 8, ethyl 5-benzyloxy-1-(2-methoxycarbonylethyl)-2-methylthio-6-oxo-1,6-dihydro-pyrimidine-4-carboxylate, (1.710 g, 4.21 mmol) with 80% 3-chloroperoxybenzoic acid (3.20 g, 15 mmol) as described in the preparation of intermediate 3 gave 1.71 g (92% yield) of the title ester as white crystals; mp 64–65° C. $^1$HNMR 400 MHz (CDCl$_3$) δ (ppm): 1.30 (3H, t, J=7.1 Hz, CH$_3$), 2.87 (2H, t, J=7.8 Hz, CH$_2$), 3.44 (3H, s, SCH$_3$), 3.72 (3H, s, OCH$_3$), 4.33 (2H, q, J=7.1 Hz, OCH$_2$), 4.67 (2H, t, J=7.8 Hz, NCH$_2$), 5.42 (2H, s, OCH$_2$), 7.36 (3H, m, aromatics), 7.44 (2H, m, aromatics). Anal. Calcd for C$_{19}$H$_{22}$N$_2$O$_8$S: C, 52.04; H, 5.05; N, 6.38. Found: C, 52.25; H, 4.85; N, 6.29.

Intermediate 10

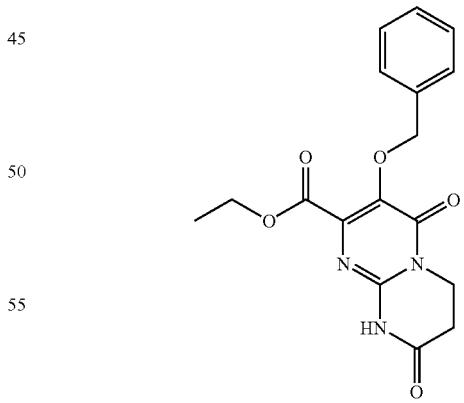

3-Benzyloxy-4,8-dioxo-6,7,8,9-tetrahydro-4H-pyrimido[1,2-a]pyrimidine-2-carboxylic acid ethyl ester. A solution of intermediate 7, 5-benzyloxy-1-(2-ethoxycarbonyl-ethyl)-2-methanesulfonyl-6-oxo-1,6-dihydro-pyrimidine-4-carboxylic acid ethyl ester, (1.220 g, 2.70 mmol) in acetonitrile (20 ml) was treated with a freshly prepared solution of ammonia in acetonitrile (20 ml) and the resulting mixture stirred at 22° C. for 6 h. The solvent was then evaporated in vacuo and the residue was diluted with ethyl acetate, washed successively with saturated sodium bicarbonate and brine then dried over anhydrous magnesium sulfate. Evaporation of the solvent gave 1.06 g of an oil which was dissolved in toluene (25 ml) containing pyridine (0.1 ml) and then heated under reflux for 16 h. The reaction mixture was then diluted with ethyl acetate washed successively with saturated sodium bicarbonate and brine then dried over anhydrous magnesium sulfate. Evaporation of the solvent followed by chromatography on silica gel (elution gradient toluene/ethyl acetate 1:1 to ethyl acetate) gave 0.572 g (61% yield) of the title ester as white crystals; mp 183–184° C. (ethyl acetate). $^1$HNMR 400 MHz (CDCl$_3$) δ (ppm): 1.33 (3H, t, J=7.1 Hz, CH$_3$), 2.83 (2H, t, J=7.0 Hz, CH$_2$), 4.35 (2H, q, J=7.1 Hz, OCH$_2$), 4.36 (2H, t, J=7.0 Hz, CH$_2$), 5.21 (2H, s, OCH$_2$), 7.3–7.55 (5H, m, aromatics), 8.36 (1H, broad s, NH). Anal. Calcd for C$_{17}$H$_{17}$N$_3$O$_5$: C, 59.47; H, 4.99; N 12.24. Found: C, 59.48; H, 5.07; N, 12.16. HRMS (FAB POS) calculated for C$_{17}$H$_{18}$N$_3$O$_5$ [M+H$^+$]: 344.124646. found: 344.124245.

Intermediate 11 intermediate 3, ethyl 5-(benzyloxy)-1-(methoxycarbonylmethyl)-2-(methylsulfonyl)-6-oxo-1,6-dihydropyrimidine-4-carboxylate, (0.790 g, 1.86 mmol) in tetrahydrofuran (10 ml) was treated with a 2 M solution of methylamine in tetrahydrofuiran (10 ml, 20.0 mmol) and the resulting mixture was stirred at 22° C. for 1 h. The solvent was then evaporated in vacuo and the residue was diluted with ethyl acetate, washed successively with saturated sodium bicarbonate, brine and dried over anhydrous magnesium sulfate. Evaporation of the solvent followed by recrystallization of the solid residue from ethyl acetate/hexane gave 0.705 g (83% yield) of the title ester as white crystals; mp 167° C. $^1$HNMR 400 MHz (CDCl$_3$) δ (ppm): 1.34 (3H, t, J=7.1 Hz, CH$_3$), 3.29 (3H, s, NCH$_3$), 4.37 (2H, q, J=7.2 Hz, OCH$_2$), 4.55 (2H, s, CH$_2$), 5.23 (2H, s, OCH$_2$), 7.3–7.5 (5H, m, aromatics). Anal. Calcd for C$_{17}$H$_{17}$N$_3$O$_5$: C, 59.47; H, 4.99; N, 12.23. Found: C, 59.5, H, 5.07; N, 12.40.

Intermediate 13

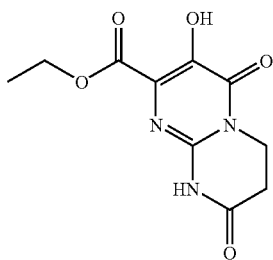

3-Hydroxy-4,8-dioxo-6,7,8,9-tetrahydro-4H-pyrimido[1,2-a]pyrimidine-2-carboxylic acid ethyl ester. Reaction of intermediate 10, 3-benzyloxy-4,8-dioxo-6,7,8,9-tetrahydro-4H-pyrimido[1,2-a]pyrimidine-2-carboxylic acid ethyl ester, (0.543 g, 1.58 mmol) with trifluoroacetic acid (20 ml) as described in the preparation of intermediate 5 gave 0.296 g (74% yield) of the title ester as white crystals; mp 282° C. (dec) (ethyl acetate). $^1$HNMR 400 MHz (DMSO-d$_6$) δ (ppm): 1.26 (3H, t, J=7.1 Hz, CH$_3$), 2.66 (2H, t, J=6.8 Hz, CH$_2$), 4.13 (2H, t, J=6.8 Hz, CH$_2$), 4.29 (2H, q, J=7.1 Hz, OCH$_2$), 9.94 (1H, s, NH), 11.19 (1H, broad s, OH). HRMS (FAB POS) calculated for C$_{10}$H$_{12}$N$_3$O$_5$ [M+H$^+$]: 254.077696. found: 254.078383.

Intermediate 12

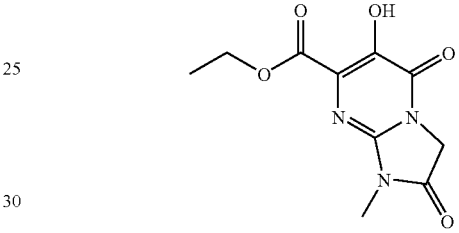

Ethyl 6-hydroxy-1-methyl-2,5-dioxo-1,2,3,5-tetrahydroimidazo[1,2-a]pyrimidine-7-carboxylate. Reaction of intermediate 12, ethyl 6-benzyloxy-1-methyl-2,5-dioxo-1,2,3,5-tetrahydroimidazo[1,2-a]pyrimidine-7-carboxylate, (0.500 g, 1.46 mmol) with trifluoroacetic acid (20 ml) as described in the preparation of intermediate 5 gave 0.308 g (83% yield) of the title ester as white crystals; mp 229–230° C. (ethyl acetate). $^1$HNMR 400 MHz (CDCl$_3$) δ (ppm): 1.49 (3H, t, J=7.1 Hz, CH$_3$), 3.31 (3H, s, NCH$_3$), 4.51 (2H, q, J=7.2 Hz, OCH$_2$), 4.55 (2H, s, CH$_2$), 10.84 (2H, s, OH). Anal. Calcd for C$_{10}$H$_{11}$N$_3$O$_5$: C, 47.43; H, 4.37; N, 16.59. Found: C, 47.22; H, 4.13; N, 16.48.

Intermediate 14

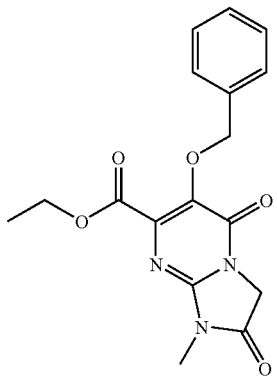

Ethyl 6-benzyloxy-1-methyl-2,5-dioxo-1,2,3,5-tetrahydroimidazo[1,2-a]pyrimidine-7-carboxylate. A solution of

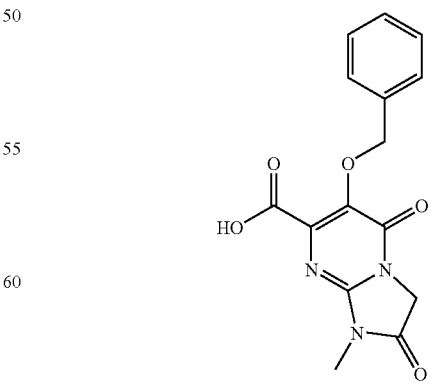

6-Benzyloxy-1-methyl-2,5-dioxo-1,2,3,5-tetrahydroimidazo[1,2-a]pyrimidine-7-carboxylic acid. A solution of intermediate 12, ethyl 6-benzyloxy-1-methyl-2,5-dioxo-1,2,3,5-tetrahydroimidazo[1,2-a]pyrimidine-7-carboxylate, (0.084 g, 0.24 mmol) in a mixture of ethanol (5 ml) and tetrahydrofuran (5 ml) was treated with 1.0 ml of a 1 M aqueous sodium hydroxide and the resulting mixture was stirred at 25° C. for 30 min. The reaction mixture was then acidified with 1 N hydrochloric acid and extracted with ethyl acetate. The organic phase was washed with brine, dried over anhydrous magnesium sulfate and concentrated to give 0.073 g (95% yield) of the title acid as white crystals; mp 194° C. (ethyl acetate). $^1$HNMR 400 MHz (DMSO-$d_6$) δ (ppm): 3.07 (3H, s, NCH$_3$), 4.54 (2H, s, CH$_2$), 5.04 (2H, s, CH$_2$), 7.3–7.5 (5H, m, aromatics), 13.8 (1H, s, OH). MS (ESI$^+$) m/z 316 [M+H$^+$].

Intermediate 15

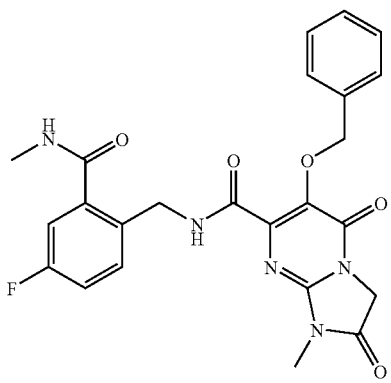

N-{4-Fluoro-2-(methylcarbamoyl)benzyl}-6-benzyloxy-1-methyl-2,5-dioxo-1,2,3,5-tetrahydroimidazo[1,2-a]pyrimidine-7-carboxamide. A mixture of intermediate 14,6-benzyloxy-1-methyl-2,5-dioxo-1,2,3,5-tetrahydroimidazo[1,2-a]pyrimidine-7-carboxylic acid, (0.119 g, 0.38 mmol) and 2-(aminomethyl)-5-fluoro-N-methylbenzamide trifluoroacetate salt (0.123 g, 0.42 mmol) in acetonitrile (20 ml) was treated at 22° C. with triethylamine (0.12 ml, 0.9 mmol) followed by benzotriazole-1-yloxy-tris-pyrrolidino-phosphonium hexafluorophosphate (0.24 g, 0.46 mmol) and the resulting mixture stirred for 2 h. The reaction mixture was then diluted with ethyl acetate, washed with saturated sodium bicarbonate and brine then dried over anhydrous magnesium sulfate. Evaporation of the solvent followed by chromatography of the residue on silica gel (eluted with ethyl acetate) gave 0.119 g (65% yield) of the title amide as white crystals after recrystallization from ethyl acetate; mp 232–233° C. $^1$HNMR 400 MHz (DMSO-$d_6$) δ (ppm): 2.78 (3H, d, J=4.5 Hz, NCH$_3$), 3.11 (3H, s, NCH$_3$), 4.50 (2H, d, J=6.1 Hz, NCH$_2$), 4.56 (2H, s, CH$_2$), 5.04 (2H, s, CH$_2$), 7.08 (1H, m, aromatic), 7.26 (1H, m, aromatic), 7.3–7.5 (6H, m, aromatics), 8.5 (1H, broad q, NH), 8.95 (1H, broad t, NH). Anal. Calcd for C$_{24}$H$_{22}$FN$_5$O$_5$: C, 60.12; H, 4.62; N, 14.60. Found: C 59.90, H, 4.50; N, 14.41.

Intermediate 16

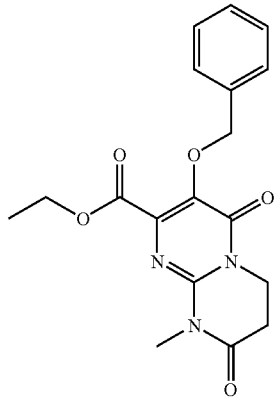

Ethyl 3-benzyloxy-9-methyl-4,8-dioxo-6,7,8,9-tetrahydro-4H-pyrimido[1,2-a]pyrimidine-2-carboxylate. A solution of ethyl intermediate 9, 5-benzyloxy-1-(2-methoxycarbonylethyl)-2-methylsulfonyl-6-oxo-1,6-dihydro-pyrimidine-4-carboxylate, (0.594 g, 1.35 mmol) in tetrahydrofuran (10 ml) was treated with 10 ml (20 mmol) of a 2M solution of methylamine in tetrahydrofuran and the resulting mixture stirred at 22° C. for 1 h. The solvent was then evaporated in vacuo and the residue diluted with toluene and heated under reflux for 2.5 h. The reaction mixture was then diluted with ethyl acetate washed successively with saturated sodium bicarbonate and brine then dried over anhydrous magnesium sulfate. Evaporation of the solvent followed by chromatography on silica gel (elution gradient of ethyl acetate 0–20% in toluene) gave 0.374 g (77% yield) of the title ester as white crystals; mp 121° C. (ethyl acetate/hexane). $^1$HNMR 400 MHz (CDCl$_3$) δ (ppm): 1.31 (3H, t, J=7.1 Hz, CH$_3$), 2.82 (2H, t, J=7.0 Hz, CH$_2$), 3.42 (3H, s, NCH$_3$), 4.27 (2H, t, J=7.0 Hz, CH$_2$), 4.33 (2H, q, J=7.1 Hz, OCH$_2$), 5.20 (2H, s, OCH$_2$), 7.36 (3H, m, aromatics), 7.47 (2H, m, aromatics). Anal. Calcd for C$_{18}$H$_{19}$N$_3$O$_5$: C, 60.49; H, 5.35; N, 11.75. Found: C, 60.12; H, 5.04; N, 11.49.

Intermediate 17

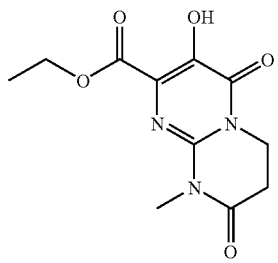

Ethyl 3-hydroxy-9-methyl-4,8-dioxo-6,7,8,9-tetrahydro-4H-pyrimido[1,2-a]pyrimidine-2-carboxylate. Reaction of intermediate 16, ethyl 3-benzyloxy-9-methyl-4,8-dioxo-6,7,8,9-tetrahydro-4H-pyrimido[1,2-a]pyrimidine-2-carboxylate, (0.413 g, 1.16 mmol) with trifluoroacetic acid (20 ml) as described in the preparation of intermediate 5 gave 0.264 g (85% yield) of the title ester as white crystals, mp 182° C. (ethyl acetate/hexane). $^1$HNMR 400 MHz (CDCl$_3$) δ (ppm): 1.44 (3H, t, J=7.1 Hz, CH$_3$), 2.80 (2H, t, J=6.8 Hz, CH$_2$), 3.43 (3H, s, NCH$_3$), 4.28 (2H, t, J=6.8 Hz, CH$_2$), 4.46 (2H, q, J=7.1 Hz, OCH$_2$), 10.48 (1H, s, OH). Anal. Calcd for C$_{11}$H$_{13}$N$_3$O$_5$: C, 49.43; H, 4.90; N, 15.72. Found: C, 49.39; H, 4.89; N, 15.75.

Intermediate 18

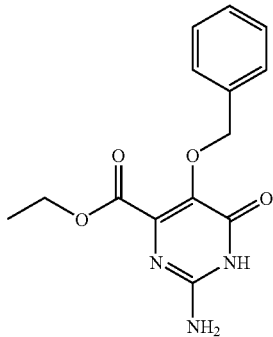

2-Amino-5-benzyloxy-6-oxo-1,6-dihydro-pyrimidine-4-carboxylic acid ethyl ester. A solution of diethyl oxalate (21.06 g, 0.144 mol) and ethyl benzyloxyacetate (28.0 g, 0.144 mol) in dry tetrahydrofuran (200 ml) was treated at 22° C. with sodium hydride (6.34 g of a 60% dispersion in mineral oil, 0.158 mol). Ethanol (0.05 ml) was added and the resulting mixture stirred at 22° C. for 18 h. The tetrahydrofuran was then evaporated under reduced pressure and the residual orange syrup dissolved in a solution of sodium ethoxide (0.144 mol, prepared from 3.31 g of sodium) in ethanol (200 ml). Guanidine hydrochloride (14.6 g, 0.153 mol) was added and the resulting mixture heated at 60° C. for 7 h. Acetic acid (3 ml) was then added to the gel-like reaction mixture and the ethanol was removed under reduced pressure. The residual paste was triturated with a mixture of ethyl alcohol and dichloromethane (1:4), filtered and the filtrate concentrated under reduced pressure. Chromatography of the residue on silica gel (elution with a gradient of ethyl alcohol 0–15% in dichloromethane) followed by recrystallization from 1,2-dichloroethane gave 2.00 g (5% yield) of the title ester as a yellow solid. $^1$HNMR 400 MHz (DMSO-d$_6$) δ (ppm): 1.18 (3H, t, J=7.0 Hz, CH$_3$), 4.17 (2H, q, J=7.0 Hz, CH$_2$), 4.90 (2H, s, OCH$_2$), 6.55 (2H, broad s, NH$_2$), 7.3–7.4 (5H, m, aromatics), 11.4 (1H, broad s, NH). Anal. Calcd for C$_{14}$H$_{15}$N$_3$O$_4$: C, 58.12; H, 5.22; N, 14.52. Found: C, 57.94; H, 5.11; N, 14.58.

Intermediate 19

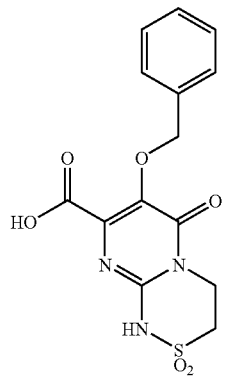

7-Benzyloxy-2,2,6-trioxo-1,3,4,6-tetrahydro-2H-2λ$^6$-pyrimido[2,1-c][1,2,4]thiadiazine-8-carboxylic acid. A solution of intermediate 18, 2-amino-5-benzyloxy-6-oxo-1,6-dihydro-pyrimidine-4-carboxylic acid ethyl ester, (0.125 g, 0.43 mmol) in dry 1-methyl-2-pyrrolidinone (2.5 ml) was treated at 10° C. with sodium hydride (0.040 g of a 60% dispersion in mineral oil, 1.0 mmol) and the resulting mixture stirred for 10 min. The mixture was cooled to 5° C. and 2-chloro-1-ethane sulfonyl chloride (0.077g, 0.47 mmol) was added dropwise. The mixture was stirred 2.5 h while the temperature was slowly increased to 45° C. The mixture was cooled to 10° C. and treated again as above with a second portion 2-chloro-1-ethane sulfonyl chloride (0.057 g, 0.35 mmol). After 2 h, the reaction mixture was quenched with acetic acid (0.1 ml) and purified on a Shimadzu automated preparative HPLC system (column YMC Pack C-18, 5µ, 20×250 mm, elution gradient acetonitrile-water 0.1% trifluoroacetic acid) to give 0.016 g (10% yield) of the title acid as well as 0.017 g (10% yield) of the corresponding ethyl ester and. $^1$HNMR 400 MHz (DMSO-d$_6$) δ (ppm): 3.32 (2H, broad t, CH$_2$), 4.25 (2H, broad t, CH$_2$), 4.87 (2H, s, OCH$_2$), 7.3–7.5 (5H, m, aromatics). MS (ESI$^+$) m/z 352 [M+H$^+$]. Analytical data for the ethyl ester: $^1$HNMR 400 MHz (DMSO-d$_6$) δ (ppm): 1.19 (3H, t, J=7.1 Hz, CH$_3$), 3.40 (2H, broad t, CH$_2$), 4.20 (2H, q, J=7.1 Hz, OCH$_2$), 4.30 (2H, broad t, CH$_2$), 4.94 (2H, s, OCH$_2$), 7.3–7.5 (5H, m, aromatics). MS (ESI$^+$) m/z 380 [M+H$^+$].

Intermediate 20

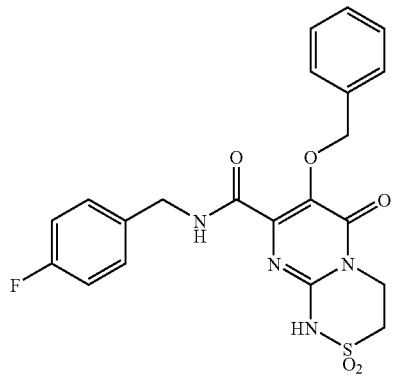

7-Benzyloxy-2,2,6-trioxo-1,3,4,6-tetrahydro-2H-2λ$^6$-pyrimido[2,1-c]thiadiazine-8-carboxylic acid 4-fluoro-benzylamide. A mixture of intermediate 19, 7-benzyloxy-2,2,6-trioxo-1,3,4,6-tetrahydro-2H-2λ$^6$-pyrimido{2,1-c}thiadiazine-8-carboxylic acid (0.017 g, 0.048 mmol) and 4-fluorobenzylamine (0.010 g, 0.08 mmol) in acetonitrile (1.3 ml) was treated at 22° C. with benzotriazole-1-yloxy-tris-pyrrolidino-phosphonium hexafluorophosphate (0.028 g, 0.054 mmol) followed by triethylamine (0.021 ml, 0.15 mmol) and the resulting mixture stirred for 2 h. The reaction mixture was then diluted with dichloromethane, washed with saturated sodium bicarbonate and brine then dried over anhydrous magnesium sulfate. Evaporation of the solvent and chromatography of the residue on silica gel (elution with a gradient of methanol 0–4% in dichloromethane) gave 0.021 g (91% yield) of the title amide as a white solid. $^1$HNMR 400 MHz (DMSO-d$_6$) δ (ppm): 3.33 (2H, m, CH$_2$), 4.29 (2H, broad t, CH$_2$), 4.35 (2H, d, J=6.1 Hz, NCH$_2$), 4.90 (2H, s, OCH$_2$), 7.05 (2H, m, aromatics), 7.29–7.34 (7H, m, aromatics), 9.04 (1H, broad s, NH), 11.95 (1H, broad s, NH).

HRMS (FAB POS) calculated for $C_{21}H_{20}FN_4O_5S$ [M+H$^+$]: 459.113845. found: 459.113652.

Intermediate 21

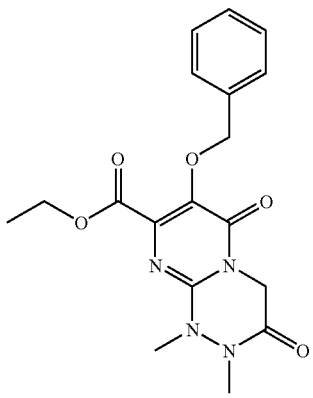

Ethyl 7-benzyloxy-1,2-dimethyl-3,6-dioxo-2,3,4,6-tetrahydro-1H-pyrimido[2,1-c][1,2,4]triazine-8-carboxylate. A mixture of intermediate 3, ethyl 5-benzyloxy-1-(methoxycarbonylmethyl)-2-(methylsulfonyl)-6-oxo-1,6-dihydropyrimidine-4-carboxylate, (0.487 g, 1.15 mmol) in N,N-dimethylformamide (25 ml) was treated with 1,2-dimethylhydrazine dihydrochloride (1.56 g, 11.7 mmol) followed by N,N-diisopropylethylamine (4.1 ml, 11.7 mmol) and the resulting mixture stirred at 22° C. for 4 h. The solvent was then removed in vacuo and the residue diluted with ethyl acetate, washed successively with saturated sodium bicarbonate and brine then dried over anhydrous magnesium sulfate. Evaporation of the solvent followed by chromatography on silica gel (elution with a gradient of ethyl acetate 0–50% in toluene) gave 0.294 g (69% yield) of the title ester as a clear syrup.

$^1$HNMR 400 MHz (CDCl$_3$) δ (ppm): 1.33 (3H, t, J=7.1 Hz, CH$_3$), 3.32 (3H, s, NCH$_3$), 3.44 (3H, s, NCH$_3$), 4.35 (2H, q, J=7.1 Hz, OCH$_2$), 4.65 (2H, s, CH$_2$), 5.19 (2H, s, OCH$_2$), 7.37 (3H, m, aromatics), 7.47 (3H, m, aromatics). MS (ESI$^+$) m/z 373 [M+H$^+$].

Intermediate 22

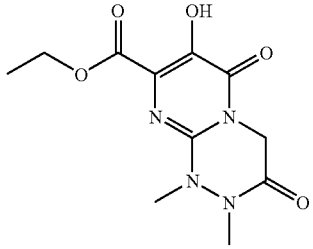

Ethyl 1,2-dimethyl-7-hydroxy-3,6-dioxo-2,3,4,6-tetrahydro-1H-pyrimido[2,1-c][1,2,4]triazine-8-carboxylate. A solution intermediate 21, ethyl 7-benzyloxy-1,2-dimethyl-3,6-dioxo-2,3,4,6-tetrahydro-1H-pyrimido[2,1-c][1,2,4]triazine-8-carboxylate, (0.306 g, 0.82 mmol) in a mixture of ethyl acetate (60 ml) and ethanol (60 ml),at 25° C., over 10% palladium on activated carbon (50 mg) and was treated with 1 atm of hydrogen for 1 h to give 0.226 g (97% yield) of the title amide as a white solid after recrystallization from ethyl acetate. $^1$HNMR 400 MHz (CDCl$_3$) δ (ppm): 1.47 (3H, t, J=7.1 Hz, CH$_3$), 3.28 (3H, s, NCH$_3$), 3.36 (3H, s, NCH$_3$), 4.51 (2H, q, J=7.1 Hz, OCH$_2$), 4.68 (2H, s, CH$_2$), 10.60 (1H, s, OH). MS (ESI$^+$) m/z 283 [M+H$^+$].

Intermediate 23

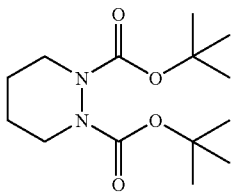

Di-tert-butylpiperazine-1,2-dicarboxylate. (*Bioorg. Med. Chem.*, 11, 2003, 4815–4825) A solution of di-tert-butylhydrazodiformate (5.00 g, 21.5 mmol, Aldrich) in anhydrous DMF (40 mL) was added dropwise to a suspension of sodium hydride (1.75 g, 44 mmol) in anhydrous DMF (20 mL) under a nitrogen atmosphere. The mixture was stirred for 30 minutes then a solution of 1,4-dibromobutane (4.68 g, 21.5 mmol, Aldrich) in anhydrous DMF (10 mL) was added, and the reaction stirred for an additional 16 hours. The solvent was removed in vacuo and the resulting residue dissolved in dichloromethane (50 mL), washed with water (50 mL), dried (magnesium sulfate), filtered, and concentrated to dryness in vacuo. The product was purified by silica gel column chromatography, eluting with 0–10% ether in dichloromethane, to afford 1 (5.22 g, 18.2 mmol, Yield=84.8%) as a white solid. $^1$H NMR (500 MHz, CDCl$_3$) δ ppm: 3.95–4.21 (2H, m), 2.76–3.07 (2H, m), 1.55–168 (4H, m), 1.46 (18H, s). LC/MS m/z 309.06 (M+Na).

Intermediate 24

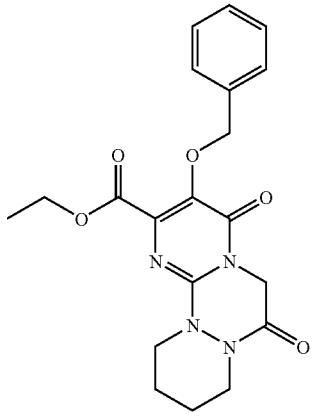

2-Benzyloxy-1,9-dioxo-5,6,7,8,9,10-hexahydro-1H-4,4b,8a,10a-tetraaza-phenanthrene-3-carboxylic acid ethyl ester. A solution of intermediate 23, di-tert-butyl piperazine-1,2-dicarboxylate, (0.862 g, 3.01 mmol) in dichloromethane and trifluoroacetic acid was stirred for 40 minutes. The reaction was concentrated in vacuo to give a glassy solid, which was then dissolved in anhydrous THF (5 mL) and triethylamine (1.0 mL, 7.2 mmol). To the solution was added intermediate 3, 5-benzyloxy-2-methanesulfonyl-1-methoxycarbonylmethyl-6-oxo-1,6-dihydro-pyrimidine-4-carboxylic acid ethyl ester, (0.424 g, 1.00 mmol), and the reaction stirred at 35° C. for 90 minutes. Solvent was removed in vacuo, and the crude product in dichloromethane (20 mL) was washed with 1.0 N HCl (20 mL) then brine (20 mL). The solution was dried (magnesium sulfate), filtered, and concentrated in-vacuo to give the title compound (0.398) as a yellow oil. $^1$H NMR (500 MHz, CDCl$_3$) δ ppm 7.45 (2H, d, J=7.0 Hz), 7.28–7.39 (3H, m), 5.13 (2H, s), 4.60 (2H, s), 4.32 (2H, q, J=7.0 Hz), 3.90–3.96 (2H, m), 3.72–3.77 (2H, m), 1.77–1.92 (4H, m), 1.30 (3H, t, J=7.2 Hz); HRMS (ESI) calcd for C$_{20}$H$_{23}$N$_4$O$_5$ (M+H) 399.1669. found 399.1673.

Intermediate 25

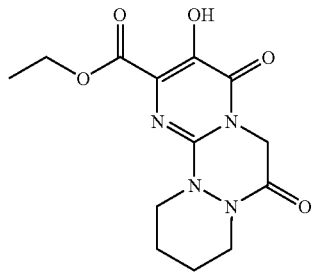

2-Hydroxy-1,9-dioxo-5,6,7,8,9,10-hexahydro-1H-4,4b,8a,10a-tetraaza-phenanthrene-3-carboxylic acid ethyl ester. A solution of intermediate 24, 2-benzyloxy-1,9-dioxo-5,6,7,8,9,10-hexahydro-1H-4,4b,8a, 10a-tetraaza-phenanthrene-3-carboxylic acid ethyl ester (0.396 g, 1.0 mmol) in trifluoroacetic acid (5 mL) was stirred for 18 hours. The reaction was dried in vacuo to give the title compound as an oil which partially crystallized upon standing. $^1$H NMR (500 MHz, CDCl$_3$) δ ppm: 10.35 (1H, br s), 4.63 (2H, s), 4.45 (2H, q, J=7.0 Hz), 3.83–3.88 (2H, m,), 3.72–3,76 (2H, m), 1.90–1.97 (2H, m), 1.76–1.83 (2H, m), 1.43 (3H, t, J=6.7 Hz). HRMS (ESI) calcd for C$_{13}$H$_{17}$N$_4$O$_5$ (M+H) 309.1199. found 309.1207.

Intermediate 26

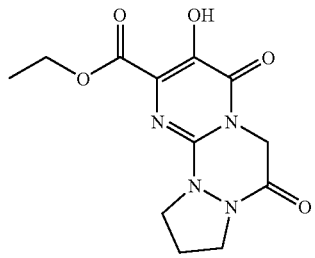

7-Hydroxy-4,6-dioxo-2,3,4,5-tetrahydro-1H,6H-3a,5a,9,9b-tetraaza-benz[e]indene-8-carboxylic acid ethyl ester. $^1$H NMR (500 MHz, CDCl$_3$) δ ppm 4.70 (2H, s), 4.45 (2H, q, J=7.0 Hz), 3.96 (2H, t, J=6.9 Hz), 3.90 (2H, t, J=7.0 Hz), 2.34–2.41 (2H, m), 1.43 (3H, t, J=7.0 Hz). LC/MS m/z 295.25 (M+H)

Intermediate 27

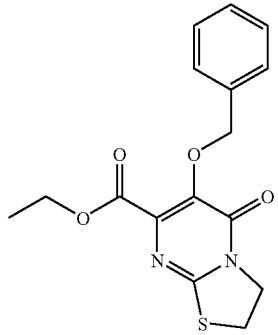

Ethyl 6-(benzyloxy)-5-oxo-3,5-dihydro-2H-thiazolo[3,2-a]pyrimidine-7-carboxylate. Reaction of diethyl oxalate (7.66 g, 52.4 mmol), ethyl benzyloxyacetate (10.2 g, 52.5 mmol) and sodium hydride (2.31 g of a 60% dispersion in mineral oil, 57.9 mmol) with 2-amino-2-thiazoline hydrochloride (7.28 g, 52.5 mmol) as described in intermediate 1 gave 7.99 g (46% yield) of the title ester as white crystals; mp 117 118° C. $^1$HNMR 400 MHz (CDCl$_3$) δ (ppm): 1.32 (3H, t, J=7.1 Hz, CH$_3$), 3.52 (2H, t, J=7.6 Hz, CH$_2$), 4.34 (2H, q, J=7.1 Hz, OCH$_2$), 4.49 (2H, t, J=7.6 Hz, CH$_2$), 5.22 (2H, s, OCH$_2$), 7.3–7.51 (5H, m, aromatics). Anal. Calcd for C$_{16}$H$_{16}$N$_2$O$_4$S: C, 57.81; H, 4.85; N, 8.42. Found: C, 57.78; H, 4.76; N, 8.30.

Intermediate 28

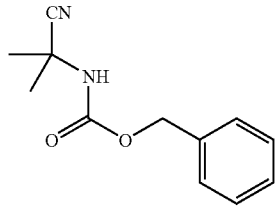

Benzyl 2-cyanopropan-2-ylcarbamate. Acetone cyanohydrin (17 grams, 200 mmol) was added to 400 mL of a 2M solution of NH$_3$ in methanol and the resulting mixture stirred under N$_2$ for 4 days. The solvent was removed in vacuo and the remaining residue dissolved in 250 mL of H$_2$O. After cooling to 10° C., the solution was treated with Na$_2$CO$_3$ (21 grams, 200 mmol) and 95% benzyloxy chloroformate (33 mL, 230 mmol) and stirring continued overnight. Ethyl acetate was added and the mixture transferred to a seperatory funnel. The aqueous layer was removed and the ethyl acetate solution washed with saturated NaHCO$_3$. After drying over Na$_2$SO$_4$ the solvent was removed to yield a solid which was triturated with hexanes to provide the title compound.

Intermediate 29

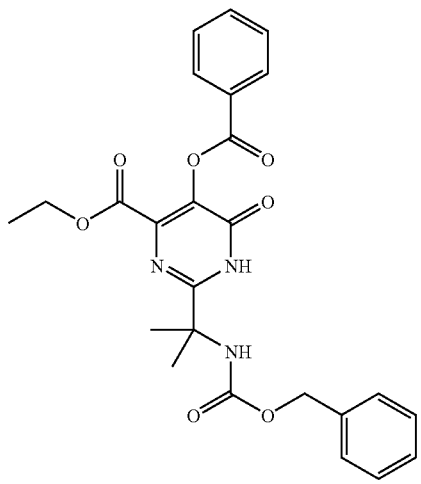

Ethyl 5-(benzoyloxy)-2-(2-(benzyloxycarbonyl)propan-2-yl)-6-oxo-1,6-dihydropyrimidine-4-carboxylate. Intermediate 28, benzyl 2-cyanopropan-2-ylcarbamate, (200 mmol) was added to a solution of $NH_2OH$ (220 mmol) in 300 mL of $CH_3OH$ and stirred overnight at 60° C. The reaction mixture was concentrated in vacuo and the resulting solid isolated by filtration. The solid was dissolved in 300 mL of $CH_2Cl_2$ and treated with diethyl but-2-ynedioate (38.4 mL, 240 mmol) and the resulting solution heated at reflux overnight. The solvent was then removed in vacuo and the remaining residue taken up into xylene and heated to reflux for 50 hours. Upon cooling to room temperature the solvent was removed in vacuo, the remaining oil washed with hexanes then taken up into 300 mL of ether. After sitting in the freezer overnight and returning to room temperature, a precipitate slowly formed. The solid (9 grams, 24 mmol) was isolated by filtration and dissolved in 60 mL of pyridine. To this was added benzoic anhydride (6.5 grams, 29 mmol) and the resulting solution stirred overnight. The reaction mixture was transferred to a seperatory funnel, diluted with ethyl acetate and washed with 1 N HCl followed by 1H NaOH. After drying over $Na_2SO_4$ the solvent was removed to provide the title compound as an amorphous solid. $^1H$ NMR (500 MHz, DMSO-$d_6$) δ ppm: 1.03 (t, 3), 1.56 (s, 6), 4.21 (q, 2), 5.03 (s, 2), 7.32–8.11 (multiplets, 10), 13.17 (s, 1).

Intermediate 30

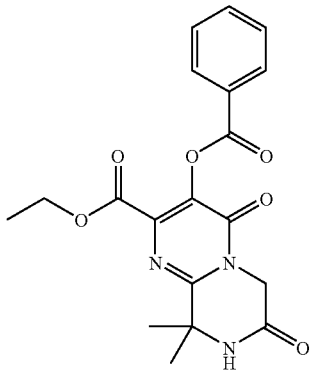

Ethyl 3-(benzoyloxy)-9,9-dimethyl-4,7-dioxo-6,7,8,9-tetrahydro-4H-pyrazino[1,2-a]pyrimidine-2-carboxylate. Intermediate 29, ethyl 5-(benzoyloxy)-2-(2-(benzyloxycarbonyl)propan-2-yl)-6-oxo-1,6-dihydropyrimidine-4-carboxylate, (479 mg, 1 mmol) was dissolved in methanol and treated with $H_2$ (1 atm) over 10% Pd/C (106 mg) for 1 hour. The reaction mixture was filtered through Celite and the solvent removed in vacuo. The remaining residue was dissolved in 2 mL of $CH_2Cl_2$ to which was added iPr$_2$NEt (0.174 mL, 1 mmol) and chloroacetyl chloride (0.080 mL, 1 mmol). The resulting mixture was allowed to stir for 1 hour, then transferred to a seperatory funnel and washed with 1 N HCl. The organic layer was dried ($Na_2SO_4$) and the solvent removed to provide a solid. The solid (1 mmol) was dissolved in 4 mL of DMF. To this was added $K_2CO_3$ (140 mg, 1 mmol) and the resulting solution heated to 70° C. After stirring for 2 hours the reaction was quenched with 1 N HCl and transferred to a seperatory funnel. The mixture was washed with ethyl acetate which was then dried over $Na_2SO_4$. The solvent was removed in vacuo to provide the title compound as an oil.

EXAMPLE 1

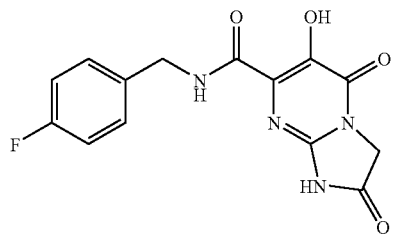

6-Hydroxy-2,5-dioxo-1,2,3,5-tetrahydro-imidazo[1,2-a]pyrimidine-7-carboxylic acid 4-fluoro-benzylamide. A mixture of intermediate 5, 6-hydroxy-2,5-dioxo-1,2,3,5-tetrahydro-imidazo[1,2-a]pyrimidine-7-carboxylic acid ethyl ester, (0.035 g, 0.146 mmol) and 4-fluorobenzylamine (0.11 g, 0.88 mmol) in anhydrous ethyl alcohol (5 ml) and N,N-dimethylformamide (2 ml) was heated under reflux for 18 h. The solvent was then evaporated in vacuo and the residue was partitioned between ethyl acetate and 0.1 N hydrochloric acid. The organic phase was washed with water and brine then dried over anhydrous sodium sulfate. Evaporation of the solvent and recrystallization of the resulting solid from ethanol gave 0.016 g (34% yield) of the title amide as white crystals. $^1$HNMR 400 MHz (DMSO-$d_6$) δ (ppm): 4.46 (4H, broad s, 2×CH$_2$), 7.17 (2H, m, aromatics), 7.36 (2H, m, aromatics), 9.07 (1H, broad t, NH), 11.8–12.4 (2H, broad, OH and NH). MS (ESI$^+$) m/z 319 [M+H$^+$].

EXAMPLE 2

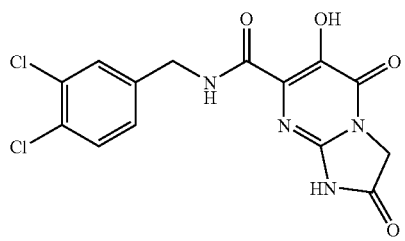

6-Hydroxy-2,5-dioxo-1,2,3,5-tetrahydro-imidazo[1,2-a]pyrimidine-7-carboxylic acid 3,4-dichloro-benzylamide. Reaction of intermediate 5, 6-hydroxy-2,5-dioxo-1,2,3,5-tetrahydro-imidazo[1,2-a]pyrimidine-7-carboxylic acid ethyl ester, (0.075 g, 0.314 mmol) with 3,4-dichlorobenzylamine (0.14 g, 0.79 mmol) as described in the preparation of example 1 gave 0.073 g (63% yield) of the title ester as white crystals; mp 280° C. (dec.) (ethyl acetate). $^1$HNMR 400 MHz (DMSO-$d_6$) δ (ppm): 4.44 (2H, s, $CH_2$), 4.47 (2H, d, J=6.3 Hz, $NCH_2$), 7.31 (1H, dd, J=2.0 Hz and J=8.4 Hz, aromatic), 7.57 (1H, d, J=2.0 Hz, aromatic), 7.61 (1H, d, J=8.4 Hz, aromatic), 9.19 (1H, broad t, NH), 11.8 (2H, broad, OH and NH). HRMS (FAB POS) calculated for $C_{14}H_{11}Cl_2N_4O_4$ [M+H$^+$]: 369.015735. found: 369.015606.

EXAMPLE 3

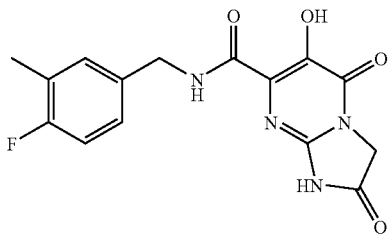

6-Hydroxy-2,5-dioxo-1,2,3,5-tetrahydro-imidazo[1,2-a]pyrimidine-7-carboxylic acid 4-fluoro-3-methyl-benzylamide. Reaction of intermediate 5, 6-hydroxy-2,5-dioxo-1,2,3,5-tetrahydro-imidazo[1,2-a]pyrimidine-7-carboxylic acid ethyl ester, (0.100 g, 0.418 mmol) with 4-fluoro-3-methyl-benzylamine (0.20 g, 1.43 mmol) as described in the preparation of example 1 gave 0.088 g (63% yield) of the title ester as white crystals; mp 287° C. (dec.) (ethyl acetate). $^1$HNMR 400 MHz (DMSO-$d_6$) δ (ppm): 2.21 (3H, d, J=1.7 Hz, $CH_3$), 4.42 (2H, d, J=6.6 Hz, $NCH_2$), 4.45 (2H, s, $CH_2$), 7.09 (1H, m, aromatic), 7.1–7.23 (2H, m, aromatics), 9.0 (1H, broad t, NH), 11.9 and 12.3 (2H, broad, NH and OH). HRMS (FAB POS) calculated for $C_{15}H_{14}FN_4O_4$ [M+H$^+$]: 333.099308. found: 333.099437.

EXAMPLE 4

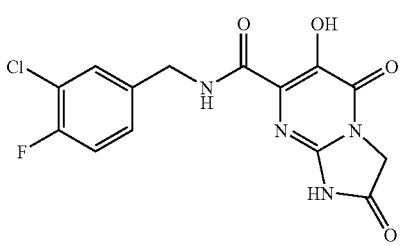

6-Hydroxy-2,5-dioxo-1,2,3,5-tetrahydro-imidazo[1,2-a]pyrimidine-7-carboxylic acid 3-chloro-4-fluoro-benzylamide. Reaction of intermediate 5, 6-hydroxy-2,5-dioxo-1,2,3,5-tetrahydro-imidazo[1,2-a]pyrimidine-7-carboxylic acid ethyl ester (0.075 g, 0.314 mmol) with 3-chloro-4-fluoro-benzylamine (0.15 g, 0.94 mmol) as described in the preparation of example 1 gave 0.040 g (36% yield) of the title ester as white crystals; mp 295° C. (dec.) (ethyl acetate). $^1$HNMR 400 MHz (DMSO-$d_6$) δ (ppm): 4.44 (2H, s, $CH_2$), 4.45 (2H, overlapping d, $NCH_2$), 7.09 (1H, m, aromatic), 7.34 (1H, m, aromatic), 7.37 (1H, m, aromatic), 7.51 (1H, m, aromatic), 9.14 (1H, broad t, NH), 11.9 and 12.1 (2H, broad, NH and OH). HRMS (FAB POS) calculated for $C_{14}H_{11}ClFN_4O_4$ [M+H$^+$]: 353.045286. found: 353.046864.

EXAMPLE 5

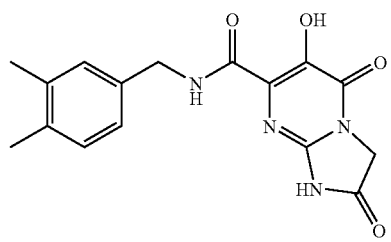

6-Hydroxy-2,5-dioxo-1,2,3,5-tetrahydro-imidazo[1,2-a]pyrimidine-7-carboxylic acid 3,4-dimethyl-benzylamide. Reaction of intermediate 5, 6-hydroxy-2,5-dioxo-1,2,3,5-tetrahydro-imidazo[1,2-a]pyrimidine-7-carboxylic acid ethyl ester (0.075 g, 0.314 mmol) with 3,4-dimethyl-benzylamine (0.15 g, 1.12 mmol) as described in the preparation of example 1 gave 0.059 g (57% yield) of the title ester as white crystals; mp 287° C. (dec.) (ethyl acetate). $^1$HNMR 400 MHz (DMSO-$d_6$) δ (ppm): 2.19 (3H, s, $CH_3$), 2.20 (3H, s, $CH_3$), 4.41 (2H, d, J=6.1 Hz, $NCH_2$), 4.44 (2H, s, $CH_2$), 7.0–7.1 (3H, m, aromatics), 8.92 (1H, broad t, NH), 11.9 and 12.3 (2×1H, broad, NH and OH). HRMS (FAB POS) calculated for $C_{16}H_{16}N_4O_4$ [M$^+$]: 328.117155. found: 328.116571.

EXAMPLE 6

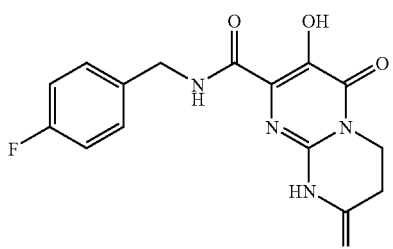

3-Hydroxy-4,8-dioxo-6,7,8,9-tetrahydro-4H-pyrimido[1,2-a]pyrimidine-2-carboxylic acid 4-fluoro-benzylamide. Reaction of intermediate 11, 3-hydroxy-4,8-dioxo-6,7,8,9-tetrahydro-4H-pyrimido[1,2-a]pyrimidine-2-carboxylic acid ethyl ester, (0.075 g, 0.30 mmol) with 4-fluorobenzylamine (0.110 g, 0.88 mmol) as described in the preparation of example 1 gave 0.021 g (21% yield) of the title ester as white crystals: mp >300° C. (dec) (dichloromethane/ethanol)). $^1$HNMR 400 MHz (DMSO-$d_6$) δ (ppm): 2.68 (2H, t, J=6.8 Hz, $CH_2$), 4.12 (2H, t, J=6.8 Hz, $CH_2$), 4.50 (2H, d, J=4.5 Hz, $NCH_2$), 7.18 (2H, m, aromatics), 7.37 (2H, m, aromatics), 8.55 (1H, broad t, NH), 10.96 (1H, broad s, NH), 11.71 (1H, s, OH). HRMS (FAB POS) calculated for $C_{15}H_{14}FN_4O_4$ [M+H$^+$]: 333.099908. found: 333.100065.

EXAMPLE 7

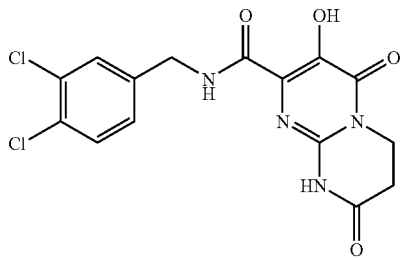

3-Hydroxy-4,8-dioxo-6,7,8,9-tetrahydro-4H-pyrimido[1,2-a]pyrimidine-2-carboxylic acid 3,4-dichloro-benzylamide. Reaction of intermediate 11, 3-hydroxy-4,8-dioxo-6,7,8,9-tetrahydro-4H-pyrimido[1,2-a]pyrimidine-2-carboxylic acid ethyl ester (0.071 g, 0.28 mmol) with 3,4-dichlorobenzylamine (0.14 g, 0.79 mmol) as described in the preparation of example 1 gave 0.060 g (56% yield) of the title ester as white crystals; mp >300° C. (dec.) (dichloromethane/ethanol). $^1$HNMR 400 MHz (DMSO-$d_6$) δ (ppm): 2.69 (2H, t, J=6.8 Hz, CH$_2$), 4.13 (2H, t, J=6.8 Hz, NCH$_2$), 4.51 (2H, d, J=6.3 Hz, NCH$_2$), 7.32 (1H, dd, J=2.0 Hz and J=8.3 Hz, aromatic), 7.58 (1H, d, J=2.0 Hz, aromatic), 7.63 (1H, d, J=8.3 Hz, aromatic), 8.75 (1H, broad t, NH), 10.97 (1H, broad, NH), 11.61 (1H, broad, OH). HRMS (FAB POS) calculated for $C_{15}H_{13}Cl_2N_4O_4$[M+H$^+$]: 383.031386. found: 383.031598.

EXAMPLE 8

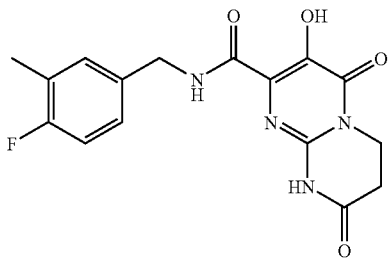

3-Hydroxy-4,8-dioxo-6,7,8,9-tetrahydro-4H-pyrimido[1,2-a]pyrimidine-2-carboxylic acid 4-fluoro-3-methyl-benzylamide. Reaction of intermediate 11, 3-hydroxy-4,8-dioxo-6,7,8,9-tetrahydro-4H-pyrimido[1,2-a]pyrimidine-2-carboxylic acid ethyl ester, (0.075 g, 0.30 mmol) with 4-fluoro-3-methyl-benzylamine (0.15 g, 1.07 mmol) as described in the preparation of example 1 gave 0.063 g (61% yield) of the title ester as white crystals; mp >300° C. (dichloromethane/ethanol). $^1$HNMR 400 MHz (DMSO-$d_6$) δ (ppm): 2.21 (3H, d, J=2.2 Hz, CH$_3$), 2.68 (2H, t, J=6.8 Hz, CH$_2$), 4.12 (2H, t, J=6.8 Hz, NCH$_2$), 4.46 (2H, d, J=6.3 Hz, NCH$_2$), 7.05–7.25 (3H, m, aromatics), 8.50 (1H, broad t, NH), 10.93 (1H, s, NH), 11.71 (1H, s, OH). HRMS (FAB POS) calculated for $C_{16}H_{16}FN_4O_4$ [M+H$^+$]: 347.115558. found: 347.115363.

EXAMPLE 9

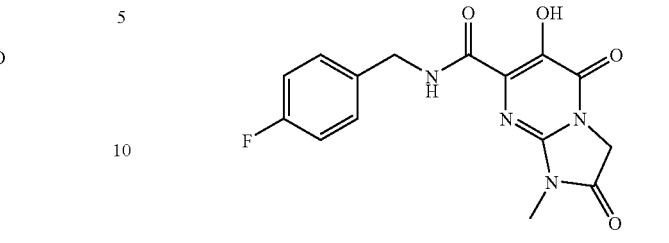

N-(4-Fluorobenzyl)-6-hydroxy-1-methyl-2,5-dioxo-1,2,3,5-tetrahydroimidazo[1,2-a]pyrimidine-7-carboxamide. Reaction of intermediate 13, ethyl 6-hydroxy-1-methyl-2,5-dioxo-1,2,3,5-tetrahydroimidazo[1,2-a]pyrimidine-7-carboxylate (0.050 g, 0.197 mmol) with 4-fluorobenzylamine (0.11 g, 0.87 mmol) as described in the preparation of example 1 gave 0.040 g (60% yield) of the title amide as white crystals. $^1$HNMR 400 MHz (DMSO-$d_6$) δ (ppm): 3.15 (3H, s, NCH$_3$), 4.49 (2H, s, CH$_2$), 4.5 (2H, d, J=6.5 Hz, CH$_2$), 7.18 (2H, m, aromatics), 7.38 (2H, m, aromatics), 9.49 (1H, broad t, NH), 12.28 (1H, s, OH). MS (ESI$^+$) m/z 333 [M+H$^+$].

EXAMPLE 10

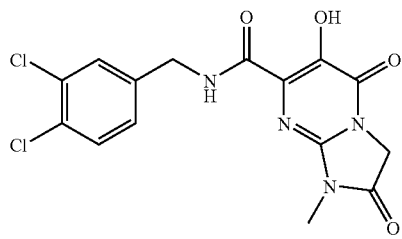

N-(3,4-Dichlorobenzyl)-6-hydroxy-1-methyl-2,5-dioxo-1,2,3,5-tetrahydroimidazo[1,2-a]pyrimidine-7-carboxamide. Reaction of intermediate 13, ethyl 6-hydroxy-1-methyl-2,5-dioxo-1,2,3,5-tetrahydroimidazo[1,2-a]pyrimidine-7-carboxylate, (0.050 g, 0.197 mmol) with 3,4-dichlorobenzylamine (0.11 g, 0.57 mmol) as described in the preparation of example 1 gave 0.045 g (59% yield) of the title amide as a white solid. $^1$HNMR 400 MHz (DMSO-$d_6$) δ (ppm): 3.15 (3H, s, NCH$_3$), 4.48 (2H, s, CH$_2$), 4.50 (2H, d, J=6.9 Hz, NCH$_2$), 7.32 (1H, dd, J=1.4 Hz and J=8.3 Hz, aromatic), 7.58 (1H, d, J=1.4 Hz, aromatic), 7.62 (1H, d, J=8.3 Hz, aromatic), 9.52 (1H, broad t, NH), 12.13 (1H, s, OH). MS (ESI$^+$) m/z 383 [M+H$^+$].

EXAMPLE 11

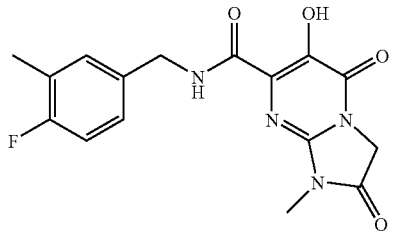

N-(4-Fluoro-3-methylbenzyl)-6-hydroxy-1-methyl-2,5-dioxo-1,2,3,5-tetrahydroimidazo[1,2-a]pyrimidine-7-carboxamide. Reaction of intermediate 13, ethyl 6-hydroxy-1-methyl-2,5-dioxo-1,2,3,5-tetrahydroimidazo[1,2-a]pyrimidine-7-carboxylate (0.050 g, 0.197 mmol) with 4-fluoro-3-methylbenzylamine (0.10 g, 0.72 mmol) as described in the preparation of example 1 gave 0.042 g (61% yield) of the title amide as a white solid. $^1$HNMR 400 MHz (DMSO-d$_6$) δ (ppm): 2.21 (3H, d, J=1.5 Hz, CH$_3$), 3.15 (3H, s, NCH$_3$), 4.45 (2H, d, J=6.6 Hz, NCH$_2$), 4.48 (2H, s, CH$_2$), 7.05–7.25 (3H, m, aromatics), 9.45 (1H, broad t, NH), 12.29 (1H, s, OH). MS (ESI$^+$) m/z 347 [M+H$^+$].

EXAMPLE 12

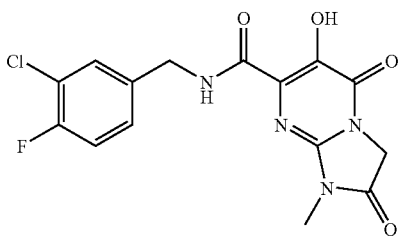

N-(3-Chloro-4-fluorobenzyl)-6-hydroxy-1-methyl-2,5-dioxo-1,2,3,5-tetrahydroimidazo[1,2-a]pyrimidine-7-carboxamide. Reaction of intermediate 13, ethyl 6-hydroxy-1-methyl-2,5-dioxo-1,2,3,5-tetrahydroimidazo[1,2-a]pyrimidine-7-carboxylate (0.050 g, 0.197 mmol) with 3-chloro-4-fluorobenzylamine (0.10 g, 0.63 mmol) as described in the preparation of example 1 gave 0.038 g (52% yield) of the title amide as a white solid. $^1$HNMR 400 MHz (DMSO-d$_6$) δ (ppm): 3.15 (3H, s, NCH$_3$), 4.48 (2H, s, CH$_2$), 4.49 (2H, d, J=6.4 Hz, NCH$_2$), 7.3–7.55 (3H, m, aromatics), 9.50 (1H, broad t, NH), 12.16 (1H, s, OH). MS (ESI$^+$) m/z 367 [M+H$^+$].

EXAMPLE 13

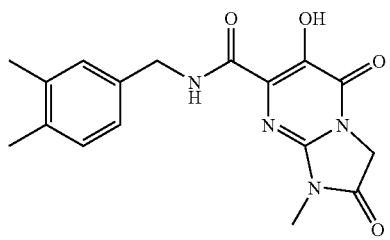

N-(3,4-Dimethylbenzyl)-6-hydroxy-1-methyl-2,5-dioxo-1,2,3,5-tetrahydroimidazo[1,2-a]pyrimidine-7-carboxamide. Reaction of intermediate 13, ethyl 6-hydroxy-1-methyl-2,5-dioxo-1,2,3,5-tetrahydroimidazo[1,2-a]pyrimidine-7-carboxylate (0.070 g, 0.28 mmol) with 3,4-dimethylbenzylamine (0.15 g, 1.12 mmol) as described in the preparation of example 1 gave 0.042 g (58% yield) of the title amide as a white solid. $^1$HNMR 400 MHz (DMSO-d$_6$) δ (ppm): 2.18 (3H, s, CH$_3$), 2.20 (3H, s, CH$_3$), 3.14 (3H, s, NCH$_3$), 4.42 (2H, d, J=6.3 Hz, NCH$_2$), 4.47 (2H, s, CH$_2$), 7.0–7.1 (3H, m, aromatics), 9.40 (1H, broad t, NH), 12.35 (1H, s, OH). MS (ESI$^+$) m/z 343 [M+H$^+$].

EXAMPLE 14

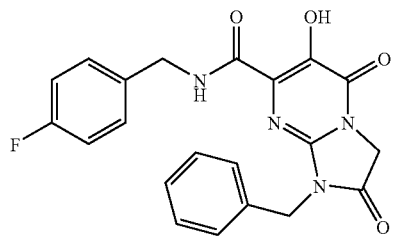

N-(4-Fluorobenzyl)-1-benzyl-6-hydroxy-2,5-dioxo-1,2,3,5-tetrahydroimidazo[1,2-a]pyrimidine-7-carboxamide. $^1$HNMR 400 MHz (DMSO-d$_6$) δ (ppm): 4.51 (2H, d, J=6.5 Hz, NCH$_2$), 4.56 (2H, s, CH$_2$), 4.93 (2H, s, CH$_2$), 719 (2H, m, aromatics), 7.29–7.49 (7H, m, aromatics), 9.49 (1H, broad t, NH), 12.28 (1H, s, OH). HRMS (ESI$^+$) calculated for C$_{21}$H$_{18}$FN$_4$O$_4$ [M+H$^+$]: 409.1312. found: 409.1302.

EXAMPLE 15

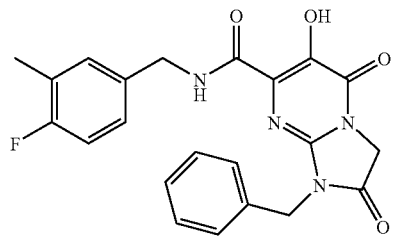

N-(4-Fluoro-3-methylbenzyl)-1-benzyl-6-hydroxy-2,5-dioxo-1,2,3,5-tetrahydroimidazo[1,2-a]pyrimidine-7-carboxamide. $^1$HNMR 400 MHz (CDCl$_3$) δ (ppm): 2.32 (3H, s, CH$_3$), 4.55 (2H, s, CH$_2$), 4.56 (2H, d, J=6.0 Hz, NCH$_2$), 4.86 (2H, s, CH$_2$), 7.04 (1H, m, aromatic), 7.14 (2H, m, aromatics), 7.2–7.34 (5H, m, aromatics), 7.59 (1H, broad t, NH), 12.12 (1H, s, OH). HRMS (ESI$^+$) calculated for C$_{22}$H$_{20}$FN$_4$O$_4$ [M+H$^+$]: 423.1469. found: 423.1451.

EXAMPLE 16

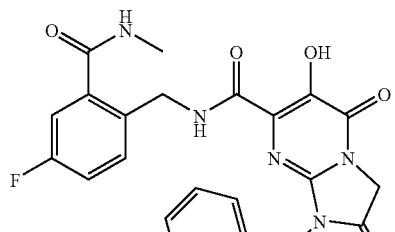

N-(4-Fluoro-2-(methylcarbamoyl)benzyl)-1-benzyl-6-hydroxy-2,5-dioxo-1,2,3,5-tetrahydroimidazo[1,2-a]pyrimidine-7-carboxamide. $^1$HNMR 400 MHz (DMSO-d$_6$) δ (ppm): 2.80 (3H, d, J=4.6 Hz, CH$_3$), 4.56 (2H, s, CH$_2$), 4.57 (2H, d, J=6.6 Hz, NCH$_2$), 4.84 (2H, s, CH$_2$), 7.26–7.41 (6H, m, aromatics), 7.52 (2H, m, aromatics), 8.59 (1H, broad q, NH), 9.41 (1H, broad t, NH), 12.20 (1H, s, OH). HRMS (ESI⁺) calculated for $C_{23}H_{21}FN_5O_5$ [M+H⁺]: 466.1527 . found: 466.1544.

EXAMPLE 17

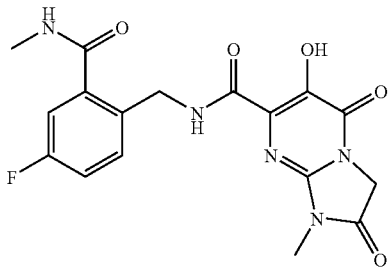

N-{4-Fluoro-2-(methylcarbamoyl)benzyl}-6-hydroxy-1-methyl-2,5-dioxo-1,2,3,5-tetrahydroimidazo[1,2-a]pyrimidine-7-carboxamide. A solution of intermediate 15, N-{4-fluoro-2-(methylcarbamoyl)benzyl}-6-benzyloxy-1-methyl-2,5-dioxo-1,2,3,5-tetrahydroimidazo[1,2-a]pyrimidine-7-carboxamide, (0.179 g, 0.37 mmol) in trifluoroacetic acid (10 ml) was stirred at 22° C. for 2 h. The solvent was then evaporated in vacuo and the residue recrystallized from ethyl acetate to give 0.114 g (78% yield) of the title amide as a white solid. ¹HNMR 400 MHz (DMSO-d₆) δ (ppm): 2.79 (3H, d, J=4.3 Hz, NCH₃), 3.12 (3H, s, NCH₃), 4.48 (2H, s, CH₂), 4.58 (2H, d, J=6.3 Hz, NCH₂), 7.25–7.4 (3H, m, aromatics), 8.55 (1H, broad q, NH), 9.36 (1H, broad t, NH), 12.1 (1H, s, OH). MS (ESI⁺) m/z 390 [M+H⁺].

EXAMPLE 18

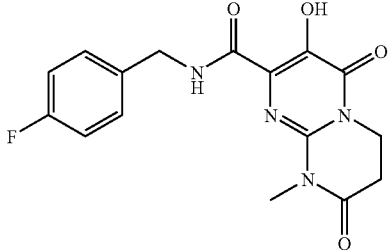

N-(4-Fluorobenzyl)-3-hydroxy-9-methyl-4,8-dioxo-6,7,8,9-tetrahydro-4H-pyrimido[1,2-a]pyrimidine-2-carboxamide. Reaction of intermediate 17, ethyl 3-hydroxy-9-methyl-4,8-dioxo-6,7,8,9-tetrahydro-4H-pyrimido[1,2-a]pyrimidine-2-carboxylate, (0.050 g, 0.187 mmol) with 4-fluorobenzylamine (0.110 g, 0.88 mmol) as described in the preparation of example 1 gave 0.054 g (83% yield) of the title ester as white crystals: mp 176–178° C. (ethyl acetate/hexane). ¹HNMR 400 MHz (CDCl₃) δ (ppm): 2.81 (2H, t, J=6.8 Hz, CH₂), 3.35 (3H, s, NCH₃), 4.29 (2H, t, J=6.8 Hz, CH₂), 4.60 (2H, d, J=6.4 Hz, NCH₂), 7.06 (2H, m, aromatics), 7.3 (2H, m, aromatics), 7.66 (1H, broad t, NH), 11.92 (1H, s, OH). MS (ESI⁺) m/z 347 [M+H⁺]. Anal. Calcd for $C_{16}H_{15}FN_4O_4$: C, 55.49; H, 4.36; N, 16.17. Found: C, 55.39; H, 4.23; N, 15.25.

EXAMPLE 19

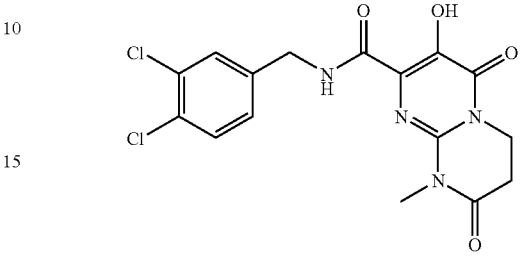

N-(3,4-Dichlorobenzyl)-3-hydroxy-9-methyl-4,8-dioxo-6,7,8,9-tetrahydro-4H-pyrimido[1,2-a]pyrimidine-2-carboxamide. Reaction of intermediate 17, ethyl 3-hydroxy-9-methyl-4,8-dioxo-6,7,8,9-tetrahydro-4H-pyrimido[1,2-a]pyrimidine-2-carboxylate, (0.050 g, 0.187 mmol) with 3,4-dichlorobenzylamine (0.10 g, 0.57 mmol) as described in the preparation of example 1 gave 0.033 g (44% yield) of the title ester as white crystals, mp 198–201° C. (ethyl acetate-hexane). ¹HNMR 400 MHz (CDCl₃) δ (ppm): 2.82 (2H, t, J=6.8 Hz, CH₂), 3.37 (3H, s, NCH₃), 4.29 (2H, t, J=6.8 Hz, NCH₂), 4.59 (2H, d, J=6.7 Hz, NCH₂), 7.18 (1H, dd, J=2.0 Hz and J=8.3 Hz, aromatic), 7.41 (1H, d, J=2.0 Hz, aromatic), 7.44 (1H, d, J=8.3 Hz, aromatic), 7.71 (1H, broad t, NH), 11.78 (1H, s, OH). MS (ESI⁺) m/z 397 [M+H⁺].

EXAMPLE 20

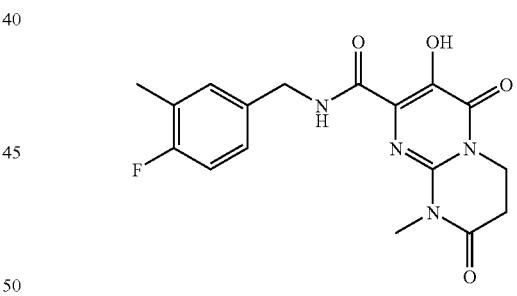

N-(4-Fluoro-3-methylbenzyl)-3-hydroxy-9-methyl-4,8-dioxo-6,7,8,9-tetrahydro-4H-pyrimido[1,2-a]pyrimidine-2-carboxamide. Reaction of intermediate 17, ethyl 3-hydroxy-9-methyl-4,8-dioxo-6,7,8,9-tetrahydro-4H-pyrimido[1,2-a]pyrimidine-2-carboxylate (0.050 g, 0.187 mmol) with 4-fluoro-3-methyl-benzylamine (0.10 g, 0.72 mmol) as described in the preparation of example 1 gave 0.054 g (80% yield) of the title ester as white crystals, mp 216° C. (ethyl acetate/hexane). ¹HNMR 400 MHz (CDCl₃) δ (ppm): 2.27 (3H, d, J=1.6 Hz, CH₃), 2.81 (2H, t, J=6.8 Hz, CH₂), 3.35 (3H, s, NCH₃), 4.29 (2H, t, J=6.8 Hz, NCH₂), 4.55 (2H, d, J=6.4 Hz, NCH₂), 6.99 (1H, m, aromatic), 7.1–7.15 (2H, m, aromatics), 7.64 (1H, broad t, NH), 11.94 (1H, s, OH). Anal. Calcd for $C_{17}H_{17}FN_4O_4$: C, 56.66; H 4.75; N, 15.54. Found: C, 56.42; H, 4.74; N, 15.29.

EXAMPLE 21

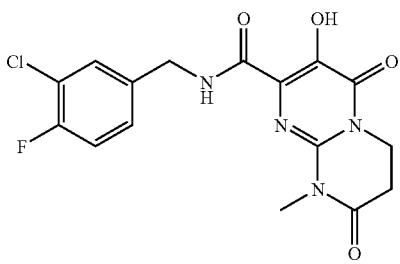

N-(3-Chloro-4-fluorobenzyl)-3-hydroxy-9-methyl-4,8-dioxo-6,7,8,9-tetrahydro-4H-pyrimido[1,2-a]pyrimidine-2-carboxamide. Reaction of intermediate 17, ethyl 3-hydroxy-9-methyl-4,8-dioxo-6,7,8,9-tetrahydro-4H-pyrimido[1,2-a]pyrimidine-2-carboxylate, (0.050 g, 0.187 mmol) with 3-chloro-4-fluorobenzylamine (0.10 g, 0.63 mmol) as described in the preparation of example 1 gave 0.066 g (92% yield) of the title ester as white crystals; mp 201° C. (ethyl acetate/hexane). $^1$HNMR 400 MHz (CDCl$_3$) δ (ppm): 2.84 (2H, t, J=6.8 Hz, CH$_2$), 3.40 (3H, s, NCH$_3$), 4.32 (2H, t, J=6.8 Hz, NCH$_2$), 4.61 (2H, d, J=6.8 Hz, NCH$_2$), 7.16 (1H, m, aromatic), 7.23 (1H, m, aromatic), 7.39 (1H, m, aromatic), 7.72 (1H, broad t, NH), 11.84 (1H, s, OH). MS (ESI$^+$) m/z 381 [M+H$^+$].

EXAMPLE 22

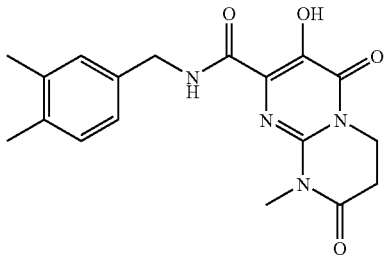

N-(3,4-Dimethylbenzyl)-3-hydroxy-9-methyl-4,8-dioxo-6,7,8,9-tetrahydro-4H-pyrimido[1,2-a]pyrimidine-2-carboxamide. Reaction of intermediate 17, ethyl 3-hydroxy-9-methyl-4,8-dioxo-6,7,8,9-tetrahydro-4H-pyrimido[1,2-a]pyrimidine-2-carboxylate, (0.065 g, 0.243 mmol) with 3,4-dimethylbenzylamine (0.15 g, 1.12 mmol) as described in the preparation of example 1 gave 0.051 g (58% yield) of the title ester as white crystals; mp 181° C. (ethyl acetate/hexane). $^1$HNMR 400 MHz (CDCl$_3$) δ (ppm): 2.28 (3H, s, CH$_3$), 2.29 (3H, s, CH$_3$), 2.83 (2H, t, J=6.8 Hz, CH$_2$), 3.37 (3H, s, NCH$_3$), 4.31 (2H, t, J=6.8 Hz, NCH$_2$), 4.59 (2H, d, J=6.1 Hz, NCH$_2$), 7.07–7,17 (3H, m, aromatics), 7.65 (1H, broad t, NH), 12.05 (1H, s, OH). MS (ESI$^+$) m/z 357 [M+H$^+$].

EXAMPLE 23

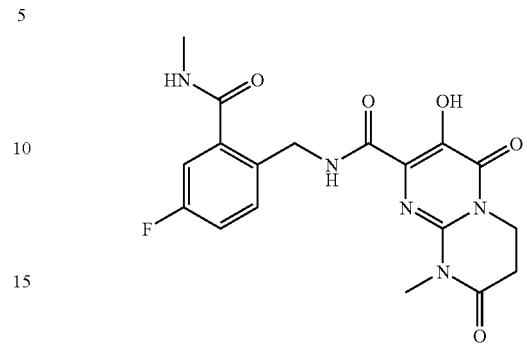

N-(4-Fluoro-2-(methylcarbamoyl)benzyl)-3-hydroxy-9-methyl-4,8-dioxo-6,7,8,9-tetrahydro-4H-pyrimido[1,2-a]pyrimidine-2-carboxamide. $^1$HNMR 400 MHz (DMSO-d$_6$) δ (ppm): 2.75 (2H, m, CH$_2$), 2.77 (3H, d, J=3.2 Hz, NCH$_3$), 3.32 (3H, s, NCH$_3$), 4.09 (2H, m, CH$_2$), 4.55 (2H, d, J=5.6 Hz, NCH$_2$), 7.3–7.4 (3H, m, aromatics), 8.56 (1H, broad, NH), 9.36 (1H, broad, NH), 11.95 (1H, s, OH).

EXAMPLE 24

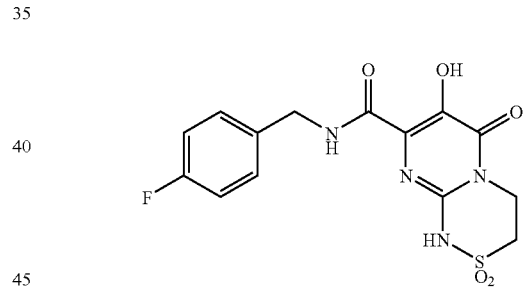

7-Hydroxy-2,2,6-trioxo-1,3,4,6-tetrahydro-2H-2λ$^6$-pyrimido[2,1-c][1,2,4]thiadiazine-8-carboxylic acid 4-fluorobenzylamide. A solution of intermediate 20,7-benzyloxy-2,2,6-trioxo-1,3,4,6-tetrahydro-2H-2λ$^6$-pyrimido{2,1-c}thiadiazine-8-carboxylic acid 4-fluoro-benzylamide, (0.020 g, 0.044 mmol) in trifluoroacetic acid (0.9 ml) and dichloromethane (0.1 ml) was stirred at 40° C. for 7 h. The mixture was diluted with toluene and concentrated in vacuo. The residue was triturated with dichloromethane to give 0.013 g (61% yield) of the title compound as a white solid $^1$HNMR 400 MHz (DMSO-d$_6$) δ (ppm): 3.36 (2H, broad t, J=6.1 Hz, CH$_2$—N), 4.30 (2H, broad t, J=6.1 Hz, CH$_2$—S), 4.47 (2H, d, J=6.1 Hz, CH$_2$—NH), 7.14–7.18 (2H, m, aromatics), 7.34–7.37 (2H, m, aromatics), 8.87 (1H, broad t, J=6.1 Hz, NH), 10.81 (1H, broad s, OH), 11.1 (1H, broad s, NH). HRMS (FAB POS) calculated for C$_{14}$H$_{14}$FN$_4$O$_5$S [M+H$^+$]: 369.066895. found: 369.066380.

EXAMPLE 25

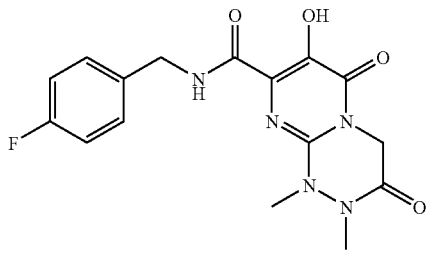

N-(4-Fluorobenzyl)-1,2-dimethyl-7-hydroxy-3,6-dioxo-2,3,4,6-tetrahydro-1H-pyrimido[2,1-c][1,2,4]triazine-8-carboxamide. Reaction of intermediate 22, ethyl 1,2-dimethyl-7-hydroxy-3,6-dioxo-2,3,4,6-tetrahydro-1H-pyrimido[2,1-c][1,2,4]triazine-8-carboxylate, (0.050 g, 0.177 mmol) with 4-fluorobenzylamine (0.11 g, 0.87 mmol) as described in the preparation of example 1 gave 0.051 g (80% yield) of the title amide as white crystals. $^1$HNMR 400 MHz (CDCl$_3$) δ (ppm): 3.27 (3H, s, NCH$_3$), 3.30 (3H, s, NCH$_3$), 4.61 (2H, d, J=6.3 Hz, NCH$_2$), 4.67 (2H, s, CH$_2$), 7.08 (2H, m, aromatics), 7.33 (2H, m, aromatics), 7.74 (1H, broad t, NH), 12.0 (1H, s, OH). MS (ESI$^+$) m/z 362 [M+H$^+$].

EXAMPLE 26

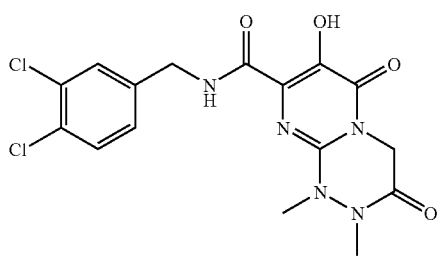

N-(3,4-Dichlorobenzyl)-1,2-dimethyl-7-hydroxy-3,6-dioxo-2,3,4,6-tetrahydro-1H-pyrimido[2,1-c][1,2,4]triazine-8-carboxamide. Reaction of intermediate 22, ethyl 1,2-dimethyl-7-hydroxy-3,6-dioxo-2,3,4,6-tetrahydro-1H-pyrimido[2,1-c][1,2,4]triazine-8-carboxylate, (0.050 g, 0.177 mmol) with 3,4-dichlorobenzylamine (0.10 g, 0.57 mmol) as described in the preparation of example 1 gave 0.054 g (74% yield) of the title amide as a white solid. $^1$HNMR 400 MHz (CDCl$_3$) δ (ppm): 3.28 (3H, s, NCH$_3$), 3.32 (3H, s, NCH$_3$), 4.59 (2H, d, J=6.7 Hz, NCH$_2$), 4.68 (2H, s, CH$_2$), 7.21 (1H, dd, J=2.0 Hz and J=8.0 Hz, aromatic), 7.44 (1H, d, J=2.0 Hz, aromatic), 7.46 (1H, d, J=8.0 Hz, aromatic), 7.78 (1H, broad t, NH), 11.85 (1H, s, OH). MS (ESI$^+$) m/z 413 [M+H$^+$].

EXAMPLE 27

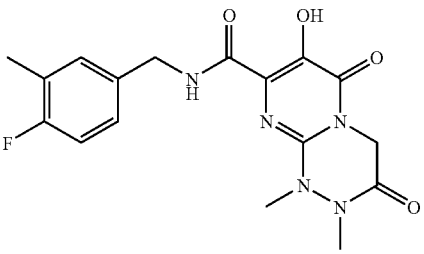

N-(4-Fluoro-3-methylbenzyl)-1,2-dimethyl-7-hydroxy-3,6-dioxo-2,3,4,6-tetrahydro-1H-pyrimido[2,1-c][1,2,4]triazine-8-carboxamide. Reaction of intermediate 22, ethyl 1,2-dimethyl-7-hydroxy-3,6-dioxo-2,3,4,6-tetrahydro-1H-pyrimido[2,1-c][1,2,4]triazine-8-carboxylate, (0.050 g, 0.177 mmol) with 4-fluoro-3-methylbenzylamine (0.10 g, 0.72 mmol) as described in the preparation of example 1 gave 0.053 g (79% yield) of the title amide as white crystals. $^1$HNMR 400 MHz (CDCl$_3$) δ (ppm): 2.31 (3H, s, CH$_3$), 3.27 (3H, s, NCH$_3$), 3.30 (3H, s, NCH$_3$), 4.56 (2H, d, J=5.9 Hz, NCH$_2$), 4.67 (2H, s, CH$_2$), 7.02 (1H, m, aromatic), 7.14 (1H, m, aromatic), 7.17 (1H, m, aromatic), 7.71 (1H, broad t, NH), 12.02 (1H, s, OH). MS (ESI$^+$) m/z 376 [M+H$^+$].

EXAMPLE 28

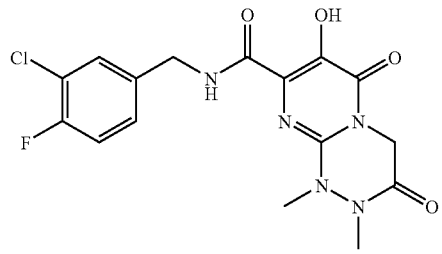

N-(3-Chloro-4-fluorobenzyl)-1,2-dimethyl-7-hydroxy-3,6-dioxo-2,3,4,6-tetrahydro-1H-pyrimido[2,1-c][1,2,4]triazine-8-carboxamide. Reaction of intermediate 22, ethyl 1,2-dimethyl-7-hydroxy-3,6-dioxo-2,3,4,6-tetrahydro-1H-pyrimido[2,1-c][1,2,4]triazine-8-carboxylate (0.070 g, 0.25 mmol) with 3-chloro-4-fluorobebenzylamine (0.14 g, 0.88 mmol) as described in the preparation of example 1 gave 0.052 g (53% yield) of the title amide as a white solid. $^1$HNMR 400 MHz (CDCl$_3$) δ (ppm): 3.28 (3H, s, NCH$_3$), 3.31 (3H, s, NCH$_3$), 4.58 (2H, d, J=6.0 Hz, NCH$_2$), 4.68 (2H, s, CH$_2$), 7.16 (1H, m, aromatic), 7.24 (1H, m, aromatic), 7.40 (1H, m, aromatic), 7.77 (1H, broad t, NH), 11.88 (1H, s, OH). MS (ESI$^+$) m/z 396 [M+H$^+$].

EXAMPLE 29

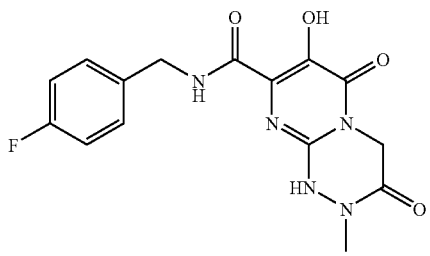

N-(4-Fluorobenzyl)-7-hydroxy-2-methyl-3,6-dioxo-2,3,4,6-tetrahydro-1H-pyrimido[2,1-c][1,2,4]triazine-8-carboxamide. $^1$HNMR 400 MHz (DMSO-$d_6$) δ (ppm): 3.25 (3H, s, NCH$_3$), 4.44 (2H, s, CH$_2$), 4.48 (2H, d, J=5.7 Hz, NCH$_2$), 7.17 (2H, m, aromatics), 7.36 (2H, m, aromatics), 9.37 (1H, broad, NH), 11.2 (1H, broad, NH), 11.8 (1H, broad, OH). HRMS (ESI$^+$) calculated for $C_{15}H_{15}FN_5O_4$ [M+H$^+$]: 348.1108. found: 348.1119.

EXAMPLE 30

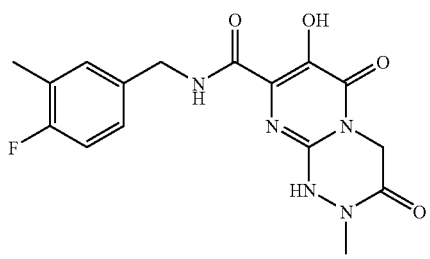

N-(4-Fluoro-3-methylbenzyl)-7-hydroxy-2-methyl-3,6-dioxo-2,3,4,6-tetrahydro-1H-pyrimido[2,1-c][1,2,4]triazine-8-carboxamide. $^1$HNMR 400 MHz (DMSO-$d_6$) δ (ppm): 2.22 (3H, s, CH$_3$), 3.25 (3H, s, NCH$_3$), 4.43 (4H, broad s, 2×CH$_2$), 7.06–7.3 (3H, m, aromatics), 9.34 (1H, broad, NH), 11.1 (1H, broad, NH), 11.8 (1H, broad, OH). HRMS (ESI$^+$) calculated for $C_{16}H_{17}FN_5O_4$ [M+H$^{+}$]: 362.1265. found: 362.1281.

EXAMPLE 31

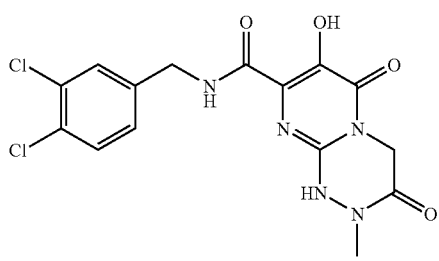

N-(3,4-Dichlorobenzyl)-7-hydroxy-2-methyl-3,6-dioxo-2,3,4,6-tetrahydro-1H-pyrimido[2,1-c][1,2,4]triazine-8-carboxamide. $^1$HNMR 400 MHz (DMSO-$d_6$) δ (ppm): 3.26 (3H, s, NCH$_3$), 4.45 (2H, s, CH$_2$), 4.49 (2H, d, J=6.6 Hz, NCH$_2$), 7.32 (1H, m, aromatic), 7.55–7.65 (2H, m, aromatics), 9.39 (1H, broad t, NH), 11.1 (1H, broad, NH), 11.7 (1H, broad, OH). HRMS (ESI$^+$) calculated for $C_{15}H_{14}Cl_2N_5O_4$ [M+H$^+$]: 398.0423. found: 398.0437.

EXAMPLE 32

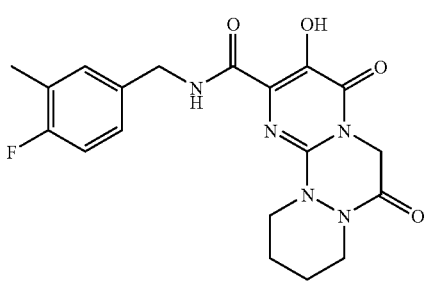

2-Hydroxy-1,9-dioxo-5,6,7,8,9,10-hexahydro-1H-4,4b,8a,10a-tetraaza-phenanthrene-3-carboxylic acid 4-fluoro-3-methyl-benzylamide. $^1$H NMR (500 MHz, CDCl$_3$) δ ppm 11.83 (1H, br s), 7.67 (1H, t, J=5.6 Hz), 7.13–7.16 (1H, m), 7.09–7.13 (1H, m), 6.98 (1H, t, J=8.9 Hz), 4.61 (2H, s), 4.53 (2H, d, J=6.4 Hz), 3.74–3.78 (2H, m), 3.70–3.74 (2H, m), 2.27 (3H, s), 1.84–1.90 (2H, m), 1.77–1.83 (2H, m); $^{13}$C NMR (126 MHz, CDCl$_3$) δ ppm 168.12, 163.47, 162.16, 157.22, 143.92, 143.49, 133.16, 133.14, 129.62, 129.56, 125.40, 115.97, 115.80, 48.98, 43.99, 43.89, 42.51, 23.31, 22.80.

HRMS (ESI) calcd for $C_{19}H_{21}N_5O_4F$ (M+H) 402.1578. found 402.1574.

EXAMPLE 33

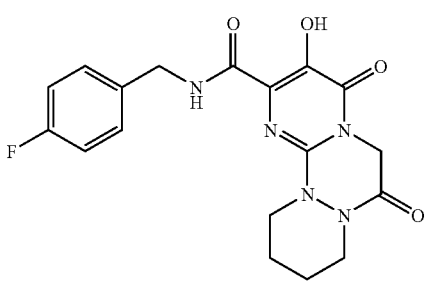

2-Hydroxy-1,9-dioxo-5,6,7,8,9,10-hexahydro-1H-4,4b,8a,10a-tetraaza-phenanthrene-3-carboxylic acid 4-fluoro-benzylamide. $^1$H NMR (500 MHz, CDCl$_3$) δ ppm: 11.80 (1H, s), 7.69 (1H, t, J=5.2 Hz), 7.28–7.34 (2H, m), 7.03–7.08 (2H, m), 4.61 (2H, s), 4.58 (2H, d, J=6.4 Hz), 3.74–3.78 (2H, m), 3.70–3.74 (2H, m), 1.84–1.90 (2H, m), 1.77–1.83 (2H, m); $^{13}$C NMR (126 MHz, CDCl$_3$) δ ppm 168.12, 163.47, 162.16, 157.22, 143.92, 143.49, 133.16, 133.14, 129.62, 129.56, 125.40, 115.97, 115.80, 48.98, 43.99, 43.89, 42.51, 23.31, 22.80. HRMS (ESI) calcd for $C_{18}H_{17}N_5O_4F$ (M−H) 386.1265. found 386.1261.

EXAMPLE 34

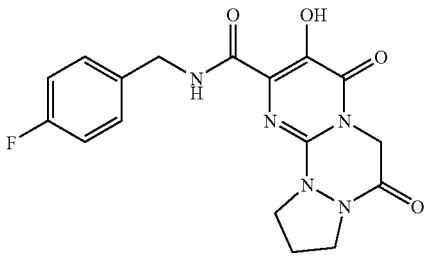

7-Hydroxy-4,6-dioxo-2,3,4,5-tetrahydro-1H,6H-3a,5a,9,9b-tetraaza-benz[e]indene-8-carboxylic acid 4-fluoro-benzylamide. $^1$H NMR (500 MHz, CDCl$_3$) δ ppm 11.77 (1H, s), 7.66 (1H, t, J=5.6 Hz), 7.30 (2H, dd, J=8.4, 5.3 Hz), 7.05 (2H, t, J=8.5 Hz), 4.65 (2H, s), 4.58 (2H, d, J=6.1 Hz), 3.87 (2H, t, J=7.2 Hz), 3.81 (2H, t, J=6.9 Hz), 2.35 (2H, qd, J=6.9, 6.7 Hz). HRMS (ESI) calcd for C$_{17}$H$_{15}$N$_5$O$_4$F (M−H) 372.1108. found 372.1116.

EXAMPLE 35

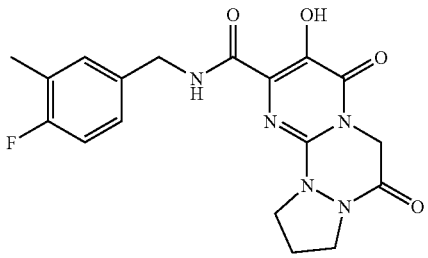

7-Hydroxy-4,6-dioxo-2,3,4,5-tetrahydro-1H,6H-3a,5a,9,9b-tetraaza-benz[e]indene-8-carboxylic acid 4-fluoro-3-methyl-benzylamide. $^1$H NMR (500 MHz, CDCl$_3$) δ ppm 11.80 (1H, s), 7.60–7.68 (1H, m), 7.12–7.17 (1H, 7.10 (1H, td, J=5.3, 2.4 Hz), 6.95–7.02 (1H, m), 4.64 (2H, s), 4.53 (2H, d, J=6.1 Hz), 3.87 (2H, t, J=7.2 Hz), 3.81 (2H, t, J=6.7 Hz), 2.35 (2H, qd, J=6.9, 6.7 Hz), 2.27 (3H, d, J=1.8 Hz); $^{13}$C NMR (126 MHz, CDCl$_3$) δ ppm 168.02, 161.99, 160.04, 157.95, 156.80, 144.07, 144.03, 132.79, 132.76, 131.06, 131.02, 126.74, 126.68, 125.64, 125.50, 125.14, 115.55, 115.38, 47.69, 45.10, 44.42, 42.57, 23.77, 14.69. HRMS (ESI) calcd for C$_{18}$H$_{17}$N$_5$O$_4$F (M−H) 386.1265. found 386.1258.

EXAMPLE 36

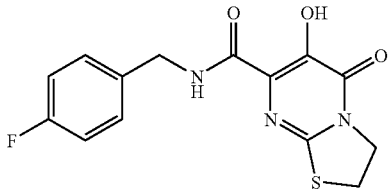

N-(4-Fluorobenzyl)-6-hydroxy-5-oxo-3,5-dihydro-2H-thiazolo[3,2-a]pyrimidine-7-carboxamide. $^1$HNMR 400 MHz (CDCl$_3$) δ (ppm): 3.51 (2H, t, J=7.5 Hz, CH$_2$), 4.50 (2H, t, J=7.5 Hz, CH$_2$), 4.5 7 (2H, d, J=6.1 Hz, CH$_2$), 7.07 (2H, m, aromatics), 7.32 (2H, m, aromatics), 7.80 (1H, broad t, NH), 12.07 (1H, s, OH). Anal. Calcd for C$_{14}$H$_{12}$FN$_3$O$_3$S: C, 52.33; H, 3.76; N, 13.07. Found: C, 52.24; H, 3.69; N, 12.97.

EXAMPLE 37

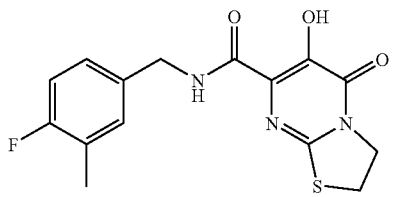

N-(4-Fluoro-3-methylbenzyl)-6-hydroxy-5-oxo-3,5-dihydro-2H-thiazolo[3,2-a]pyrimidine-7-carboxamide. $^1$HNMR 400 MHz (CDCl$_3$) δ (ppm): 2.30 (3H, d, J=1.9 Hz, CH$_3$), 3.51 (2H, t, J=7.4 Hz, CH$_2$), 4.50 (2H, t, J=7.4 Hz, CH$_2$), 4.53 (2H, d, J=6.9 Hz, CH$_2$), 7.0 (1H, m, aromatic), 7.15 (2H, m, aromatics), 7.80 (1H, broad t, NH), 12.11 (1H, s, OH). Anal. Calcd for C$_{15}$H$_{14}$FN$_3$O$_3$S: C, 53.72; H, 4.21; N, 12.53. Found: C, 53.46; H, 4.18; N, 12.50.

EXAMPLE 38

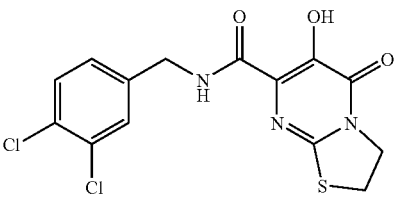

N-(3,4-Dichlorobenzyl)-6-hydroxy-5-oxo-3,5-dihydro-2H-thiazolo[3,2-a]pyrimidine-7-carboxamide. $^1$HNMR 400 MHz (CDCl$_3$) δ (ppm): 3.53 (2H, t, J=7.5 Hz, CH$_2$), 4.51 (2H, t, J=7.4 Hz, CH$_2$), 4.56 (2H, d, J=6.3 Hz, CH$_2$), 7.19 (1H, dd, J=8.0 Hz, J=2.0 Hz, aromatic), 7.43 (1H, d, J=2.0 Hz, aromatic), 7.45 (1H, d, J=8.0 Hz, aromatic), 7.88 (1H, broad t, NH), 11.94 (1H, s, OH). Anal. Calcd for C$_{14}$H$_{11}$C$_{12}$N$_3$O$_3$S: C, 45.17; H, 2.97; N, 11.28. Found: C, 44.94; H, 2.69, N, 10.99.

EXAMPLE 39

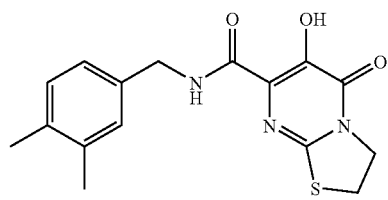

N-(3,4-Dimethylbenzyl)-6-hydroxy-5-oxo-3,5-dihydro-2H-thiazolo[3,2-a]pyrimidine-7-carboxamide. $^1$HNMR 400 MHz (CDCl$_3$) δ (ppm): 2.28 (3H, s, CH$_3$), 2.29 (3H, s, CH$_3$), 3.50 (2H, t, J=7.4 Hz, CH$_2$), 4.49 (2H, t, J=7.4 Hz, CH$_2$), 4.53 (2H, d, J=6.1 Hz, CH$_2$), 7.0–7.16 (3H, m, aromatics), 7.78 (1H, broad t, NH), 12.18 (1H, s, OH). Anal. Calcd for C$_{16}$H$_{17}$N$_3$O$_3$S: C, 57.99; H, 5.17; N, 12.68. Found C, 57.88; H, 5.23; N, 12.48.

EXAMPLE 40

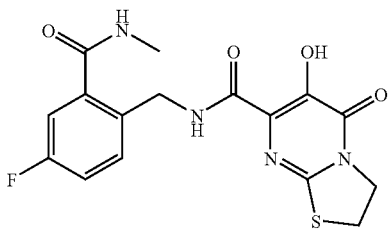

N-(4-Fluoro-2-(methylcarbamoyl)benzyl)-6-hydroxy-5-oxo-3,5-dihydro-2H-thiazolo[3,2-a]pyrimidine-7-carboxamide. ¹HNMR 400 MHz (DMSO-$d_6$) δ (ppm): 2.78 (3H, d, J=4.5 Hz, CH$_3$), 3.55 (2H, t, J=7.5 Hz, CH$_2$), 4.34 (2H, t, J=7.5 Hz, CH$_2$), 4.51 (2H, d, J=6.6 Hz, CH$_2$), 7.28 (2H, m, aromatics), 7.37 (1H, m, aromatic), 8.52 (1H, broad q, NH), 9.24 (1H, broad t, NH), 12.28 (1H, s, OH). Anal. Calcd for $C_{16}H_{15}FN_4O_4S$: C, 50.78; H, 3.99; N, 14.80. Found: C, 50.47; H, 3.99; N, 14.18

EXAMPLE 41

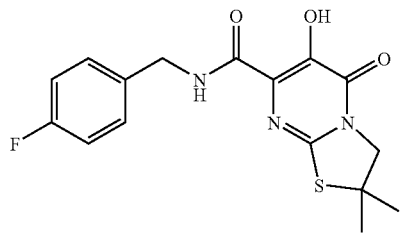

N-(4-Fluorobenzyl)-6-hydroxy-2,2-dimethyl-5-oxo-3,5-dihydro-2H-thiazolo[3,2-a]pyrimidine-7-carboxamide. ¹HNMR 400 MHz (CDCl$_3$) δ (ppm): 1.66 (6H, s, 2×CH$_3$), 4.23 (2H, s, CH$_2$), 4.57 (2H, d, J=6.6 Hz, NCH$_2$) 7.07 (2H, m aromatics), 7.33 (2H, m, aromatics), 7.83 (1H, broad t, NH), 12.08 (1H, s, OH). HRMS (ESI⁺) calculated for $C_{16}H_{17}FN_3O_3S$ [M+H⁺]: 350.0975. found: 350.0970

EXAMPLE 42

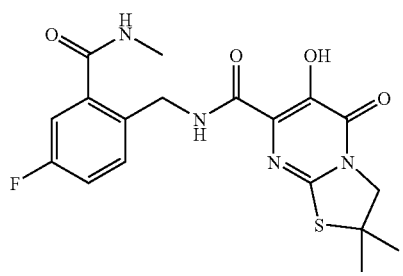

N-(4-Fluoro-2-(methylcarbamoyl)benzyl)-6-hydroxy-2,2-dimethyl-5-oxo-3,5-dihydro-2H-thiazolo[3,2-a]pyrimidine-7-carboxamide. ¹HNMR 400 MHz (CDCl$_3$) δ (ppm): 1.64 (6H, s, 2×CH$_3$), 3.05 (3H, d, J=4.5 Hz, NCH$_3$), 4.20 (2H, s, CH$_2$), 4.62 (2H, d, J=6.6 Hz, NCH$_2$), 7.10–7.2 (2H, m, aromatics), 7.52 (1H, dd, J=5.6 Hz and J=8.6 Hz, aromatic), 8.56 (1H, broad t, NH), 12.14 (1H, s, OH). HRMS (ESI⁺) calculated for $C_{18}H_{20}FN_4O_4S$ [M+H⁺]: 407.1189. found: 407.1174.

EXAMPLE 43

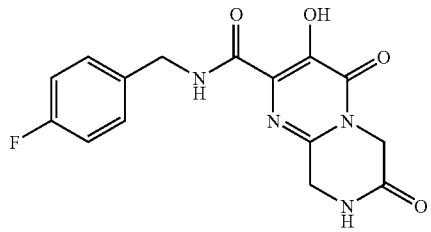

N-(4-Fluorobenzyl)-3-hydroxy-4,7-dioxo-6,7,8,9-tetrahydro-4H-pyrazino[1,2-a]pyrimidine-2-carboxamide. ¹HNMR 400 MHz (CDCl$_3$) δ (ppm): 4.47 (2H, d, J=2.5 Hz, NCH$_2$), 4.61 (2H, d, J=6.5 Hz, NCH$_2$), 4.70 (2H, s, CH$_2$), 6.26 (1H, broad, NH), 7.09 (2H, m, aromatics), 7.34 (2H, m, aromatics), 7.79 (1H, broad, NH), 12.29 (1H, s, OH). HRMS (ESI⁺) calculated for $C_{15}H_{14}FN_4O_4$ [M+H⁺]: 333.0999. found: 333.0985.

EXAMPLE 44

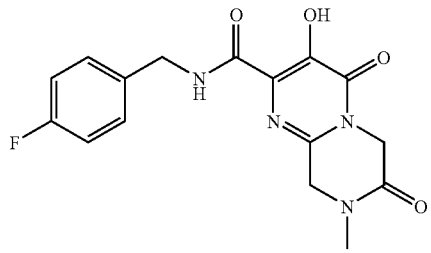

N-(4-Fluorobenzyl)-3-hydroxy-8-methyl-4,7-dioxo-6,7,8,9-tetrahydro-4H-pyrazino[1,2-a]pyrimidine-2-carboxamide. ¹HNMR 400 MHz (CDCl$_3$) δ (ppm): 3.12 (3H, s, NCH$_3$), 4.44 (2H, s, CH$_2$), 4.60 (2H, d, J=6.1 Hz, CH$_2$), 4.70 (2H, s, CH$_2$), 7.09 (2H, m, aromatics), 7.34 (2H, m, aromatics), 7.79 (1H, broad t, NH), 12.25 (1H, s, OH).

EXAMPLE 45

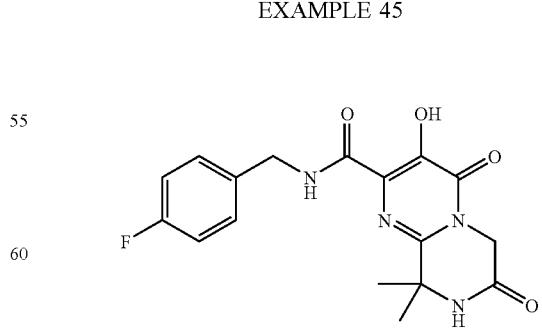

N-(4-fluorobenzyl)-3-hydroxy-9,9-dimethyl-4,7-dioxo-6,7,8,9-tetrahydro-4H-pyrazino[1,2-a]pyrimidine-2-carboxamide. Intermediate 30, ethyl 3-(benzoyloxy)-9,9-dimethyl- 4,7-dioxo-6,7,8,9-tetrahydro-4H-pyrazino[1,2-a]pyrimidine-2-carboxylate, (1 mmol), was dissolved in 4 mL of DMF. To this was added 4-fluorobenzylamine (0.457 mL, 4 mmol) and triethylamine (0.139 mL, 1 mmol). The mixture was warmed to 80° C. and allowed to stir overnight, after which it was allowed to cool to room temperature and transferred to a seperatory funnel. The mixture was diluted with ethyl acetate, washed with 1N HCl, dried over $Na_2SO_4$ then concentrated in vacuo. Methanol and ether were added to the residue and the resulting precipitate isolated by filtration. $^1$H NMR (500 MHz, DMSO) δ: 1.56 (s, 3H), 4.50 (m, 4H), 7.17 (m, 2H), 7.38 (m, 2H), 8.72 (brs, 1H), 9.37 (brm, 1H), 12.37 (s, 1H).

EXAMPLE 46

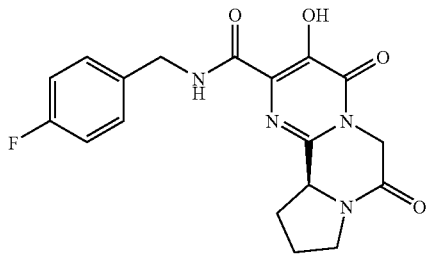

(S)-7-Hydroxy-4,6-dioxo-2,3,4,5,6,9b-hexahydro-1H-3a,5a,9-triaza-benz[e]indene-8-carboxylic acid 4-fluoro-benzylamide. $^1$H NMR (500 MHz, $CDCl_3$) δ ppm: 12.25 (1 H, s) 7.74 (1 H, t, J=5.80 Hz) 7.21–7.35 (2 H, m) 6.98–7.16 (2 H, m) 5.32 (2 H, d, J=17.40 Hz) 4.45–4.74 (2 H, m) 4.12 (2 H, d) 4.12 (1 H, m) 3.53–3.82 (2 H, m) 2.48–2.64 (1 H, m) 2.24–2.40 (1 H, m) 1.96–2.19 (2 H, m); HRMS (M+H) calcd for $C_{18}H_{17}FN_4O_4$: 373.1312. found: 373.1297.

What is claimed is:

1. A compound of Formula I

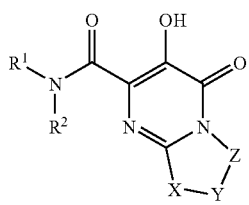

wherein:

$R^1$ is $C_{1-6}(Ar^1)$alkyl;

$R^2$ is hydrogen, hydroxy, $C_{1-6}$alkyl, or $C_{1-6}$alkoxy;

$R^3$ is hydrogen, halo, hydroxy, cyano, $C_{1-6}$alkyl, $C_{1-6}$haloalkyl, $C_{1-6}$alkoxy, $C_{1-6}$haloalkoxy, $N(R^6)SO_2R^7$, $N(R^6)COR^7$, $N(R^6)CO_2R^7$, $OCOR^7$, $OCO_2R^7$, $OCON(R^6)(R^6)$, $COR^7$, $CO_2R^6$, $CON(R^6)(R^6)$, $SOR^7$, $SO_2R^7$, $SO_2N(R^6)(R^6)$, or $Ar^2$;

$R^4$ is hydrogen, halo, hydroxy, cyano, $C_{1-6}$alkyl, $C_{1-6}$alkoxy, $C_{1-6}$haloalkyl, or $C_{1-6}$haloalkoxy;

$R^5$ is hydrogen, halo, hydroxy, cyano, $C_{1-6}$alkyl, $C_{1-6}$alkoxy, $C_{1-6}$haloalkyl, or $C_{1-6}$haloalkoxy;

$R^6$ is hydrogen, $C_{1-6}$alkyl, or $C_{3-7}$cycloakyl;

$R^7$ is $C_{1-6}$alkyl or $C_{3-7}$cycloalkyl;

$R^8$ is hydrogen, $C_{1-6}$alkyl, or benzyl;

$Ar^1$ is

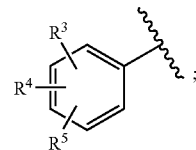

$Ar^2$ is tetrazolyl, triazolyl, pyrazolyl, imidazolyl, pyrrolyl, or dixothiazinyl, and is substituted with 0–2 substituents selected from the group consisting of amino, oxo, halo, and $C_{1-6}$alkyl; and X-Y-Z is $SC(R^8)_2C(R^8)_2$, $SC(R^8)_2C(R^8)_2C(R^8)_2$, or $SC(R^8)_2C(R^8)_2C(R^8)_2C(R^8)_2$;

or a pharmaceutically acceptable salt or solvate thereof.

2. A compound of claim 1 where $R^1$ is

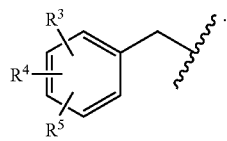

3. A compound of claim 1 where $R^1$ is

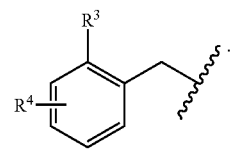

4. A compound of claim 1 where $R^2$ is hydrogen.

5. A compound of claim 1 where $R^3$ is hydrogen, chloro, flouro, methyl, $SO_2N(R^6)(R^6)$, or $NHCOR^7$; $R^4$ is hydrogen, chloro, flouro, or methyl; and $R^5$ is hydrogen.

6. A compound of claim 1 where $R^3$ is triazolyl substituted with 0–1 methyl groups; $R^4$ is hydrogen, chloro, flouro, or methyl; and $R^5$ is hydrogen.

7. A compound of claim 1 where $R^6$ is hydrogen or $C_{1-6}$alkyl.

8. A compound of claim 1 where $R^7$ is $C_{1-6}$alkyl.

9. A compound of claim 1 where X—Y-Z is $SCH_2CH_2$, $SCH_2CH_2CH_2$, and $SCH_2CH_2CH_2CH_2$.

10. A compound of claim 9 where $R^8$ is hydrogen or methyl.

11. A compound of claim 1 selected from the group consisting of

N-(4-Fluorobenzyl)-6-hydroxy-5-oxo-3,5-dihydro-2H-thiazolo[3,2-a]pyrimidine-7-carboxamide;

N-(4-Fluoro-3-methylbenzyl)-6-hydroxy-5-oxo-3,5-dihydro-2H-thiazolo[3,2-a]pyrimidine-7-carboxamide;

N-(3,4-Dichlorobenzyl)-6-hydroxy-5-oxo-3,5-dihydro-2H-thiazolo[3,2-a]pyrimidine-7-carboxamide; p1 N-(3,4-Dimethylbenzyl)-6-hydroxy-5-oxo-3,5-dihydro-2H-thiazolo[3,2-a]pyrimidine-7-carboxamide;

N-(4-Fluoro-2-(methylcarbamoyl)benzyl)-6-hydroxy-5-oxo-3,5-dihydro-2H-thiazolo[3,2-a]pyrimidine-7-carboxamide;

N-(4-Fluorobenzyl)-6-hydroxy-2,2-dimethyl-5-oxo-3,5-dihydro-2H-thiazolo[3,2-a]pyrimidine-7-carboxamide; and N-(4-Fluoro-2-(methylcarbamoyl)benzyl)-6-hydroxy-2,2-dimethyl-5-oxo-3,5-dihydro-2H-thiazolo[3,2-a]pyrimidine-7-carboxamide;

or a pharmaceutically acceptable salt thereof.

12. A composition comprising a therapeutic amount of a compound of claim 1 and a pharmaceutically acceptable carrier.

13. A method for treating HIV infection comprising administering a therapeutically effective amount of a compound of claim 1, or a pharmaceutically acceptable salt thereof, to a patient in need thereof.

14. The method of claim 13, further comprising a therapeutically effective amount of one or more other HIV treatment agents selected from the group consisting of HIV protease inhibitors, HIV nucleoside reverse transcriptase inhibitors, HIV non-nucleoside reverse transcriptase inhibitors, HIV-entry inhibitors, HIV integrase inhibitors, immunomodulators, or a combination thereof.

* * * * *